US009683247B2

(12) United States Patent
Lutes et al.

(10) Patent No.: US 9,683,247 B2
(45) Date of Patent: Jun. 20, 2017

(54) MICROBIAL PRODUCTION OF ALKANOLAMIDES AND AMIDOAMINES AND USES THEREOF

(71) Applicant: REG Life Sciences, LLC., Ames, IA (US)

(72) Inventors: Jason J. Lutes, South San Francisco, CA (US); Stephen del Cardayre, South San Francisco, CA (US)

(73) Assignee: REG LIFE SCIENCES, LLC, Ames, IA (US)

( * ) Notice: Subject to any disclaimer, the term of this patent is extended or adjusted under 35 U.S.C. 154(b) by 29 days.

(21) Appl. No.: 14/394,070

(22) PCT Filed: Mar. 12, 2013

(86) PCT No.: PCT/US2013/030502
§ 371 (c)(1),
(2) Date: Oct. 10, 2014

(87) PCT Pub. No.: WO2013/154721
PCT Pub. Date: Oct. 17, 2013

(65) Prior Publication Data
US 2015/0079643 A1    Mar. 19, 2015

Related U.S. Application Data

(60) Provisional application No. 61/623,711, filed on Apr. 13, 2012.

(51) Int. Cl.
*C12N 1/20*     (2006.01)
*C12P 13/02*    (2006.01)
*C12N 9/10*     (2006.01)
*C12N 9/18*     (2006.01)
*C12N 15/70*    (2006.01)

(52) U.S. Cl.
CPC ............ *C12P 13/02* (2013.01); *C12N 9/1029* (2013.01); *C12N 9/18* (2013.01); *C12N 15/70* (2013.01); *C12Y 203/01086* (2013.01); *C12Y 301/01005* (2013.01)

(58) Field of Classification Search
None
See application file for complete search history.

(56) References Cited

U.S. PATENT DOCUMENTS

| | | |
|---|---|---|
| 5,000,000 A | 3/1991 | Ingram et al. |
| 5,028,539 A | 7/1991 | Ingram et al. |
| 5,424,202 A | 6/1995 | Ingram et al. |
| 5,482,846 A | 1/1996 | Ingram et al. |
| 5,576,282 A | 11/1996 | Miracle et al. |
| 5,602,030 A | 2/1997 | Ingrahm et al. |
| 6,306,812 B1 | 10/2001 | Perkins et al. |
| 6,326,348 B1 | 12/2001 | Vinson et al. |
| 6,348,498 B1 | 2/2002 | Calignano et al. |
| 6,656,972 B2 | 12/2003 | Calignano et al. |
| 2010/0242345 A1 | 9/2010 | Keasling et al. |
| 2010/0257777 A1 | 10/2010 | Sanchez-Riera et al. |
| 2011/0072714 A1 | 3/2011 | Gaertner |
| 2011/0111470 A1 | 5/2011 | Berry et al. |
| 2011/0162259 A1 | 7/2011 | Gaertner |
| 2011/0206630 A1 | 8/2011 | Rude |

FOREIGN PATENT DOCUMENTS

| | | |
|---|---|---|
| WO | WO-99/05245 | 2/1999 |
| WO | WO-2007/136762 A2 | 11/2007 |
| WO | WO-2008/100251 | 8/2008 |
| WO | WO-2010/042664 | 4/2010 |
| WO | WO-2010/062480 A2 | 6/2010 |

OTHER PUBLICATIONS

Rasko et al. (Uniprot Accession No. A8A7Q7, Apr. 2016).*
Ngo et al. in The Protein Folding Problem and Tertiary Structure Prediction, 1994, Merz et al. (ed.), Birkhauser, Boston, MA, pp. 433 and 492-495.*
Adlercreutz et al. "Alkanolamide bioscurfacants: Techno-economic evaluation of biocatalytic versus chemical production," Industrial Biotechnology vol. 6, No. 4, Aug. 1, 2010, pp. 204-211.
Amann et al, "Tightly regulated tac promoter vectors useful for the expression of unfused and fused proteins in *Escherichia coli*," Gene, 69: 301-315 (1988).
Astarita et al. (2006) Am. J. Physiol. Regul. Integr. Comp. Physiol 290:R1407-R1412.
Bacci et al., "Randomized Split-Mouth Study on Postoperative Effects of Palmitoylethanolamide for Impacted Lower Third Molar Surgery," (2011) ISRN Surgery, vol. 2011, Article ID 917350, 6 pages.
Bachur et al., "Fatty Acid Amides of Ethanolamine in Mammalian Tissues," (1965) J. Biol. Chem. 240: 10919-1024.
Baldari et al. "A novel leader peptide which allows efficient secretion of a fragment of human interleukin 1 beta in *Saccharomyces cerevisia*," EMBO J. vol. 6, No. 1, pp. 229-234, 1987.
Black et al., "Cloning, Sequencing and Expression of the fadD Gene of *Escherichia coli* Encoding Acyl Coenzyme A Synthetase," J. Biol. Chem. vol. 267, No. 35, Dec. 15, 1992, pp. 25513-25520.
Brady, S.F., et al. "Palmitoylputrescine, an antibiotic isolated from the heterologous expression of DNA extracted from bromeliad tank water." J. Nat. Prod., vol. 67, No. 8, Aug. 2004, pp. 1283-1286.
Camilli et al. "Bacterial Small-Molecule Signaling Pathways," Science vol. 311, No. 5764, Feb. 24, 2006, pp. 1113-1116.
Caviglia et al., Rat Long Chain Acyl-CoA Synthetase 5, but Not 1, 2, 3, or 4, Complements *Escherichia coli* fadD*, The Journal of Biological Chemistry, 279(12): 1163-1169 (2004).
Cho et al. "Defective Export of a Periplasmic Enzyme Disrupts Regulation of Fatty Acid Synthesis," J. Biol. Chem. vol. 270, No. 9, Mar. 3, 1995, pp. 4216-4219.
Communication on EP Application 13711261.1, dated Oct. 7, 2015.

(Continued)

*Primary Examiner* — Richard Hutson
(74) *Attorney, Agent, or Firm* — Foley & Lardner LLP

(57) ABSTRACT

The disclosure relates to a recombinant microorganism engineered to express an enzyme which catalyzes the conversion of a primary amine and an acyl thioester to a fatty amide. The disclosure further encompasses a method of producing a fatty amide by culturing the recombinant microorganism in the presence of a carbon source.

21 Claims, 7 Drawing Sheets

(56) References Cited

OTHER PUBLICATIONS

Craig et al., "Expanding Small-Molecule Functinal Metagenomics through parallel Screening of Broad-Host-Range Cosmid Environmental DNA Libraries in Diverse Proteobacteria," Applied and Environmental Microbiology, vol. 76, No. 5, Mar. 1, 2010, pp. 1633-1641.
Cronan et al. "FadR, transcriptional co-ordination of metabolic expediency," (1998) Mole. Microbiol. 29(4):937-943.
Datsenko et al., "One-step Inactivation of Chromosomal Genes in *Escherichia coli* K-12 using PCR Products," Proc. Natl. Acad. Sci. U.S.A., 97(12): 6640-6645 (2000).
Fu et al. Oleylethanolamide regulates feeding and body weight through activation of the nuclear receptor PPAR-beta), (2003) Nature 425(6953): 90-93.
Heath et al., "Lipid Biosynthesis as a Target for Antibacterial Agents," Prog. Lipid Res. 40(6): 467-97 (2001).
International Search Report issued on PCT/US2013/030502, mailed Jun. 3, 2013.
Johnson, et al., "Genetic Analysis of the Role of *Saccharomyces cerevisiae* Acyl-CoA Synthetase Genes in Regulating Protein N-Myristoylation*," The Journal of Biological Chemistry, vol. 269, No. 27, Issue of Jul. 1994, pp. 18037-18046, 10 pages.
Knoll et al., "Biochemical Studies of Three *Saccharomyces cerevisiae* Acyl-CoA Synthetases, Faa1p, Faa2p, and Faa3p," J. Biol. Chem., 269(23): 16348-16356 (1994).
Kurjan et al., Structure of a Yeast Pheromone Gene (MFx): A Putative x-Factor precursor Contains Four Tandem Copies of Mature x-Factor, Cell, vol. 30, pp. 933-943 (1982).
Lo Verme et al., "The Nuclear Receptor Peroxisome Proliferator-Activated Receptor-alpha Mediates the Anti-Inflammatory Actions of Palmitoylethanolamide," (2004) Mol. Pharmacol. 67(1):15-19.
Maniatis et al. Regulation of Inducible and Tissue-Specific Gene Expression, Science 236, pp. 1237-1245, Jun. 5, 1987.
Murli et al. "A Role for the umuDC Gene Products of *Escherichia coli* in Increasing Resistance to DNA Damage in Stationary Phase by Inhibiting the Transition to Exponential Growth," vol. 182, No. 4, Feb. 2000, J. Bacteriol. pp. 1127-1135.
Pacher et al. "The Endocannabinoid System as an Emerging Target of Pharmacotherapy," (2006) Pharmacol. Rev. 58 (3):389-462.
Petrosino et al., "N-palmitoyl-ethanolamine: Biochemistry and new therapeutic opportunities," (2010) Biochimie 92(6): 724-7.
Reading et al. "Quorum sensing: the many languages of bacteria," FEMS Microbiol. Lett. 254, 2006, pp. 1-11.
Schultz et al. "Expression and secretion in yeast of a 400-kDa envelope glycoprotein derived from Epstein-Barr virus," (1987) Gene 54 pp. 113-123.
Shockey et al., "Arabidopsis Contains Nine Long-Chain Acyl-Coenzyme A Synthetase Genes that Participate in Fatty Acid and Glycerolipid Metabolism," Plant. Physiol., 29:1710-1722 (2002).
Studier et al., Gene Expression Technology: Methods in Enzymology 185, Academic Press, San Diego, CA, pp. 60-89 (1990).
Tan et al. (2006) AAPS J. 8(3): E461-465.
Tufvesson et al, "Solvent-free enzymatic synthesis of fatty alkanolamides," Biotechnology and Bioengineering, vol. 97, No. 3, Jun. 15, 2007, pp. 447-453.
Venturi "Regulation of quorum sensing in Pseudomonas," FEMS Microbiol. Rev. vol. 30, 2006, pp. 274-291.
Vetting et al, "Structure and functins of the GNAT superfamily of acetyltransferases," Archives of Biochemistry and Biophysics, vol. 433, No. 1, Jan. 1, 2005, pp. 212-226.
Communication issued on European Application 13711261.1, mailed Jun. 22, 2016.
Notice of Reasons for Rejection issued on Japanese application 2015-505727, mailed Feb. 8, 2017.
Office Action issued on Chinese Application 201380026545.3, mailed Dec. 20, 2016, English translation included.
Communication issued on EP Application 13711261.1, mailed Mar. 16, 2017.

* cited by examiner

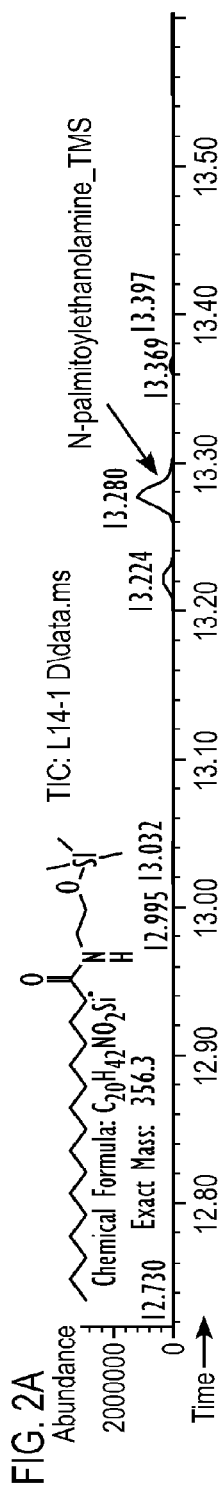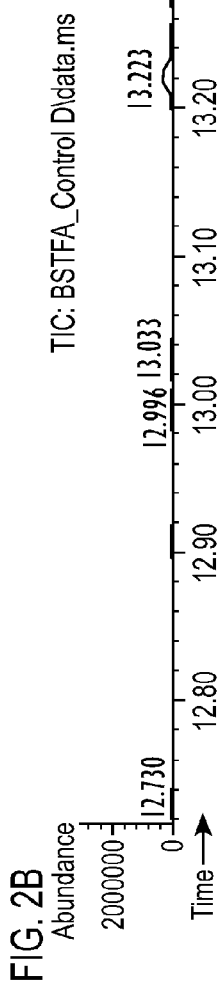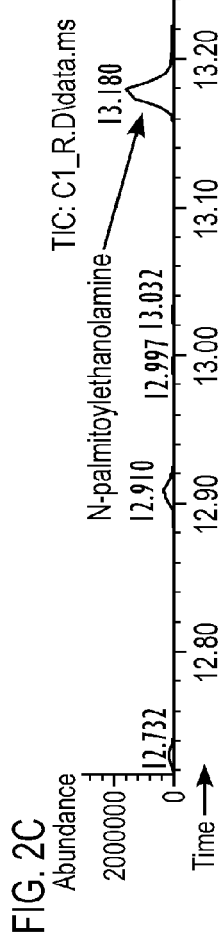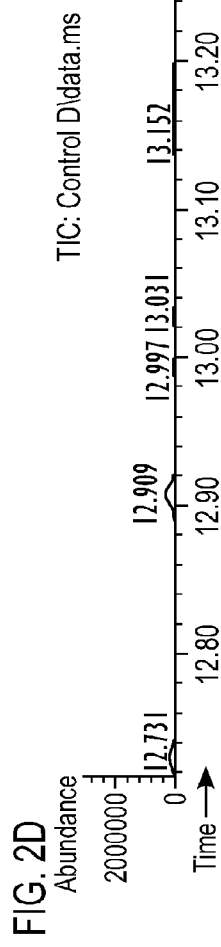
FIG. 2A
FIG. 2B
FIG. 2C
FIG. 2D

MICROBIAL PRODUCTION OF ALKANOLAMIDES AND AMIDOAMINES AND USES THEREOF

CROSS-REFERENCE TO RELATED APPLICATIONS

This application is the National Phase of International Application No. PCT/US2013/30502 filed 12 Mar. 2013, which designated the U.S. and that International Application was published under PCT Article 21(2) in English, which claims the benefit of priority to U.S. Provisional Application Ser. No. 61/623,711, filed 13 Apr. 2012, all of which applications are incorporated herein by reference in their entirety.

FIELD

The disclosure relates to a microorganism that is engineered to express an enzyme in order to produce fatty amides when cultured in the presence of a carbon source.

BACKGROUND

Fatty amides are endogenous components of animal and plant lipids that have a wide variety of biochemical and physiological functions (Bachur et al. (1965) *J. Biol. Chem.* 240:1019-1024). Endogenous fatty amides such as N-palmitoylethanolamine (PEA), N-arachidonoyl ethanolamine (anandamide), N-oleoyl ethanolamide (OEA), and N-arachidonoyl dopamine (NADA) function as signaling molecules in the central and peripheral nervous system (see, e.g., Tan et al. (2006) *AAPS J.* 8 (3): E461-E465; and Lo Verme et al. (2004) *Mol. Pharmacol.* 67(1):15-19). PEA has been demonstrated to exert anti-inflammatory and anti-nociceptive activities, and pharmaceutical formulations of PEA for the treatment of pain are available in Europe under the trade name NORMAST (Petrosino et al. (2010) *Biochimie* 92 (6):724-7; and Bacci et al. (2011) *ISRN Surgery*, Volume 2011, Article ID 917350, 6 pages; doi:10.5402/2011/917350).

Fatty amides, such as fatty alkanolamides and fatty aminoamides, also have a wide variety of non-pharmaceutical commercial uses. Fatty alkanolamides and fatty aminoamides are useful as foaming agents, surfactants, or intermediates thereof in the production of personal care products (e.g., shampoos, body washes, and facial cleansers), cosmetic formulations (e.g., blushes, mascaras, and lipsticks), and household cleaning products (e.g., laundry detergents, dishwashing liquids, and surface cleaning compositions). Fatty alkanolamides and fatty aminoamides also are useful as fuel additives. It is estimated that 100,000 tons of alkanolamides are consumed in the global market each year (Adlercreutz et al. (2010) *Industrial Biotechnology* 6 (4): 204-211).

Fatty alkanolamides for commercial use classically have been produced via costly synthetic organic reactions between a fatty acid or fatty acid methyl ester derived from feedstocks such as natural oils or fats and crude oil and an alkanolamine (Adlercreutz et al., supra, and Frost & Sullivan, "Nonionic Surfactants in the Industrial Triad" (2002)). For example, PEA can be produced by reacting palmitoyl fatty acids derived from coconut oils with monoethanolamine in a Schotten-Baumann reaction, as follows:

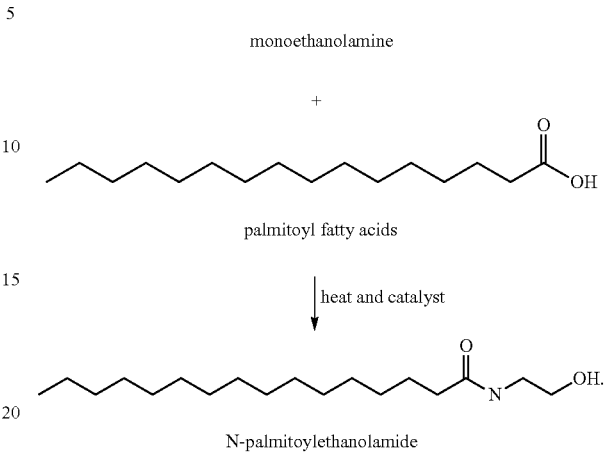

Fatty alkanolamides have also been produced biosynthetically. For example, OEA can be produced from phosphatidylethanolamine (PE) and sn-1-oleoyl-phosphatidylcholine (PC) precursors via a two enzyme process, wherein PE and sn-1-oleoyl-PC are reacted with N-acyl transferase to form N-acyl phosphatidylethanolamine (NAPE) which is then combined with lyso-PC and reacted with NAPE-specific phospholipase D to form OEA and phosphatidic acid (see Astarita et al. (2006) *Am. J. Physiol. Regul. Integr. Comp. Physiol* 290:R1407-R1412).

These methods, as well as other methods known in the art for synthesizing fatty amides, often involve inefficient reaction steps and are thus costly, from both an economical and environmental perspective. Hence, there is a need for improved methods and reagents for the production of fatty amides, wherein the length and saturation of fatty chain as well as the type of the amide head group can be controlled efficiently.

SUMMARY

One aspect of the present disclosure provides a recombinant microorganism including a nucleic acid sequence encoding a polypeptide that catalyzes the conversion of a primary amine and an acyl thioester to a fatty amide, wherein the microorganism is cultured in the presence of a carbon source. Herein, the microorganism is engineered to express the nucleic acid sequence that encodes the polypeptide that catalyzes the conversion of a primary amine and an acyl thioester to a fatty amide when the microorganism is cultured in the presence of a carbon source. In one embodiment, the carbon source is a carbohydrate. In another embodiment, the polypeptide is a palmitoylputrescine synthase (PPS) polypeptide. In still another embodiment, the polypeptide is a N-(4-amino-2-hydroxylbutyl)tetradecanamide synthase (AhtS) polypeptide.

Another aspect of the disclosure provides a palmitoylputrescine synthase (PPS) polypeptide that has the amino acid sequence of SEQ ID NO: 1. In one embodiment, the PPS polypeptide includes an amino acid sequence that has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to the amino acid sequence of SEQ ID NO: 1. In another embodiment, the PPS polypeptide is encoded by a nucleic acid sequence comprising the nucleic acid sequence of SEQ ID NO: 2.

Another aspect of the disclosure provides a N-(4-amino-2-hydroxybutyl)tetradecanamide synthase (AhtS) polypeptide that has the amino acid sequence of SEQ ID NO: 3. In one embodiment, the AhtS polypeptide includes an amino acid sequence that has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to the amino acid sequence of SEQ ID NO: 3. In another embodiment, the AhtS polypeptide is encoded by a nucleic acid sequence comprising the nucleic acid sequence of SEQ ID NO: 22.

Yet, another aspect of the disclosure provides a recombinant microorganism, wherein the primary amine includes, but is not limited to, 3-dimethylamino-1-propylamine, (±)-1-amino-2-propanol, 2-methoxyethylamine, 3-amino-1-propanol, 2-amino-1,3-propanediol, 3-methoxypropylamine, N-(2-hydroxyethyl)ethylenediamine, and butylamine, 1,4-diaminobutane, or a combination thereof.

Still, another aspect of the disclosure provides a recombinant microorganism, wherein the acyl thioester is a fatty acyl-ACP or a fatty acyl-CoA. The fatty acyl-ACP or the fatty acyl-CoA is produced by the microorganism.

The disclosure further encompasses a recombinant microorganism that includes a nucleic acid sequence encoding one or more of a fatty acid biosynthetic polypeptide, a thioesterase polypeptide (EC 3.1.2.14 or EC 3.1.1.5) and an acyl-CoA synthase polypeptide (EC 2.3.1.86). In one embodiment, the nucleic acid sequence encoding the thioesterase polypeptide is tesA. In another embodiment, the nucleic acid sequence encoding the acyl-CoA synthase polypeptide is fadD. In yet another embodiment, the microorganism includes a nucleic acid sequence encoding a fatty acid biosynthetic polypeptide, including, but not limited to accABCD, FabD, FabH, FabG, FabB, FabA, FabZ, FabF, FabI, and/or FadR.

The disclosure further contemplates a microorganism including, but not limited to, bacteria, cyanobacteria, algae, and fungi. In one embodiment, the bacteria is *E. coli*. In another embodiment, the fungi is yeast or filamentous fungi. In yet another embodiment, the microorganism includes, but is not limited to, *Saccharomyces cerevisiae, Candida lipolytica, Escherichia coli, Arthrobacter, Rhodotorula glutinins, Acinetobacter, Candida lipolytica, Botryococcus braunii, Vibrio furnissii, Micrococcus leuteus, Stenotrophomonas maltophilia, Bacillus subtilis, Bacillus lichenoformis, Psuedomonus putida, Psuedomonas florescens, Streptomyces coelicolor, Synechococcus* sp. PCC7002, *Thermosynechococcus elongatus* BP-1, *Prototheca moriformis, Prototheca krugani, Prototheca stagnora, Prototheca zopfii*, or *Chorella protothecoide* cell. In still another embodiment, the microorganism includes, but is not limited to *Arthrobacter* AK 19, *Acinetobacter* sp. strain M-1, *E. coli* B, *E. coli* C, *E. coli* K, or *E. coli* W cell.

Another aspect of the disclosure provides a recombinant microorganism including a nucleic acid sequence encoding a polypeptide that catalyzes the conversion of a primary amine and an acyl thioester to a fatty amide, wherein the polypeptide that catalyzes the conversion of a primary amine and an acyl thioester to a fatty amide is endogenous to the microorganism.

Another aspect of the disclosure provides a recombinant microorganism including a nucleic acid sequence encoding a polypeptide that catalyzes the conversion of a primary amine and an acyl thioester to a fatty amide, wherein the polypeptide that catalyzes the conversion of a primary amine and an acyl thioester to a fatty amide is exogenous to the microorganism.

Still, another aspect of the disclosure provides a recombinant microorganism including a nucleic acid sequence encoding an enzyme that catalyzes the conversion of a primary amine and an acyl thioester to a fatty amide. In one embodiment, the fatty amide is a fatty alkanolamide and/or a fatty amidoamine. In another embodiment, the fatty amide is a C14, C16, and/or C18 fatty alkanolamide and/or a C14, C16, or C18 fatty amidoamine. In yet another embodiment, the fatty amide is a C8, C9, C10, C11, C12, C13, C14, C15, C16, C17, C18, C19 or C20 fatty alkanolamide and/or a C8, C9, C10, C11, C12, C13, C14, C15, C16, C17, C18, C19 or C20 fatty amidoamine.

Yet, another aspect of the disclosure provides a recombinant microorganism including a nucleic acid sequence encoding a polypeptide that catalyzes the conversion of a primary amine and an acyl thioester to a fatty amide, wherein the microorganism expresses a serine decarboxylase polypeptide.

The disclosure further encompasses a method of producing a fatty amide including: (a) providing a recombinant microorganism including a nucleic acid sequence encoding a polypeptide that catalyzes the conversion of a primary amine and an acyl thioester to a fatty amide; and (b) culturing the recombinant microorganism in a culture medium under conditions suitable for expression of the nucleic acid sequence encoding the polypeptide that catalyzes the conversion of a primary amine and an acyl thioester to a fatty amide in the presence of at least one substrate for the polypeptide. This method may further include isolating the fatty amide from the culture medium. The method can be used to produce fatty amides. In one embodiment, the fatty amide is a fatty alkanolamide and/or a fatty amidoamine. In another embodiment, the fatty amide is a C8, C9, C10, C11, C12, C13, C14, C15, C16, C17, C18, C19 or C20 fatty alkanolamide and/or a C8, C9, C10, C11, C12, C13, C14, C15, C16, C17, C18, C19 or C20 fatty amidoamine.

BRIEF DESCRIPTION OF THE FIGURES

The present disclosure is best understood when read in conjunction with the accompanying figures, which serve to illustrate the preferred embodiments. It is understood, however, that the disclosure is not limited to the specific embodiments disclosed in the figures.

FIG. 2A depicts a peak having a GC retention time of 13.3 min which was identified as trimethylsilyl (TMS)-protected N-palmitoylethanolamide by MS analysis depicted in FIG. 2E. FIGS. 2B-2D are control chromatograms of BSTFA alone, N-palmitoylethanolamide without BSTFA derivatization, and blank reaction, respectively.

DETAILED DESCRIPTION

Figure 1:
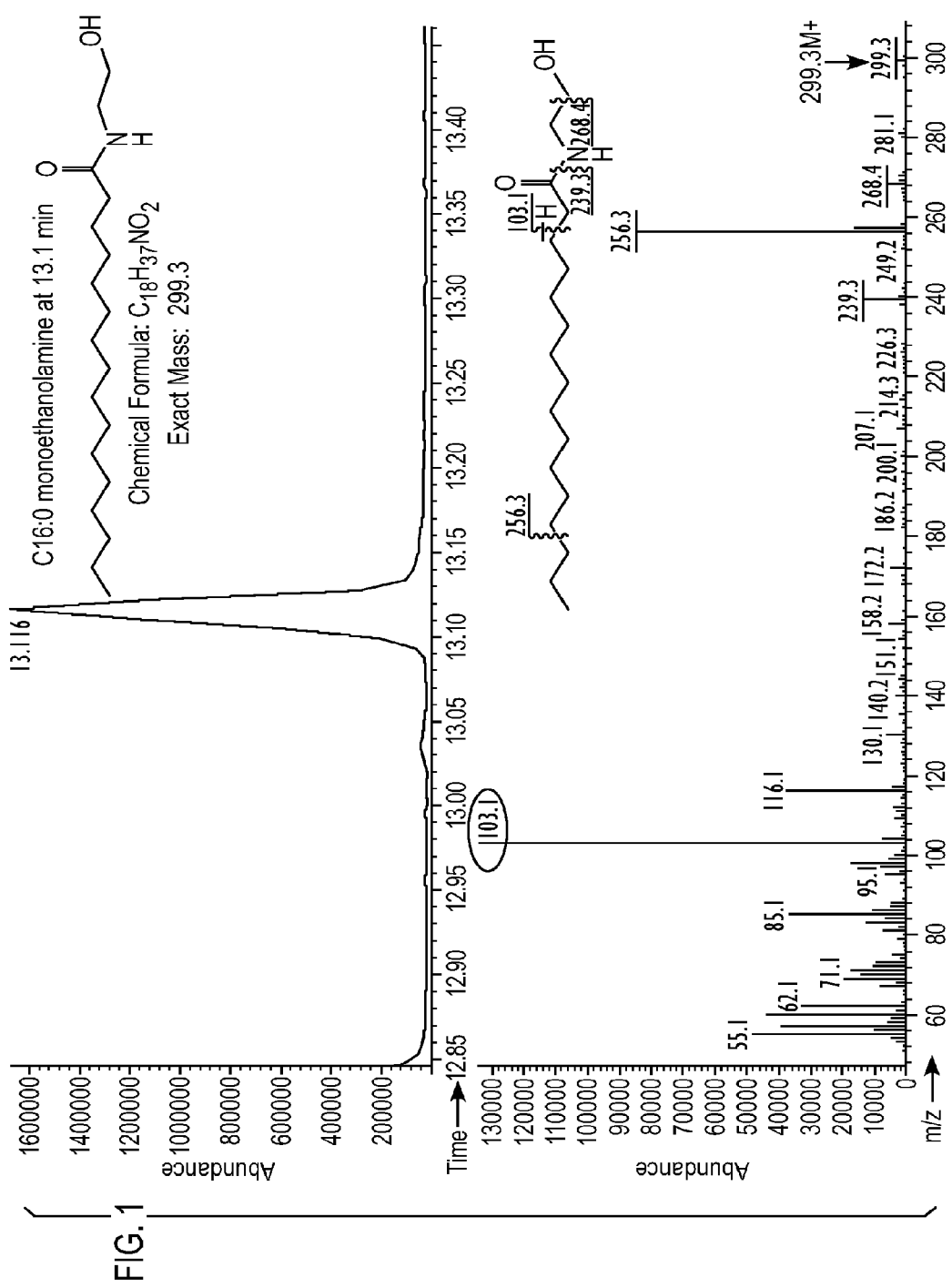
FIG. 1 is a representative gas chromatography-mass spectroscopy (GC-MS) chromatogram of the fatty species produced by *E. coli* MG1655 strain DG5 transformed with an expression vector encoding a palmitoylputrescine synthase (PPS) cultured in the presence of ethanolamine. The upper panel depicts a peak having a GC retention time of 13.1 min which was identified as N-palmitoylethanolamide by MS analysis depicted in the lower panel.

The natural antibiotic palmitoylputrescine can be produced by bacteria which express palmitoylputrescine synthase (PPS) (GenBank Accession No. AAV33349.1 (hereinafter "AAV33349")) (SEQ ID NO: 1) encoded by the nucleic acid sequence of GenBank Accession No. AY632377.1 (hereinafter "AY632377") (SEQ ID NO: 2) (Brady et al. (2004) *J. Nat. Prod.* 67:1283-1286). When overexpressed in *E. coli*, the PPS encoded by AY632377 was demonstrated to produce only one major N-acyl derivative of putrescine (1,4-diaminobutane), namely palmitoylputrescine (Brady et al., supra). A homologue encoding the enzyme, N-(4-amino-2_hydroxylbutyl)tetradecanamide synthase (AhtS) (GeneBank Accession No. ACX33975.1) (SEQ ID NO: 3), has an amino acid sequence that is 38% identical to the amino acid sequence of PPS. The N-(4-amino-2-hydroxybutyl)tetradecanamide synthase (AhtS) gene from uncultured bacterium RM44 (GenBank GQ869386) is shown in (SEQ ID NO: 22).

The disclosure is based, at least in part, on the discovery that a microorganism (e.g., bacteria) expressing a PPS or AhtS can produce fatty amides from acyl thioester precursors when cultured in the presence of a carbon source. Without wanting to be bound by theory, it is believed that PPS directly catalyzes the amidation between an acyl thioester and a primary amine. This is the first time that a microorganism has been specifically engineered to express an enzyme such as PPS or AhtS in order to produce fatty amides. This is advantageous because the microorganism thereby serves as a convenient biological factory that generates fatty amides of desired chain length, including in branched or unbranched form. In addition, various different feedstocks (e.g., corn, sugar cane, glycerol, switchgrass) can be used interchangeably to supply the necessary carbon source for the microorganism, allowing for flexibility. As such, the microorganism can be used to produce fatty amides upon demand that can be harvested via fermentation, thereby bypassing the cumbersome and costly prior art systems that still rely on expensive natural oils and complicated synthetic chemistry. Fatty amides are needed for the production of numerous products including, but not limited to, foaming agents, cationic surfactants, intermediates for use as shampoos and bath products, emulsifying agents in cosmetics and pharmaceuticals, fuel additives, and the like.

The disclosure provides a recombinant microorganism engineered to express a nucleic acid sequence encoding a polypeptide that catalyzes the conversion of a primary amine and an acyl thioester to a fatty amide, wherein the microorganism is cultured in the presence of a carbon source. In one embodiment, the carbon source is a carbohydrate. More specifically, the microorganism was engineered such that an enzyme like PPS or AhtS is expressed in order to catalyze the amidation between any primary amine (e.g, ethanolamine, amine 3-dimethylamino-1-propylamine) with an acyl thiol-ester (e.g., acyl-CoA or acyl-ACP) in order to produce fatty amides such as alkanolamides and amidoamines. This is a novel process because fatty alkanolamides (e.g., intermediates used in the synthesis of cocamidopropyl betaine) and amidoamines have so far been produced synthetically from feed stocks such as natural oils (or fats) and crude oil, which is an inefficient process because it relies on refining the raw materials until the desired materials are achieved. In comparison, the present disclosure provides a production method, wherein a microorganism is engineered to express enzymes such that, for example, alkanolamides and fatty N-(3-dimethylamino-1-propylamine)amides are synthesized biochemically, which is a much more effective process for producing fatty amides. Amino acids or carbohydrates can be added to the fermentation medium of the microorganism to supply the necessary carbon source (see Examples 3-7). Alternatively, the microorganism can be engineered to generate its own primary amine in vivo. For example, the biosynthesis of ethanolamine can be achieved by genetically increasing serine biosynthesis and serine decarboxylation pathways (see Example 8). Enzymatically, AhtS produces the same amide compounds as PPS but with a preference for C14:0 fatty thioester substrates. Both enzymes belong to EC family 2.3.1.X.X.

The disclosure further provides a method of producing a fatty amide in a recombinant microorganism. Fatty amides produced by this method include, but are not limited to, fatty alkanolamides and fatty amidoamines. In one embodiment, the fatty amide is a C14, C16, and/or C18 fatty alkanolamide. In another embodiment, the fatty amide is a C14, C16, and/or C18 fatty amidoamine. The method involves the steps of (a) providing a recombinant microorganism engineered to express a nucleic acid sequence encoding a polypeptide such as PPS or AhtS which catalyzes the conversion of a primary amine and an acyl thioester to a fatty amide; and (b) culturing the recombinant microorganism under conditions suitable for expression of the polypeptide in the presence of at least one substrate for the polypeptide, thereby producing the fatty amide. The microorganism is cultured in the presence of a carbon source. The carbon source can be selected from a wide variety of different sources, including but not limited to, amino acids, carbohydrates, and lipids. In one embodiment, the carbon source is a carbohydrate. The fatty amide that is produced by the microorganism can be isolated from the culture broth (e.g., fermentation broth). In one embodiment, the fatty amide is isolated from the extracellular environment of the microorganism. In another embodiment, the fatty amide is spontaneously secreted, partially or completely, from the microorganism. In another embodiment, the fatty amide is transported into the extracellular environment, optionally with the aid of one or more suitable transport proteins. In yet another embodiment, the fatty amide is passively transported into the extracellular environment.

The terms "fatty amide" and "alkyl amide" refer to a compound having the formula $R^1CONHR^2$, wherein $R^1$ represents an aliphatic group derived from a fatty acid, and $R^2$ represents a substituted or unsubstituted alkyl, substituted or unsubstituted heteroalkyl, substituted or unsubstituted alkenyl, or substituted or unsubstituted heteroalkenyl group derived from a primary amine.

An "acyl thioester" refers to a fatty acid which has been "activated" by a fatty acid biosynthetic pathway of the production host microorganism. The acyl thioester can be generated from a fatty acid endogenous to the microorganism, or the acyl thioester can be generated from a fatty acid provided to the microorganism exogenously. Non-limiting examples of acyl thioesters are acyl-coenzyme A (CoA) and acyl-acyl carrier protein (ACP).

The term "acyl-CoA" refers to an acyl thioester formed between the carbonyl carbon of an alkyl chain and the sulfhydryl group of the 4'-phosphopantetheine moiety of CoA, which has the formula $R^1$—C(O)S-CoA, where $R^1$ is an aliphatic group. The term "acyl-ACP" refers to an acyl thioester formed between the carbonyl carbon of an alkyl chain and the sulfhydryl group of a 4'-phosphopantetheine moiety attached to ACP, which has the formula $R^1$—C(O)S-ACP, where $R^1$ is an aliphatic group.

The term "fatty acid" means a carboxylic acid having the formula $R^1COOH$. $R^1$ represents an aliphatic group, preferably an alkyl group. $R^1$ can comprise between 4 and 26 carbon atoms. In certain embodiments, $R^1$ is at least 5, at least 6, at least 7, at least 8, at least 9, at least 10, at least 11, at least 12, at least 13, at least 14, at least 15, at least 16, at least 17, at least 18, at least 19, at least 20, or at least 21 carbons in length. Alternatively, or in addition, the $R^1$ group is 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the $R^1$ group can have an $R^1$ group bounded by any two of the above endpoints. For example, the $R^1$ group can be 6-16 carbons in length, 10-14 carbons in length, or 12-18 carbons in length. In some embodiments, the fatty acid is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or $C_{26}$ fatty acid. In certain embodiments, the fatty acid is a $C_6$, $C_8$, $C_{10}$, $C_{12}$, $C_{13}$, $C_{14}$, $C_{15}$, $C_{16}$, $C_{17}$, or $C_{18}$ fatty acid. In one preferred embodiment, the fatty amide is a C14, C16, or C18 fatty alkanolamide. In another preferred embodiment, the fatty amide is a C14, C16, or C18 fatty amidoamine. In still another preferred embodiment, the fatty amide is a C8, C9, C10, C11, C12, C13, C14, C15, C16, C17, C18, C19 or C20 alkanolamide. In yet another preferred embodiment, the fatty amide is a C8, C9, C10, C11, C12, C13, C14, C15, C16, C17, C18, C19 or C20 amidoamine.

The $R^1$ group of a fatty acid can be a straight chain or a branched chain. Branched chains may have more than one point of branching and may include cyclic branches. In some embodiments, the branched fatty acid is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or $C_{26}$ branched fatty acid. In particular embodiments, the branched fatty acid is a $C_6$, $C_8$, $C_{10}$, $C_{12}$, $C_{13}$, $C_{14}$, $C_{15}$, $C_{16}$, $C_{17}$, or $C_{18}$ branched fatty acid. In certain embodiments, the hydroxyl group of the branched fatty acid is in the primary ($C_1$) position.

In certain embodiments, the branched fatty acid is an iso-fatty acid or an anteiso-fatty acid. In exemplary embodiments, the branched fatty acid is selected from iso-$C_{7:0}$, iso-$C_{8:0}$, iso-$C_{9:0}$, iso-$C_{10:0}$, iso-$C_{11:0}$, iso-$C_{12:0}$, iso-$C_{13:0}$, iso-$C_{14:0}$, iso-$C_{15:0}$, iso-$C_{16:0}$, iso-$C_{17:0}$, iso-$C_{18:0}$, iso-$C_{19:0}$, anteiso-$C_{7:0}$, anteiso-$C_{8:0}$, anteiso-$C_{9:0}$, anteiso-$C_{10:0}$, anteiso-$C_{11:0}$, anteiso-$C_{12:0}$, anteiso-$C_{13:0}$, anteiso-$C_{14:0}$, anteiso-$C_{15:0}$, anteiso-$C_{16:0}$, anteiso-$C_{17:0}$, anteiso-$C_{18:0}$, and anteiso-$C_{19:0}$ branched fatty acid.

The $R^1$ group of a branched or unbranched fatty acid can be saturated or unsaturated. If unsaturated, the $R^1$ group can have one or more than one point of unsaturation. In some embodiments, the unsaturated fatty acid is a monounsaturated fatty acid. In certain embodiments, the unsaturated fatty acid is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or C26:1 unsaturated fatty acid. In other embodiments, the unsaturated fatty acid is a C10:1, C12:1, C14:1, C16:1, or C18:1 unsaturated fatty acid. In yet other embodiments, the unsaturated fatty acid is unsaturated at the omega-7 position. In certain embodiments, the unsaturated fatty acid comprises a cis double bond.

The primary amine can be any primary amine capable of serving as a substrate for PPS having the formula $R^2NH_2$, wherein $R^2$ represents a substituted or unsubstituted alkyl, substituted or unsubstituted heteroalkyl, substituted or unsubstituted alkenyl, or substituted or unsubstituted heteroalkenyl chain. In certain embodiments, $R^2$ is substituted with a hydroxyl group, and the fatty amide may be referred to as an "alkanolamide" or a "fatty alkanolamide." In other embodiments, $R^2$ contains an amino group, and the fatty amide may be referred to as an "amidoamine" or a "fatty amidoamine."

$R^2$ can comprise between 1 and 12 carbon atoms. In certain embodiments, $R^2$ comprises at least 2, at least 3, at least 4, at least 5, at least 6, or at least 7 carbons. Alternatively, or in addition, $R^2$ comprises 12 or less, 11 or less, 10 or less, 9 or less, 8 or less, 7 or less, 6 or less, 5 or less, or 4 or less carbons. Thus, the $R^2$ group can comprise carbons bounded by any two of the above endpoints. For example, the $R^2$ group can comprise 2-8 carbons, 4-10 carbons, or 3-6 carbons. In some embodiments, the $R^2$ group contains 3, 4, 5, or 6 carbon atoms.

The $R^2$ group of a primary amine can be a straight chain or a branched chain. Branched chains may have more than one point of branching and may include cyclic branches.

The term "alkyl," by itself or as part of another substituent means, unless otherwise stated, a straight chain or branched chain, or cyclic hydrocarbon radical, or combination thereof. This definition also applies wherever "alkyl" occurs as part of a group, such as, e.g., in hydroxyalkyl, haloalkyl, aminoalkyl, alkylamino, dialkylamino, etc.

The term "alkenyl," by itself or as part of another substituent means, unless otherwise stated, a straight chain or branched chain, or cyclic hydrocarbon radical, or combination thereof, containing, for example, about 2 to about 12 carbon atoms and containing at least one carbon-carbon double bond.

The terms "heteroalkyl" and "heteroalkenyl" refer to, unless otherwise stated, a straight or branched chain, or cyclic hydrocarbon radical, or combinations thereof, consisting of the stated number of carbon atoms and at least one heteroatom selected from the group consisting of O, N, Si, and S, and wherein the nitrogen and sulfur atoms may optionally be oxidized, and the nitrogen heteroatom may optionally be quaternized. The heteroatom(s) O, N, Si, and S may be placed at any interior position of the heteroalkyl or heteroalkenyl group. Exemplary heteroalkyl groups for the $R^2$ group include, but are not limited to, —$CH_2$—$CH_2$—OH, —$CH_2$—$CH_2$—O—$CH_3$, —$CH_2$—CHOH—$CH_3$, —$CH_2$—$CH_2$—$CH_2$—O—$CH_3$, —$CH_2$—$CH_2$—$CH_2$—N (CH₃)₂, CH₂—CH₂—CH₂—NH—CH₂—CH₃, —CH₂—CH₂—CH₂—NH—CH₂—CH₂—OH, —CH—(CH₂—OH)₂, and —Si(CH₃)₃. Up to two heteroatoms may be consecutive, such as, for example, —CH₂—CH₂—O—Si(CH₃)₃.

The terms alkyl, heteroalkyl, alkenyl, and heteroalkenyl are meant to include both substituted and unsubstituted forms of the indicated radical. Exemplary substituents for the alkyl, heteroalkyl, alkenyl, and heteroalkenyl radicals of the R² group can be one or more of a variety of groups selected from, but not limited to, —OR', =O, =NR', =N—OR', —NR'R", —SR', -halogen, —SiR'R"R'", —OC(O)R', —C(O)R', —CO₂R', —CN and —NO₂ in a number ranging from zero to (2m'+1), where m' is the total number of carbon atoms in such radical. Each of R', R", and R'" independently refers to hydrogen, unsubstituted or substituted alkyl, unsubstituted or substituted heteroalkyl, unsubstituted or substituted alkenyl, unsubstituted or substituted heteroalkenyl, alkoxy or thioalkoxy groups, or arylalkyl groups.

In some embodiments, the substituent for the R² group is —OH. In certain embodiments, the R² group is a polyhydroxy alkyl or a polyhydroxy heteroalkyl moiety containing 2, 3, or 4 hydroxyl groups.

The alkyl, heteroalkyl, alkenyl, or heteroalkenyl chain of the R² group also can be interrupted with a polyethylene oxide moiety. In certain embodiments, the R² group contains a polyethylene oxide moiety comprising 2 or more, 3 or more, 4 or more, 5 or more, or 6 or more, or 7 or more ethylene oxide moieties. In other embodiments, the R² group contains a polyethylene oxide moiety comprising 12 or less, 11 or less, 10 or less, 9 or less, 8 or less, 7 or less, 6 or less, or 5 or less ethylene oxide moieties. Thus, the R² group can contain a polyethylene oxide moiety having a number of ethylene oxide moieties bounded by any two of the above endpoints. For example, the R² group can contain a polyethylene oxide moiety having 2-10, 4-8, or 3-5 ethylene oxide moieties.

The primary amine may be produced in the microorganism from a fermentable carbon source. For example, monoethanolamine can be generated in vivo from serine by the action of serine decarboxylase (SDC) (Rontein et al. (2001) *J. Biol. Chem.* 276 (38):35523-35529). In some embodiments, the microorganism expresses an endogenous SDC polypeptide. In other embodiments, the microorganism is engineered to overexpress a SDC polypeptide.

Putrescine (1,4-diaminobutane) can be generated in vivo from arginine by the actions of arginine decarboxylase (ADC) and agmatine ureohydrolase (AUH), which convert arginine to agmatine, and agmatine to putrescine, respectively (Moore et al. (1990) *J. Bacteriol* 172(8): 4631-4640). In some embodiments, the microorganism expresses endogenous ADC and AUH polypeptides. In other embodiments, the microorganism is engineered to overexpress an ADC polypeptide, an AUH polypeptide, or ADC and AUH polypeptides. In certain embodiments, the ADC is encoded by the speA gene from *E. coli* MG1655 (GenBank Accession No. NC_000913).

The primary amine can also be provided to the microorganism exogenously.

Exemplary primary amines suitable for use in the disclosure include, but are not limited to, ethanolamine (monoethanolamine), 3-dimethylamino-1-propylamine, (±)-1-amino-2-propanol, 2-methoxyethylamine, 3-amino-1-propanol, 2-amino-1-3-propanediol, 3-methoxypropylamine, N-(2-hydroxyethyl)ethylenediamine, butylamine, 1,4-diaminobutane, and combinations thereof. In certain embodiments, the primary amine is 3-dimethylamino-1-propylamine.

The nucleic acid suitable for use in the recombinant microorganisms and methods of the disclosure can be any nucleic acid having a sequence which encodes a polypeptide capable of converting a primary amine and an acyl thioester to a fatty amide when the nucleic acid is expressed and the microorganism is cultured in the presence of a carbon source.

In one embodiment, the polypeptide is a PPS polypeptide. In certain embodiments, the PPS polypeptide comprises, consists essentially of, or consists of the amino acid sequence of SEQ ID NO: 1, i.e., the amino acid sequence of AAV33349. In some embodiments, the PPS polypeptide is encoded by a nucleic acid sequence comprising the nucleic acid sequence of SEQ ID NO: 2. In other embodiments, the PPS polypeptide is a homologue of the PPS polypeptide having the amino acid sequence of SEQ ID NO: 1. The PPS polypeptide preferably comprises, consists essentially of, or consists of an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to the amino acid sequence of SEQ ID NO: 1.

In other embodiments, the polypeptide is a N-(4-amino-2-hydroxylbutyl)tetradecanamide synthase (AhtS) polypeptide. In certain embodiments, the AhtS polypeptide comprises, consists essentially of, or consists of the amino acid sequence of SEQ ID NO: 3, i.e., the amino acid sequence of GenBank Accession No. ACX33975. In some embodiments, the AhtS polypeptide is encoded by a nucleic acid sequence comprising the nucleic acid sequence of SEQ ID NO: 22. In other embodiments, the AhtS polypeptide is a homologue of the AhtS polypeptide having the amino acid sequence of SEQ ID NO: 3. The AhtS polypeptide preferably comprises, consists essentially of, or consists of an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to the amino acid sequence of SEQ ID NO: 3.

In certain embodiments, the polypeptide that catalyzes the conversion of a primary amine and an acyl thioester to a fatty amide is endogenous to the microorganism. In such embodiments, the recombinant microorganism is engineered to overexpress the endogenous polypeptide that catalyzes the conversion of a primary amine and an acyl thioester to a fatty amide.

In other embodiments, the polypeptide that catalyzes the conversion of a primary amine and an acyl thioester to a fatty amide is exogenous to the microorganism. In such embodiments, the recombinant microorganism is engineered to express the exogenous polypeptide such that it catalyzes the conversion of a primary amine and an acyl thioester to a fatty amide. For example, the exogenous nucleic acid encoding the exogenous polypeptide can be integrated into the microorganism through standard molecular biology procedures. Providing the microorganism with a carbon source will allow the microorganism to increase fatty amide production.

The terms "homolog," "homologue," and "homologous" as used herein refer to a polynucleotide or a polypeptide comprising a sequence that is at least about 70% homologous to the corresponding polynucleotide or polypeptide sequence. One of ordinary skill in the art is well aware of methods to determine homology between two or more sequences. For example, the comparison of sequences and determination of percent homology between two sequences can be accomplished using a mathematical algorithm, such as Basic Local Alignment Search Tool (BLAST) (Altschul et al. (1990) *J. Mol. Biol.* 215 (3): 403-410).

The term "polynucleotide" refers to a polymer of DNA or RNA, which can be single-stranded or double-stranded and which can contain non-natural or altered nucleotides. The terms "polynucleotide," "nucleic acid," and "nucleic acid molecule" are used herein interchangeably to refer to a polymeric form of nucleotides of any length, either ribonucleotides (RNA) or deoxyribonucleotides (DNA).

The terms "polypeptide" and "protein" refer to a polymer of amino acid residues. The term "recombinant polypeptide" refers to a polypeptide that is produced by recombinant DNA techniques, wherein generally DNA encoding the expressed protein or RNA is inserted into a suitable expression vector that is in turn used to transform a host cell to produce the polypeptide or RNA.

In the compositions and methods of the disclosure, the production of a desired fatty acid or acyl thioester derivative thereof can be enhanced by altering the expression of one or more genes involved in the regulation of fatty acid production, degradation and/or secretion in the recombinant microorganism.

In some embodiments, the recombinant microorganism comprises a nucleic acid sequence encoding a fatty acid biosynthetic polypeptide. As used herein, the term "fatty acid biosynthetic polypeptide" refers to any polypeptide involved in fatty acid biosynthesis. The fatty acid biosynthetic pathway in host cells uses the precursors acetyl-CoA and malonyl-CoA. The steps in this pathway are catalyzed by enzymes of the fatty acid biosynthesis (fab) and acetyl-CoA carboxylase (acc) gene families (see, e.g., Heath et al. (2001) *Prog. Lipid Res.* 40 (6):467-497). Acetyl-CoA is carboxylated by acetyl-CoA carboxylase (EC 6.4.1.2) to form malonyl-CoA. Acetyl-CoA carboxylase (EC 6.4.1.2) is a multi-subunit enzyme encoded by four separate genes (accA, accB, accC, and accD) in most prokaryotes. In some bacteria, such as *Corynebacterium glutamicum*, acetyl-CoA carboxylase includes two subunits, AccDA [YP_225123.1] and AccBC [YP_224991], encoded by accDA and accBC, respectively. Depending upon the desired fatty acid or fatty acid derivative product, specific fab and/or acc genes (or combinations thereof) may be overexpressed, modified, attenuated, or deleted in an engineered host cell.

In some embodiments, the nucleic acid sequence encoding a fatty acid biosynthetic polypeptide encodes accABCD. In other embodiments, the nucleic acid sequence encoding a fatty acid biosynthetic polypeptide encodes FabD, FabH, FabG, FabB, FabA, FabZ, FabF, FabI, or a functional homologue of Fab from another organism, such as FabV. Exemplary GenBank Accession numbers for the fatty acid biosynthetic polypeptides suitable for use in the compositions and methods of the disclosure include FabD (AAC74176), FabH (AAC74175), FabG (AAC74177), FabB (POA953), FabA (ACY27485.1), FabZ (ACY27493.1), FabF (AAC74179), and FabI (NP_415804).

In some embodiments, the recombinant microorganism comprises nucleic acid sequences encoding two or more (e.g., 3 or more, 4 or more) biosynthetic polypeptides (e.g., accABCD and FabD; FabD, FabH, and FabG; or FabI, FabG,H,D, FabA,B, and FabZ).

FadR is a transcription factor involved in fatty acid degradation and fatty acid biosynthesis pathways (Cronan et al. (1998) *Mol. Microbiol.* 29 (4):937-943). FadR is known to modulate the expression and/or activity of numerous genes, including fabA, fabB, iclR, fadA, fadB, fadD, fadE, fadI, fadJ, fadL, fadM, uspA, aceA, aceB, and aceK. Exemplary GenBank accession numbers for polypeptides encoded by the FadR target genes include fabA (NP_415474), fabB (BAA16180), (NP_418442), fadA (YP_026272.1), fadB (NP_418288.1), fadD (AP_002424), fadE (NP_414756.2), fadI (NP_416844.1), fadJ (NP_416843.1), fadL (AAC75404), fadM (NP_414977.1), uspA (AAC76520), aceA (AAC76985.1), aceB (AAC76984.1), and aceK (AAC76986.1).

In some embodiments, the recombinant microorganism includes a nucleic acid sequence encoding a fatty acid biosynthetic polypeptide, and the nucleic acid sequence encoding FadR. In certain embodiments, the nucleic acid sequence encodes FadR from *E. coli* MG1655 (NP_415705).

Thioesterases (EC 3.1.2.14 or EC 3.1.1.5) hydrolyze fatty acids from acyl-ACP thioesters. The chain length of an acyl thioester substrate can be selected for by modifying the expression of selected thioesterases. In certain embodiments, a host cell is engineered to express, overexpress, have attenuated expression, or not to express one or more selected thioesterases to increase the production of a preferred fatty acid derivative substrate. For example, $C_{10}$ fatty acids can be produced by expressing a thioesterase that has a preference for producing $C_{10}$ fatty acids and attenuating thioesterases that have a preference for producing fatty acids other than $C_{10}$ fatty acids (e.g., a thioesterase which prefers to produce $C_{14}$ fatty acids). This would result in a relatively homogeneous population of fatty acids that comprise 10 carbons. In other instances, $C_{14}$ fatty acids can be produced by attenuating endogenous thioesterases that produce non-$C_{14}$ fatty acids and expressing the thioesterases that have a preference for $C_{14}$-ACP. In some situations, $C_{12}$ fatty acids can be produced by expressing thioesterases that have a preference for $C_{12}$-ACP and attenuating thioesterases that preferentially produce non-$C_{12}$ fatty acids. Acetyl-CoA, malonyl-CoA, and fatty acid overproduction can be verified using methods known in the art, for example, by using radioactive precursors, HPLC, or GC-MS.

Non-limiting examples of thioesterase genes (and corresponding GenBank Accession number(s)) whose expression can be altered in the compositions and methods of the disclosure include tesA without leader sequence ('tesA) from *E. coli* (AAC73596), tesB from *E. coli* (AAC73555), fatB from *Umbellularia california* (Q41635, AAA34215), fatB2 from *Cuphea* hookeriana (AAC49269), fatB3 from *Cuphea hookeriana* (Q39513; AAC72881), fatB from *Cinnamonum camphorum* (Q39473, AAC49151), fatB [M 141T] from *Arabidopsis thaliana* (CAA85388) (Mayer et al. (2007) *BMC Plant Biology* 7:1-11), fatA from *Arabidopsis thaliana* (NP 189147; NP 193041), fatA from *Bradyrhiizobium japonicum* (CAC39106), fatA from *Cuphea hookeriana* (AAC72883), and fatA1 from *Helianthus annus* (AAL79361).

In certain embodiments, the recombinant microorganism includes a nucleic acid sequence encoding a thioesterase, and the nucleic acid sequence is 'tesA from *E. coli* MG1655 (AAC73596).

Acyl-CoA synthases (EC 2.3.1.86) activate fatty acids by catalyzing the formation of acyl-CoA thioesters. Non-limiting examples of acyl-CoA synthase genes whose expression can be altered in the compositions and methods of the disclosure include fadD, fadK, BH3103, yhfL, Pfl-4354, EAV15023, fadD1, fadD2, RPC_4074, fadDD35, fadDD22, faa3p or the gene encoding the protein ZP_01644857. Specific examples of acyl-CoA synthase genes include fadDD35 from *M. tuberculosis* H37Rv [NP_217021], fadDD22 from *M. tuberculosis* H37Rv [NP_217464], fadD from *E. coli* [NP_416319], fadK from *E. coli* [YP_416216], fadD from *Acinetobacter* sp. ADP1 [YP_045024], fadD from *Haemophilus influenza* RdkW20 [NP_438551], fadD from *Rhodopseudomonas palustris* Bis B 18 [YP_533919], BH3101 from *Bacillus halodurans* C-125 [NP_243969], Pfl-4354 from *Pseudomonas fluorescens* Pfo-1 [YP_350082], EAV15023 from *Comamonas testosterone* KF-1 [ZP_01520072], yhfL from *B. subtilis* [NP_388908], fadD1 from *P. aeruginosa* PAO1 [NP_251989], fadD1 from *Ralstonia solanacearum* GM1 1000 [NP_520978], fadD2 from *P. aeruginosa* PAO1 [NP_251990], the gene encoding the protein ZP_01644857 from *Stenotrophomonas maltophilia* R551-3, faa3p from *Saccharomyces cerevisiae* [NP_012257], faalp from *Saccharomyces cerevisiae* [NP_014962], lcfA from *Bacillus subtilis* [CAA99571], and those described in Shockey et al. (2002) *Plant. Physiol.* 129:1710-1722); Caviglia et al. (2004) *J. Biol. Chem.* 279: 1163-1169); Knoll et al. (1994) *J. Biol. Chem.* 269(23): 16348-56); Johnson et al. (1994) *J. Biol. Chem.* 269:18037-18046); and Black et al. (1992) *J. Biol. Chem.* 267:25513-25520).

In some embodiments, the recombinant microorganism comprises a nucleic acid sequence encoding an acyl-CoA synthase polypeptide, and the acyl-CoA synthase polypeptide is FadD from *E. coli* MG1655 [NP_416319].

The recombinant microorganism can comprise nucleic acids encoding any combination of fatty acid biosynthetic polypeptides, thioesterase polypeptides, and acyl-CoA synthase polypeptides. In certain embodiments, the microorganism comprises a nucleic acid sequence encoding a thioesterase polypeptide and a nucleic acid sequence encoding an acyl-CoA synthase polypeptide.

One of ordinary skill in the art will understand that, depending upon the purpose (e.g., desired fatty acid or acyl thioester derivative thereof), specific genes (or combinations of genes) involved in fatty acid metabolism may be overexpressed, modified, attenuated, or deleted in a recombinant microorganism engineered to comprise a nucleic acid sequence encoding a polypeptide capable of catalyzing the conversion of a primary amine and an acyl thioester to a fatty amide. Additional examples of genes involved in fatty acid metabolism suitable for use in the disclosure are described, for example, in U.S. Patent Application Publication 2011/0162259, which is incorporated in its entirety by reference herein.

In some embodiments, the polypeptide is a fragment of any of the polypeptides described herein. The term "fragment" refers to a shorter portion of a full-length polypeptide or protein ranging in size from four amino acid residues to the entire amino acid sequence minus one amino acid residue. In certain embodiments of the invention, a fragment refers to the entire amino acid sequence of a domain of a polypeptide or protein (e.g., a substrate binding domain or a catalytic domain).

In some embodiments, the polypeptide is a mutant or a variant of any of the polypeptides described herein. The terms "mutant" and "variant" as used herein refer to a polypeptide having an amino acid sequence that differs from a wild-type polypeptide by at least one amino acid. For example, the mutant can comprise one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the mutant polypeptide has about 1, 2, 3, 4, 5, 6, 7, 8, 9, 10, 15, 20, 30, 40, 50, 60, 70, 80, 90, 100, or more amino acid substitutions, additions, insertions, or deletions.

Preferred fragments or mutants of a polypeptide retain some or all of the biological function (e.g., enzymatic activity) of the corresponding wild-type polypeptide. In some embodiments, the fragment or mutant retains at least about 75%, at least about 80%, at least about 90%, at least about 95%, or at least about 98% or more of the biological function of the corresponding wild-type polypeptide. In other embodiments, the fragment or mutant retains about 100% of the biological function of the corresponding wild-type polypeptide. Guidance in determining which amino acid residues may be substituted, inserted, or deleted without affecting biological activity may be found using computer programs well known in the art, for example, LASERGENE™ software (DNASTAR, Inc., Madison, Wis.).

In yet other embodiments, a fragment or mutant has an "increased level of activity." By "increased level of activity" is meant that a polypeptide has a higher level of biochemical or biological function (e.g., DNA binding or enzymatic activity) in an engineered cell as compared to its level of biochemical and/or biological function in a corresponding wild-type host cell under the same conditions. The degree of enhanced activity can be about 10% or more, about 20% or more, about 50% or more, about 75% or more, about 100% or more, about 200% or more, about 500% or more, about 1000% or more, or any range therein.

In some embodiments, a polypeptide or polynucleotide having an altered or modified level of expression is "overexpressed" or has an "increased level of expression." As used herein, "overexpress" and "increasing the level of expression" mean to express or cause to be expressed a polynucleotide or polypeptide in an engineered cell at a greater concentration than is normally expressed in a corresponding wild-type cell under the same conditions. For example, a polypeptide can be "overexpressed" in an engineered cell when the polypeptide is present in a greater concentration in the engineered cell as compared to its concentration in a non-engineered host cell of the same species under the same conditions.

In other embodiments, a polypeptide or polynucleotide having altered level of expression is "attenuated" or has a "decreased level of expression." As used herein, "attenuate" and "decreasing the level of expression" mean to express or cause to be expressed a polynucleotide or polypeptide in an engineered cell at a lesser concentration than is normally expressed in a corresponding wild-type cell under the same conditions.

The degree of overexpression or attenuation can be 1.5-fold or more, e.g., 2-fold or more, 3-fold or more, 5-fold or more, 10-fold or more, or 15-fold or more. Alternatively, or in addition, the degree of overexpression or attenuation can be 500-fold or less, e.g., 100-fold or less, 50-fold or less, 25-fold or less, or 20-fold or less. Thus, the degree of overexpression or attenuation can be bounded by any two of the above endpoints. For example, the degree of overexpression or attenuation can be 1.5-500-fold, 2-50-fold, 10-25-fold, or 15-20-fold.

A polynucleotide or polypeptide can be attenuated using methods known in the art. In some embodiments, the expression of a gene or polypeptide encoded by the gene is attenuated by mutating the regulatory polynucleotide sequences which control expression of the gene. In other embodiments, the expression of a gene or polypeptide encoded by the gene is attenuated by overexpressing a repressor protein, or by providing an exogenous regulatory element that activates a repressor protein. In still yet other embodiments, DNA- or RNA-based gene silencing methods are used to attenuate the expression of a gene or polynucleotide. In some embodiments, the expression of a gene or polypeptide is completely attenuated, e.g., by deleting all or a portion of the polynucleotide sequence of a gene.

A polynucleotide or polypeptide can be overexpressed using methods known in the art. In some embodiments, overexpression of a polypeptide is achieved by the use of an exogenous regulatory element. The term "exogenous regulatory element" generally refers to a regulatory element originating outside of the host cell. However, in certain embodiments, the term "exogenous regulatory element" can refer to a regulatory element derived from the host cell whose function is replicated or usurped for the purpose of controlling the expression of an endogenous polypeptide. For example, if the recombinant microorganism is an *E. coli* cell which comprises a nucleic acid sequence encoding a fatty acid biosynthetic polypeptide, and the fatty acid biosynthetic polypeptide is FadR encoded by an endogenous fadR gene, then expression of the endogenous fadR can be controlled by a promoter derived from another *E. coli* gene.

In some embodiments, the exogenous regulatory element is a chemical compound, such as a small molecule. As used herein, the term "small molecule" refers to a substance or compound having a molecular weight of less than about 1,000 g/mol.

In some embodiments, the exogenous regulatory element which controls the expression of a nucleic acid sequence is an expression control sequence which is operably linked to the nucleic acid sequence. Expression control sequences are known in the art and include, for example, promoters, enhancers, polyadenylation signals, transcription terminators, internal ribosome entry sites (IRES), ribosome binding sites (RBS), and the like, that provide for the expression of the nucleic acid sequence in a host cell. Expression control sequences interact specifically with cellular proteins involved in transcription (Maniatis et al. (1987) *Science* 236:1237-1245). Exemplary expression control sequences are described in, for example, Goeddel, *Gene Expression Technology: Methods in Enzymology*, Vol. 185, Academic Press, San Diego, Calif. (1990).

By "operably linked" is meant that a nucleic acid sequence and an expression control sequence(s) are connected in such a way as to permit gene expression when the appropriate molecules (e.g., transcriptional activator proteins) are bound to the expression control sequence(s). Operably linked promoters are located upstream of the selected nucleic acid sequence in terms of the direction of transcription and translation. Operably linked enhancers can be located upstream, within, or downstream of the selected nucleic acid sequence.

In some embodiments, the nucleic acid sequence is provided to the host cell by way of a recombinant vector, which comprises a promoter operably linked to the polynucleotide sequence. In certain embodiments, the promoter is an inducible, a constitutive, or an organelle specific promoter. In certain embodiments, the expression control sequence is operably linked to an endogenous nucleic acid sequence by integration of the expression control sequence into the genome of a host cell by homologous recombination using methods known in the art (e.g., Datsenko et al. (2000) *Proc. Natl. Acad. Sci. U.S.A.* 97 (12): 6640-6645).

As used herein, the term "vector" refers to a nucleic acid molecule capable of transporting another nucleic acid sequence to which it has been linked. One type of useful vector is an episome (i.e., a nucleic acid capable of extrachromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. However, also included are such other forms of expression vectors that serve equivalent functions and that become known in the art subsequently hereto.

In some embodiments, the recombinant vector comprises at least one sequence selected from the group consisting of (a) an expression control sequence operatively coupled to the nucleic acid sequence; (b) a selection marker operatively coupled to the nucleic acid sequence; and (c) a targeting sequence operatively coupled to the nucleic acid sequence.

It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

Suitable expression systems for both prokaryotic and eukaryotic cells are well known in the art; see, e.g., Sambrook et al., "Molecular Cloning: A Laboratory Manual," second edition, Cold Spring Harbor Laboratory (1989). Examples of inducible, non-fusion *E. coli* expression vectors include pTrc (Amann et al. (1988) *Gene* 69:301-315) and PET 11d (Studier et al., Gene Expression Technology Methods in Enzymology 185, Academic Press, San Diego, Calif., pp. 60-89 (1990)). In certain embodiments, a polynucleotide sequence of the disclosure is operably linked to a promoter derived from bacteriophage T5. Examples of vectors for expression in yeast include pYepSec1 (Baldari et al. (1987) *EMBO J.* 6:229-234), pMFa (Kurjan et al. (1982) *Cell* 30:933-943), pJRY88 (Schultz et al. (1987) *Gene* 54:113-123), pYES2 (Invitrogen Corp., San Diego, Calif.), and picZ (Invitrogen Corp., San Diego, Calif.).

Vectors can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells as well as methods to select for cells which have taken up the vector can be found in, for example, Sambrook et al. (supra).

A "recombinant microorganism" is a host cell used to produce a product described herein (e.g., a fatty amide). A recombinant microorganism, also referred to herein as a "recombinant host cell," an "engineered microorganism," or an "engineered host cell," is a host cell wherein the expression of one or more nucleic acids or polypeptides are altered or modified as compared to their expression in a corresponding wild-type host cell under the same conditions. In any of the aspects of the disclosure described herein, the host cell can include, but is not limited to, a bacteria cell, a cyanobacteria cell, an algae cell, and a fungus cell (e.g., a filamentous fungus cell or a yeast cell).

In some embodiments, the host cell is a Gram-positive bacterial cell. In other embodiments, the host cell is a Gram-negative bacterial cell.

In some embodiments, the host cell is selected from the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Synechococcus, Yarrowia,* or *Streptomyces*.

In certain embodiments, the host cell is a *Saccharomyces cerevisiae, Candida lipolytica, Escherichia coli, Arthrobacter, Rhodotorula glutinins, Acinetobacter, Candida lipolytica, Botryococcus braunii, Vibrio furnissii, Micrococcus leuteus, Stenotrophomonas maltophilia, Bacillus subtilis, Bacillus lichenoformis, Psuedomonus putida, Psuedomonas florescens, Streptomyces coelicolor, Prototheca moriformis, Prototheca krugani, Prototheca stagnora, Prototheca zopfii,* or *Chorella protothecoide* cell.

In some embodiments, the host cell is an *Arthrobacter* AK 19, *Acinetobacter* sp. strain M-1, *E. coli* B, *E. coli* C, *E. coli* K, or *E. coli* W cell.

In other embodiments, the host cell is a *Bacillus lentus* cell, a *Bacillus brevis* cell, a *Bacillus stearothermophilus* cell, a *Bacillus lichenformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, or a *Bacillus amyloliquefaciens* cell.

In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell.

In yet other embodiments, the host cell is a *Streptomyces lividans* cell or a *Streptomyces murinus* cell.

In yet other embodiments, the host cell is an *Actinomycetes* cell.

In other embodiments, the host cell is a cell from an eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Avabidopsis thaliana, Panicum virgatum, Miscanthus giganteus, Zea mays, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridiuthermocellum, Penicillium chrysogenum, Pichia pastoris, Schizosaccharomyces pombe, Pseudomonasjluorescens,* or *Zymomonas mobilis*.

As used herein, the term "conditions permissive for the production" means any conditions that allow a host cell to produce a desired product, such as a fatty amide. Similarly, the term "conditions suitable for expression" means any conditions that allow a host cell to synthesize a polypeptide. Suitable conditions include, for example, fermentation conditions. Fermentation conditions can comprise many parameters, such as temperature ranges, levels of aeration, and media composition. Each of these conditions, individually and in combination, allows the host cell to grow. Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source.

As used herein, the phrase "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, and turanose; cellulosic material and variants such as methyl cellulose and sodium carboxymethyl cellulose; saturated or unsaturated fatty acid esters, succinate, lactate, and acetate; alcohols, such as ethanol, methanol, and glycerol, or mixtures thereof. The carbon source can also be a product of photosynthesis, such as glucose. In certain preferred embodiments, the carbon source is biomass. In other preferred embodiments, the carbon source is glucose.

The term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a biofuel. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, food leftovers, and glycerol. The term "biomass" also can refer to sources of carbon, such as carbohydrates (e.g., monosaccharides, disaccharides, or polysaccharides).

To determine if conditions are sufficient to allow production of a product or expression of a polypeptide, a host cell can be cultured, for example, for about 4, 8, 12, 24, 36, 48, 72, or more hours. During and/or after culturing, samples can be obtained and analyzed to determine if the conditions allow production or expression. For example, the host cells in the sample or the medium in which the host cells were grown can be tested for the presence of a desired product. When testing for the presence of a fatty amide, assays, such as, but not limited to, MS, thin layer chromatography (TLC), high-performance liquid chromatography (HPLC), liquid chromatography (LC), GC coupled with a flame ionization detector (FID), GC-MS, and LC-MS can be used. When testing for the expression of a polypeptide, techniques such as, but not limited to, Western blotting and dot blotting may be used.

In the methods of the invention, the production and isolation of fatty amides can be enhanced by optimizing fermentation conditions. In some embodiments, fermentation conditions are optimized to increase the percentage of the carbon source that is converted to hydrocarbon products. During normal cellular lifecycles, carbon is used in cellular functions, such as producing lipids, saccharides, proteins, organic acids, and nucleic acids. Reducing the amount of carbon necessary for growth-related activities can increase the efficiency of carbon source conversion to product. This can be achieved by, for example, first growing host cells to a desired density (for example, a density achieved at the peak of the log phase of growth). At such a point, replication checkpoint genes can be harnessed to stop the growth of cells. Specifically, quorum sensing mechanisms (reviewed in Camilli et al. (2006) *Science* 311:1113; Venturi (2006) *FEMS Microbiol. Rev.* 30:274-291; and Reading et al. (2006) *FEMS Microbiol. Lett.* 254:1-11) can be used to activate checkpoint genes, such as p53, p21, or other checkpoint genes.

Genes that can be activated to stop cell replication and growth in *E. coli* include umuDC genes. The overexpression of umuDC genes stops the progression from stationary phase to exponential growth (Murli et al. (2000) *J. Bacteriol.* 182:1127-1135). UmuC is a DNA polymerase that can carry out translesion synthesis over non-coding lesions which commonly result from ultraviolet (UV) and chemical mutagenesis. The umuDC gene products are involved in the process of translesion synthesis and also serve as a DNA sequence damage checkpoint. The umuDC gene products include UmuC, UmuD, umuD', UmuD'$_2$C, UmuD'$_2$, and UmuD$_2$. Simultaneously, product-producing genes can be activated, thereby minimizing the need for replication and maintenance pathways to be used while a fatty amide or intermediate thereof is being made. Host cells can also be engineered to express umuC and umuD from *E. coli* in pBAD24 under the prpBCDE promoter system through de novo synthesis of this gene with the appropriate end-product production genes.

The host cell can be additionally engineered to express a recombinant cellulosome, which can allow the host cell to use cellulosic material as a carbon source. Exemplary cellulosomes suitable for use in the methods of the disclosure include, e.g., the cellulosomes described in International Patent Application Publication WO 2008/100251. The host cell also can be engineered to assimilate carbon efficiently and use cellulosic materials as carbon sources according to methods described in U.S. Pat. Nos. 5,000,000; 5,028,539; 5,424,202; 5,482,846; and 5,602,030. In addition, the host cell can be engineered to express an invertase so that sucrose can be used as a carbon source.

In some embodiments of the fermentation methods of the disclosure, the fermentation chamber encloses a fermentation that is undergoing a continuous reduction, thereby creating a stable reductive environment. The electron balance can be maintained by the release of carbon dioxide (in gaseous form). Efforts to augment the NAD/H and NADP/H balance can also facilitate in stabilizing the electron balance. The availability of intracellular NADPH can also be enhanced by engineering the host cell to express an NADH: NADPH transhydrogenase. The expression of one or more NADH:NADPH transhydrogenases converts the NADH produced in glycolysis to NADPH, which can enhance the production of fatty amides and intermediates thereof.

For small scale production, the engineered host cells can be grown in batches of, for example, about 100 mL, 500 mL, 1 L, 2 L, 5 L, or 10 L; fermented; and induced to express a desired nucleic acid sequence, such as a nucleic acid sequence encoding a PPS. For large scale production, the engineered host cells can be grown in batches of about 10 L, 100 L, 1000 L, 10,000 L, 100,000 L, 1,000,000 L or larger; fermented; and induced to express a desired nucleic acid sequence.

The fatty amides produced by the methods of disclosure generally are isolated from the host cell. The term "isolated" as used herein with respect to products, such as fatty amides, refers to products that are separated from cellular components, cell culture media, or chemical or synthetic precursors. The fatty amides produced by the methods described herein can be relatively immiscible in the fermentation broth, as well as in the cytoplasm. Therefore, the fatty amides and derivatives thereof can collect in an organic phase either intracellularly or extracellularly. The collection of the products in the organic phase can lessen the impact of the fatty amide on cellular function and can allow the host cell to produce more product.

In some embodiments, the fatty amides produced by the methods of disclosure are purified. As used herein, the term "purify," "purified," or "purification" means the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of a fatty amide in a sample. For example, when a fatty amide is produced in a host cell, the fatty amide can be purified by the removal of host cell proteins. After purification, the percentage of a fatty amide in the sample is increased.

As used herein, the terms "purify," "purified," and "purification" are relative terms which do not require absolute purity. Thus, for example, when a fatty amide is produced in host cells, a purified fatty amide is a fatty amide that is substantially separated from other cellular components (e.g., nucleic acids, polypeptides, lipids, carbohydrates, or other hydrocarbons).

Additionally, a purified fatty amide preparation is a fatty amide preparation in which the fatty amide is substantially free from contaminants, such as those that might be present following fermentation. In some embodiments, a fatty amide is purified when at least about 50% by weight of a sample is composed of the fatty amide. In other embodiments, a fatty amide is purified when at least about 60%, e.g., at least about 70%, at least about 80%, at least about 85%, at least about 90%, at least about 92%, by weight of a sample is composed of the fatty amide. Alternatively, or in addition, a fatty amide is purified when less than about 100%, e.g., less than about 99%, less than about 98%, less than about 95%, less than about 90%, or less than about 80%, by weight of a sample is composed of the fatty amide. Thus, a purified fatty amide can have a purity level bounded by any two of the above endpoints. For example, a fatty amide can be purified when at least about 80%-95%, at least about 85%-99%, or at least about 90%-98% of a sample is composed of the fatty amide.

The fatty amide may be present in the extracellular environment, or it may be isolated from the extracellular environment of the host cell. In certain embodiments, a fatty amide is secreted from the host cell. In other embodiments, a fatty amide is transported into the extracellular environment. In yet other embodiments, the fatty amide is passively transported into the extracellular environment. A fatty amide can be isolated from a host cell using methods known in the art, such as those disclosed in International Patent Application Publications WO 2010/042664 and WO 2010/062480.

The methods described herein can result in the production of homogeneous compounds wherein at least about 60%, at least about 70%, at least about 80%, at least about 90%, or at least about 95%, of the fatty amides produced will have fatty chains that vary by less than 6 carbons, less than 5 carbons, less than 4 carbons, less than 3 carbons, or less than about 2 carbons. Alternatively, or in addition, the methods described herein can result in the production of homogeneous compounds wherein less than about 98%, less than about 95%, less than about 90%, less than about 80%, or less than about 70% of the fatty amides produced will have fatty chains that vary by less than 6 carbons, less than 5 carbons, less than 4 carbons, less than 3 carbons, or less than about 2 carbons. Thus, the fatty amides can have a degree of homogeneity bounded by any two of the above endpoints. For example, the fatty amide can have a degree of homogeneity wherein about 70%-95%, about 80%-98%, or about 90%-95% of the fatty amides produced will have fatty chains that vary by less than 6 carbons, less than 5 carbons, less than 4 carbons, less than 3 carbons, or less than about 2 carbons. These compounds also can be produced with a relatively uniform degree of saturation.

As a result of the methods of the invention, one or more of the titer, yield, or productivity of the fatty amide produced by the recombinant microorganism engineered to comprise a nucleic acid sequence encoding a polypeptide that catalyzes the conversion of a primary amine and an acyl thioester to a fatty amide is increased relative to that of the corresponding wild-type microorganism.

The term "titer" refers to the quantity of fatty amide produced per unit volume of host cell culture. In any aspect of the compositions and methods described herein, a fatty amide is produced at a titer of 25 mg/L or more, 50 mg/L or more, 75 mg/L or more, 100 mg/L or more, 125 mg/L or more, 150 mg/L or more, 175 mg/L or more, 200 mg/L or more, 250 mg/L or more, 300 mg/L or more, 350 mg/L or more, 400 mg/L or more, 450 mg/L or more, 500 mg/L or more, 600 mg/L or more, 700 mg/L or more, 800 mg/L or more, 900 mg/L or more, or 1000 mg/L or more. Alternatively, or in addition, the fatty amide is produced at a titer of 2000 mg/L or less, 1900 mg/L or less, 1800 mg/L or less, 1700 mg/L or less, 1600 mg/L or less, 1500 mg/L or less, 1400 mg/L or less, 1300 mg/L or less, 1200 mg/L or less, 1100 mg/L or less, 1000 mg/L or less, 900 mg/L or less, 800 mg/L or less, 700 mg/L or less, 600 mg/L or less, 500 mg/L or less, 400 mg/L or less, 300 mg/L or less, or 200 mg/L or less. Thus, the fatty amide is produced at a titer bounded by any two of the above endpoints. For example, the fatty amide can be produced at a titer of 150-1000 mg/L, 200-500 mg/L, 500-1500 mg/L, or 300-1300 mg/L. In other embodiments, a fatty amide is produced at a titer of more than 2000 mg/L, more than 5000 mg/L, more than 10,000 mg/L, or higher, such as 50 g/L, 70 g/L, 100 g/L, 120 g/L, 150 g/L, or 200 g/L.

The term "yield" refers to the efficiency by which an input carbon source is converted to product (i.e., fatty amide) in a host cell. For oxygen-containing carbon sources (e.g., glucose and other carbohydrate based sources), the oxygen must be released in the form of carbon dioxide. Thus, for every two oxygen atoms released, a carbon atom is also released leading to a maximal theoretical metabolic efficiency of approximately 34% (w/w) (for fatty acid derived products). This figure, however, changes for other organic compounds and carbon sources. Typical yield reported in the literature are approximately less than 5%. Host cells engineered to produce fatty amides according to the methods of the disclosure can have a yield of about 3% or more, about 5% or more, about 10% or more, about 15% or more, about 18% or more, or about 20% or more. Alternatively, or in addition, the yield is about 30% or less, about 27% or less, about 25% or less, about 22% or less, about 20% or less, about 17% or less, about 13% or less, or about 10% or less. Thus, the yield can be bounded by any two of the above endpoints. For example, the yield of the fatty amide produced by the recombinant microorganism of the disclosure can be about 5% to about 25%, about 10% to about 25%, about 10% to about 22%, about 15% to about 27%, or about 18% to about 22%. In other embodiments, the yield is greater than 30%.

The term "productivity" refers to the quantity of fatty amide produced per unit volume of host cell culture per unit density of host cell culture. In any aspect of the compositions and methods described herein, the productivity of a fatty amide produced by a recombinant microorganism is about 3 mg/L/OD$_{600}$ or more, about 6 mg/L/OD$_{600}$ or more, about 9 mg/L/OD$_{600}$ or more, about 12 mg/L/OD$_{600}$ or more, about 15 mg/L/OD$_{600}$ or more, about 18 mg/L/OD$_{600}$ or more, or about 20 mg/L/OD$_{600}$ or more. Alternatively, or in addition, the productivity is about 50 mg/L/OD$_{600}$ or less, about 40 mg/L/OD$_{600}$ or less, about 30 mg/L/OD$_{600}$ or less, about 25 mg/L/OD$_{600}$ or less, about 20 mg/L/OD$_{600}$ or less, about 17 mg/L/OD$_{600}$ or less, or about 10 mg/L/OD$_{600}$ or less. Thus, the productivity can be bounded by any two of the above endpoints. For example, the productivity can be about 3 to about 30 mg/L/OD$_{600}$, about 6 to about 20 mg/L/OD$_{600}$, or about 15 to about 30 mg/L/OD$_{600}$.

The disclosure also provides a fatty amide produced by the recombinant microorganisms and methods described herein. A bioproduct (e.g., a fatty amide) produced by the recombinant microorganisms and methods of the disclosure can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588).

The ability to distinguish bioproducts from petroleum-based organic compounds is beneficial in tracking these materials in commerce. For example, organic compounds or chemicals comprising both biologically-based and petroleum-based carbon isotope profiles may be distinguished from organic compounds and chemicals made only of petroleum-based materials. Hence, the fatty amides prepared in accordance with the inventive methods may be followed in commerce on the basis of their unique carbon isotope profile.

Bioproducts can be distinguished from petroleum-based organic compounds by comparing the stable carbon isotope ratio ($^{13}C/^{12}C$) in each fuel. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway.

The $^{13}C$ measurement scale was originally defined by a zero set by Pee Dee Belemnite (PDB) limestone, where values are given in parts per thousand deviations from this material. The "$\delta^{13}C$" values are expressed in parts per thousand (per mil), abbreviated, ‰, and are calculated as follows:

$$\delta^{13}C(‰)=[(^{13}C/^{12}C)_{sample}-(^{13}C/^{12}C)_{standard}]/(^{13}C/^{12}C)_{standard}\times 1000$$

In some embodiments, a fatty amide produced according to the methods of the disclosure has a $\delta^{13}C$ of about −30 or greater, about −28 or greater, about −27 or greater, about −20 or greater, about −18 or greater, about −15 or greater, about −13 or greater, or about −10 or greater. Alternatively, or in addition, a fatty amide has a $\delta^{13}C$ of about −4 or less, about −5 or less, about −8 or less, about −10 or less, about −13 or less, about −15 or less, about −18 or less, or about −20 or less. Thus, the fatty amide can have a $\delta^{13}C$ bounded by any two of the above endpoints. For example, the fatty amide can have a $\delta^{13}C$ of about −30 to about −15, about −27 to about −19, about −25 to about −21, about −15 to about −5, about −13 to about −7, or about −13 to about −10. In some embodiments, the fatty amide can have a $\delta^{13}C$ of about −10, −11, −12, or −12.3. In other embodiments, the fatty amide has a $\delta^{13}C$ of about −15.4 or greater. In yet other embodiments, the fatty amide has a $\delta^{13}C$ of about −15.4 to about −10.9, or a $\delta^{13}C$ of about −13.92 to about −13.84.

Bioproducts can also be distinguished from petroleum-based organic compounds by comparing the amount of $^{14}C$ in each compound. Because $^{14}C$ has a nuclear half life of 5730 years, petroleum based fuels containing "older" carbon can be distinguished from bioproducts which contain "newer" carbon (see, e.g., Currie, "Source Apportionment of Atmospheric Particles", *Characterization of Environmental Particles*, J. Buffle and H. P. van Leeuwen, Eds., Vol. I of the IUPAC Environmental Analytical Chemistry Series, Lewis Publishers, Inc., pp. 3-74 (1992)).

$^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C. As used herein, "fraction of modern carbon" or $f_M$ has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

In some embodiments, a fatty amide produced according to the methods of the disclosure has a $f_M{}^{14}C$ of at least about 1, e.g., at least about 1.003, at least about 1.01, at least about 1.04, at least about 1.111, at least about 1.18, or at least about 1.124. Alternatively, or in addition, the fatty amide has an $f_M{}^{14}C$ of about 1.130 or less, e.g., about 1.124 or less, about 1.18 or less, about 1.111 or less, or about 1.04 or less. Thus, the fatty amide can have a $f_M{}^{14}C$ bounded by any two of the above endpoints. For example, the fatty amide can have a $f_M{}^{14}C$ of about 1.003 to about 1.124, a $f_M{}^{14}C$ of about 1.04 to about 1.18, or a $f_M{}^{14}C$ of about 1.111 to about 1.124.

Another measurement of $^{14}C$ is known as the percent of modem carbon, i.e., pMC. For an archaeologist or geologist using $^{14}C$ dates, AD 1950 equals "zero years old." This also represents 100 pMC. "Bomb carbon" in the atmosphere reached almost twice the normal level in 1963 at the peak of thermo-nuclear weapons testing. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum-based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum-based products, the measured pMC value for that material will reflect the proportions of the two component types. For example, a material derived 100% from present day soybeans would have a radiocarbon signature near 107.5 pMC. If that material was diluted 50% with petroleum-based products, the resulting mixture would have a radiocarbon signature of approximately 54 pMC.

A biologically-based carbon content is derived by assigning "100%" equal to 107.5 pMC and "0%" equal to 0 pMC. For example, a sample measuring 99 pMC will provide an equivalent biologically-based carbon content of 93%. This value is referred to as the mean biologically-based carbon result and assumes that all of the components within the analyzed material originated either from present day biological material or petroleum-based material.

In some embodiments, a fatty amide produced according to the methods of the disclosure has a pMC of at least about 50, at least about 60, at least about 70, at least about 75, at least about 80, at least about 85, at least about 90, at least about 95, at least about 96, at least about 97, or at least about 98. Alternatively, or in addition, the fatty amide has a pMC of about 108 or less, about 105 or less, about 102 or less, about 99 or less, about 96 or less, about 93 or less, about 90 or less, about 85 or less, or about 80 or less. Thus, the fatty amide can have a pMC bounded by any two of the above endpoints. For example, a fatty amide can have a pMC of about 50 to about 100; about 60 to about 105; about 70 to about 100; about 80 to about 105; about 85 to about 100; about 87 to about 98; or about 90 to about 95. In other embodiments, a fatty amide described herein has a pMC of about 90, about 91, about 92, about 93, about 94, or about 94.2.

A fatty amide produced by any of the recombinant microorganisms and methods described herein can be used directly as a surfactant or detergent per se, or the fatty amide can be formulated into a personal, pet, or household cleaning composition. Surfactant, detergent, and cleaning compositions and methods for the production thereof are well known to those of skill in the art, and are described in more detail in, e.g., U.S. Patent Application Publication 2011/0206630, which is incorporated in its entirety by reference herein.

Thus, the disclosure provides surfactant, detergent, and cleaning compositions comprising a fatty amide produced by any of the methods described herein. One of ordinary skill in the art will appreciate that, depending upon the intended purpose of the surfactant, detergent, or cleaning composition, different fatty amides can be produced and used. For example, when the fatty amides described herein are used as a feedstock for surfactant or detergent production, one of ordinary skill in the art will appreciate that the characteristics of the fatty amide feedstock will affect the characteristics of the surfactant or detergent composition produced. Hence, the characteristics of the surfactant or detergent composition can be selected for by producing particular fatty amides for use as a feedstock.

A fatty amide-based surfactant or detergent of the disclosure can be mixed with other surfactants and/or detergents well known in the art. The fatty amide can be present in the mixture in an amount of 10 weight percent (wt. %) or more, 15 wt. % or more, 20 wt. % or more, 30 wt. % or more, 40 wt. % or more, 50 wt. % or more, 60 wt. % or more, or 70 wt. % or more, based on the total weight of the mixture. Alternatively, or in addition, the fatty amide can be present in the mixture in an amount of 95 wt. % or less, 90 wt. % or less, 80 wt. % or less, 70 wt. % or less, 60 wt. % or less, 50 wt. % or less, or 40 wt. % or less, based on the total weight of the mixture. Thus, the fatty amide can be present in the mixture in an amount bounded by any two of the above endpoints. For example, the fatty amide can be present in the mixture in an amount of 15-40%, 30-90%, 50-95%, or 40-50%.

A fatty amide-based surfactant can be formulated into a cleaning composition to impart detergency and cleaning power to the cleaning composition. The fatty amide can be present in the cleaning composition in an amount of 0.001 wt. % or more, 0.1 wt. % or more, 1 wt. % or more, 10 wt. % or more, 20 wt. % or more, or 40 wt. % or more, based on the total weight of the cleaning composition. Alternatively, or in addition, the fatty amide can be present in the cleaning composition in an amount of 60 wt. % or less, 50 wt. % or less, 40 wt. % or less, 30 wt. % or less, 15 wt. % or less, or 5 wt. % or less, based on the total weight of the cleaning composition. Thus, the fatty amide can be present in the cleaning composition in an amount bounded by any two of the above endpoints. For example, the fatty amide can be formulated into a cleaning composition in an amount of 0.1-10 wt. %, 10-15 wt. %, 20-40 wt. %, or 0.001-5 wt. %.

A cleaning composition of the disclosure can be in solid form, such as a tablet, granule, powder, or compact. The cleaning composition also can be in liquid form, such as a fluid, gel, paste, emulsion, or concentrate.

In certain embodiments, the cleaning composition of the disclosure is a liquid or solid laundry detergent composition. In some embodiments, the cleaning composition is a hard surface cleaning composition, wherein the hard surface cleaning composition preferably impregnates a nonwoven substrate. As used herein, "impregnate" means that the hard surface cleaning composition is placed in contact with a nonwoven substrate such that at least a portion of the nonwoven substrate is penetrated by the hard surface cleaning composition. For example, the hard surface cleaning composition preferably saturates the nonwoven substrate. In other embodiments, the cleaning composition of the disclosure is a car care composition, which is useful for cleaning various surfaces such as hard wood, tile, ceramic, plastic, leather, metal, and/or glass. In some embodiments, the cleaning composition is a dishwashing composition, such as, for example, a liquid hand dishwashing composition, a solid automatic dishwashing composition, a liquid automatic dishwashing composition, and a tab/unit dose form automatic dishwashing composition.

In other embodiments, the cleaning composition can be used in industrial environments for cleaning various equipment and machinery, and for use in oil drilling operations. For example, the cleaning composition of the disclosure can be particularly suited in environments wherein it comes into contact with free hardness and in compositions that require hardness tolerant surfactant systems, such as when used to aid oil drilling.

In some embodiments, a fatty amide produced by any of the recombinant microorganisms and methods of the disclosure is formulated into personal or pet care composition such as a shampoo, body wash, face wash, or liquid or solid soap.

A cleaning composition containing a fatty amide produced by any of the recombinant microorganisms and methods of the disclosure can comprise other cleaning adjuncts which are well known to those of skill in the art. Common cleaning adjuncts applicable to most cleaning compositions, including household cleaning compositions, personal care compositions, and the like, include solvents, solubilizing agents, carriers, builders, enzymes, polymers, suds boosters, suds suppressors (antifoam), dyes, fillers, germicides, hydrotropes, anti-oxidants, perfumes, pro-perfumes, enzyme stabilizing agents, pigments, and the like. In some embodiments, the cleaning composition is a liquid cleaning composition, wherein the composition comprises one or more selected from solvents, chelating agents, dispersants, and water. In other embodiments, the cleaning composition is a solid, wherein the composition further comprises, for example, an inorganic filler salt. Inorganic filler salts are conventional ingredients of solid cleaning compositions, present in substantial amounts, varying from, for example, about 10 wt. % to about 35 wt. %. Suitable filler salts include, for example, alkali and alkaline-earth metal salts of sulfates and chlorides. An exemplary filler salt is sodium sulfate.

Household cleaning compositions (e.g., laundry detergents and household surface cleaners) can comprise one or more additional ingredients selected from bleaches, bleach activators, catalytic materials, dispersant polymers, silver-care, anti-tarnish and/or anti-corrosion agents, alkalinity sources, processing aids, dye transfer inhibiting agents, brighteners, structure elasticizing agents, fabric softeners, anti-abrasion agents, and other fabric care agents. The cleaning adjuncts particularly useful for household cleaning compositions and the levels of use have been described in, e.g., U.S. Pat. Nos. 5,576,282, 6,306,812 and 6,326,348. A list of suitable laundry or other household cleaning adjuncts is described in, e.g., International Patent Application Publication WO 99/05245.

Personal care, pet care, or cosmetic compositions (e.g., shampoos, facial cleansers, hand sanitizers, blushes, bronzers, and the like) can comprise one or more additional ingredients selected from conditioning agents (e.g., vitamins, silicone, silicone emulsion stabilizing components), cationic cellulose, or polymers (e.g., guar polymers), anti-dandruff agents, antibacterial agents, gel-forming agents, suspending agents, viscosity modifiers, dyes, non-volatile solvents or diluents (water soluble or insoluble), foam boosters, pediculicides, pH adjusting agents, perfumes, preservatives, chelators, proteins, skin active agents, sunscreens, UV absorbers, minerals, herbal/fruit/food extracts, sphingolipid derivatives, and clay.

The disclosure also provides a fuel additive comprising a fatty amide produced by any of the recombinant microorganisms and methods described herein. In certain embodiments, the fuel additive is selected from an engine performance additive, detergent, dispersant, anti-wear agent, viscosity index modifier, friction modifier, antioxidant, rust inhibitor, antifoaming agent, seal fix, lubricity additive, pour point depressant, cloud point reducer, smoke suppressant, drag reducing additive, metal deactivator, biocide and demulsifier. Fuel additives are described in more detail in U.S. Patent Application Publication 2010/0257777, which is incorporated by reference herein.

In certain embodiments, the fuel additive comprising a fatty amide produced by any of the recombinant microorganisms and methods is blended into a package comprising the fatty amide and one or more base oils used as a solvent for the fatty amide. Depending on grade and/or type, the base oil may provide a varying degree of performance benefit to an additive package, including, for example, extreme temperature benefits, anti-oxidative benefits, or a suitable pour point.

The disclosure also provides a pharmaceutical composition comprising a fatty amide produced by any of the recombinant microorganisms and methods described herein and a pharmaceutically acceptable carrier. The pharmaceutical composition can contain additional components, such as, for example, diluents, adjuvants, excipients, preservatives, pH adjusting agents, and the like, as well as additional therapeutic agents, such as, for example, therapeutic agents useful in the treatment of a particular indication (e.g., pain or inflammation).

The pharmaceutical composition can be a solid (e.g., tablet, capsule, sublingual tablet, powder, sachet) composition. The pharmaceutical composition also can be a liquid (e.g., aqueous liquid, gel, lotion, cream) composition. The pharmaceutical composition can be formulated for administration by any suitable route, such as, for example, an administration route selected from the group consisting of oral, topical, intravenous, intramuscular, intraperitoneal, intrathecal, epidural, percutaneous, subcutaneous, transmucosal, and intranasal routes.

The disclosure also provides a method of preventing or treating a disease or condition in a subject in need thereof comprising administering to the subject an effective amount of a fatty amide produced by any of the recombinant microorganisms and methods described herein, thereby preventing or treating the disease or condition in the subject.

By "effective amount" or "therapeutically effective amount," it is meant an amount that relieves (to some extent, as judged by a skilled medical practitioner) one or more symptoms of the disease or condition in a human or animal subject. Additionally, by "effective amount" or "therapeutically effective amount," it is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered. The precise amount of the composition required to be therapeutically effective will depend upon numerous factors, e.g., such as the specific activity of the active substance, the delivery device employed, physical characteristics of the substance, purpose for the administration, in addition to many patient specific considerations. The determination of amount of a composition that must be administered to be an effective amount or a therapeutically effective amount is routine in the art and within the skill of an ordinarily skilled clinician.

In some embodiments, an effective amount may be 1 ng or more, e.g., 10 ng or more, 100 ng or more, 1 μg or more, 10 μg or more, 100 μg or more, 1 mg or more, 10 mg or more, 50 mg or more, or 100 mg or more of a fatty amide of the disclosure per dosage unit. Alternatively, or in addition, an effective amount may be 5 g or less, 1 g or less, 500 mg or less, 250 mg or less, 100 mg or less, 75 mg or less, 25 mg or less, 10 mg or less, or 1 mg or less of a fatty amide of the disclosure per dosage unit. Thus, the fatty amide can be present in a dosage unit in an amount bounded by any two of the above endpoints. For example, the fatty amide can be present in a dosage unit in an amount of 100 ng-10 mg, 50 mg-250 mg, 1 μg-1 mg, or 100 mg-500 mg. A dosage unit comprising an effective amount of a fatty amide of the disclosure may be administered in a single daily dose, or the total daily dosage may be administered in divided doses of two, three, four times or more daily, as needed.

The disease or condition can be any disease or condition having one or more symptoms and/or physiological or biochemical parameters responsive to therapy with a fatty amide of the invention. In some embodiments, the disease is an inflammatory disease, and the fatty amide of the disclosure is administered in an amount sufficient to reduce inflammation. In certain embodiments, the inflammatory disorder is autoimmune disease, rheumatoid arthritis, multiple sclerosis, or Crohn's disease.

In certain embodiments, the condition is pain, and the fatty amide of the disclosure is administered in an amount sufficient to provide analgesia.

In other embodiments, the condition is hypertension, and the fatty amide of the disclosure is administered in an amount sufficient to cause the reduction of blood pressure.

Anandamide is an endogenous agonist of the cannabinoid (CB) 1 receptor and, to a lesser extent, the CB2 receptor and the vanilloid 1 receptor (Tan et al., supra). Administration of anandamide to human and animal subjects has been demonstrated to have myriad physiological effects, including regulating food intake and body weight, decreasing blood pressure, decreasing heart rate, protecting against myocardial reperfusion injury, reducing acute pain elicited by chemical, mechanical, or thermal stimuli, reducing chronic pain of neuropathic or inflammatory origin, reducing inflammation, providing neuroprotection in acute neuronal injury (e.g., traumatic brain injury, stroke, and epilepsy) and in chronic neurodegenerative disorders, (e.g., multiple sclerosis, Parkinson's disease, Huntington's disease, amyotrophic lateral sclerosis, and Alzheimer's disease), promoting bronchodilation, reducing intraocular pressure (e.g., in glaucoma patients), and promoting tumor cell apoptosis (see, e.g., Pacher et al. (2006) *Pharmacol. Rev.* 58 (3):389-462).

In some embodiments, the fatty amide is anandamide produced by the recombinant microorganisms and methods described herein, and the disease or condition is one of the aforementioned diseases or conditions capable of being treated or prevented by the administration of an effective amount of anandamide.

PEA and OEA are endogenous agonists of peroxisome proliferator-activated receptor-α (PPAR-α) (Fu et al. (2003) *Nature* 425 (6953): 90-93; and Lo Verme et al., supra). Administration of PEA or OEA to human and animal subjects has been demonstrated to evoke many of the same responses elicited by anandamide, including regulating food intake and body weight, reducing pain and inflammation, providing neuroprotection, and reducing intraocular pressure (see, e.g., Fu et al., supra, Tan et al., supra, Lo Verme et al., supra, and U.S. Pat. Nos. 6,348,498 and 6,656,972).

In some embodiments, the fatty amide is PEA produced by the recombinant microorganisms and methods described herein, and the disease or condition is one of the aforementioned diseases or conditions capable of being treated or prevented by the administration of an effective amount of PEA. In other embodiments, the fatty amide is OEA produced by the recombinant microorganisms and methods described herein, and the disease or condition is one of the aforementioned diseases or conditions capable of being treated or prevented by the administration of an effective amount of OEA.

EXAMPLES

The following specific examples are intended to illustrate the disclosure and should not be construed as limiting the scope of the claims.

Example 1

This example illustrates the construction of a genetically engineered microorganism in which the expression of an acyl-CoA dehydrogenase, an outer membrane protein receptor, a pyruvate formate lyase, a lactate dehydrogenase, and a transcriptional repressor were attenuated.

E. coli MG1655 DV4 is a genetically engineered E. coli K strain comprising fadE (an acyl-CoA dehydrogenase), fhuA (an outer membrane protein receptor), pflB (a pyruvate formate lyase), and ldhA (a lactate dehydrogenase) gene deletions (see U.S. Patent Application Publications 2011/0072714 and 2011/0162259, which are incorporated by reference herein). The fabR gene of E. coli MG1655 (GenBank Accession No. AAC76945), which encodes a transcriptional repressor was deleted from E. coli MG1655 DV4 using the Lambda Red System according to Datsenko et al. (2000) *Proc. Natl. Acad. Sci. USA* 97:6640-6645, with the following modifications described herein.

The two primers used to create the deletion strain were:

```
fabR_del_F:
                                             (SEQ ID NO: 4)
5'-ATGTTTTATTGCGTTACCGTTCATTCACAATACTGGAGCAATCCAGT ATGATTCCGGGGATCCGTCGACC-3';
and fabR_del_R:
                                             (SEQ ID NO: 5)
5'-CGTACCTCTATCTTGATTTGCTTGTTTCATTACTCGTCCTTCACATT

TCCTGTAGGCTGGAGCTGCTTCG-3'.
```

The fabR_del_F and fabR_del_R primers were used to amplify the kanamycin resistance (Km$^R$) cassette from plasmid pKD13 by PCR, as described by Datsenko et al., supra. The resulting PCR product was then used to transform electro-competent E. coli MG1655 DV4 cells containing plasmid pKD46, which cells were previously induced with arabinose for 3-4 hours, as described by Datsenko et al., supra. Following a 3 hour outgrowth in SOC medium at 37° C., the cells were plated on Luria agar plates containing 50 µg/mL of kanamycin. Colonies that were resistant to kanamycin were identified and isolated after an overnight incubation at 37° C. Disruption of the fabR gene was confirmed using primers flanking the E. coli fabR gene.

Confirmation of the deletion of fabR was performed using the following primers:

```
fabR_3:
                                             (SEQ ID NO: 6)
5'-GCGACGCGCGCACCTTGCTTAACCAGGCCC-3'
```

```
fabR_4:
                                             (SEQ ID NO: 7)
5'-CGCATCTTCGCGCCAATCCAGAACACC-3'.
```

After the deletions were confirmed, a single colony was used to remove the Km$^R$ marker in accordance with the method described by Datsenko et al., supra. The resulting MG1655 E. coli strain having fadE, fhuA, pflB, IdhA, and fabR gene deletions was named E. coli MG1655 ΔfadE_ΔfhuA_ΔpflB_ΔldhA_ΔfabR or E. coli MG1655 DG5.

This example shows the construction of E. coli MG1655 DG5, which is a genetically engineered microorganism in which the expression of an acyl-CoA dehydrogenase, an outer membrane protein receptor, a pyruvate formate lyase, a lactate dehydrogenase, and a transcriptional repressor were attenuated.

Example 2

This example illustrates the construction of a genetically engineered microorganism in which nucleotide sequences encoding a thioesterase ('tesA) and an acyl-CoA synthase (fadD) were integrated into the microorganism's chromosome under the control of an inducible promoter.

'tesA is a nucleotide sequence comprising a leaderless E. coli tesA gene (GenBank entry AAC73596, Accession U00096.2). 'tesA encodes an E. coli thioesterase (EC 3.1.1.5, 3.1.2.-) in which the first twenty-five amino acids were deleted and the amino acid in position 26, alanine, was replaced with methionine. That methionine then became the first amino acid of 'tesA (Cho et al. (1995) *J. Biol. Chem.* 270:4216-4219). E. coli fadD (GenBank entry AAC74875; Accession U00096.2) encodes an acyl-CoA synthase.

Construction of pACYC-Ptrc Plasmid Containing 'tesA or 'tesA-fadD

The 'tesA gene was obtained from a pETDuet-1-'tesA plasmid, which was constructed by cloning the 'tesA gene into an NdeI/AvrII digested pETDuet-1 plasmid (Novagen, Madison, Wis.) as described previously (see U.S. Patent Application Publication 2010/0242345 and International Patent Application Publication WO 2007/136762, which are incorporated in their entireties by reference herein). The fadD gene was obtained from a pHZ1.61 plasmid (SEQ ID NO: 8), which was constructed by cloning the fadD gene into a pCDFDuet-1 plasmid (Novagen, Madison, Wis.) as described previously (see also U.S. Patent Application Publication 2010/0257777, which is incorporated in its entirety by reference herein). The 'tesA and fadD genes were amplified from pETDuet-1-'tesA and pHZ1.61, respectively, using high fidelity PHUSION™ polymerase (New England Biolabs, Inc., Ipswich, Mass.) and the following primers:

```
'tesAForward-
                                             (SEQ ID NO: 9)
5'-CTCTAGAAATAATTTAACTTTAAGTAGGAGAUAGGTAC

CCATGGCGGACACGTTATTGAT-3'

'tesAReverse-
                                             (SEQ ID NO: 10)
5'-CTTCGAATTCCATTTAAATTATTTCTAGAGTCATTATGAGTC

ATGATTACTAAAGGC-3'
```

```
fadDForward-
                                      (SEQ ID NO: 11)
5'-CTCTAGAAATAATTTTAGTTAAGTATAAGAAGGAGATATACC

ATGGTGAAGAAGGTTTGGCTTAA-3' fadDReverse-
                                      (SEQ ID NO: 12)
5'-CTTCGAATTCCATTTAAATTATTTCTAGAGTTATCAGGCTTTA

TTGTCCAC-3'.
```

To construct the pACYC-'tesA plasmid, the 'tesA PCR product and a pACYC-Ptrc vector (SEQ ID NO: 13) were digested with NcoI and EcoRI. Following overnight ligation with T4 DNA ligase (New England Biolabs, Ipswich, Mass.), the DNA product was transformed into TOP10® ONE SHOT® cells (Invitrogen, Carlsbad, Calif.). The insertion of 'tesA into the pACYC-Ptrc vector was confirmed by restriction digestion. A SwaI restriction site and overlapping fragments for IN-FUSION™ cloning (Clontech, Mountain View, Calif.) also were created at the 3'-end of the 'tesA insert.

To construct the pACYC-Ptrc-'tesA-fadD plasmid, the pACYC-Ptrc-'tesA plasmid was subjected to an overnight restriction digestion by SwaI. The fadD PCR product amplified from pHZ1.61 was cloned downstream from the 'tesA gene using the IN-FUSION™ PCR Cloning System (Clontech, Mountain View, Calif.). The insertion of fadD was verified with restriction digestion. The insertion of fadD destroys the SwaI site following the 'tesA gene, but recreates a new SwaI site at the 3'-end of fadD.

Construction of Tn7tes and Tn7tesfad Plasmids

The pACYC-Ptrc-'tesA and pACYC-Ptrc-'tesA-fadD plasmids were used as templates to generate Ptrc-'tesA and Ptrc-'tesA-fadD cassettes, respectively. The following primers were used to obtain the cassettes:

```
IFF:
                                      (SEQ ID NO: 14)
5'-GGGTCAATAGCGGCCGCCAATTCGCGCGCGAAGGCG-3'

IFR:
                                      (SEQ ID NO: 15)
5'-TGGCGCGCCTCCTAGGGCATTACGCTGACTTGACGGG-3'.
```

Plasmid pGRG25 (GenBank Accession No. DQ460223) was purified and subjected to restriction digestions by NotI and AvrII (New England Biolabs, Inc., Ipswich, Mass.). The Ptrc-'tesA cassette was cloned into the NotI and AvrII restriction sites of pGRG25 using the IN-FUSION™ PCR cloning system (Clontech, Mountain View, Calif.), creating the Tn7tes plasmid (SEQ ID NO: 16), wherein the lacI$_q$ and Ptrc-'tesA genes are flanked by the left and right Tn7 ends. The Ptrc-'tesA-fadD cassette was cloned into the NotI and AvrII restriction sites of pGRG25 similarly, thereby creating the Tn7tesfad plasmid (SEQ ID NO: 17), wherein the lacI$_q$ and Ptrc-'tesA-fadD genes are flanked by the left and right Tn7 ends.

Generation of E. coli MG1655 DG5 Tn7-'tesA and E. coli MG1655 DG5 Tn7-'tesA-fadD The plasmids Tn7tes and Tn7tesfad were each electroporated separately into strain E. coli MG1655 DG5 (described in Example 1) using a protocol described by McKenzie et al., BMC Microbiology, 6:39 (2006). After electroporation, ampicillin-resistant cells were selected by growth in an LB medium containing 0.1% glucose and 100 µg/mL carbenicilin at 32° C. overnight, followed by selection for cells comprising the Tn7-transposition fractions by growth on LB plates containing 0.1% arabinose overnight at 32° C. Single colonies were streaked onto LB medium plates with or without ampicillin and grown overnight at 42° C. to cure of Tn7tes or Tn7tesfad plasmids. Thus, the lacI$_q$ and Ptrc-'tesA or lacI$_q$ and Ptrc-'tesA-fadD genes were integrated into the attTn7 site on the E. coli MG1655 chromosome located between the pstS and glmS genes. Integration of these genes was confirmed by PCR and sequencing using the following primers:

```
attTn7.A:
                                      (SEQ ID NO: 18)
5'-GATGCTGGTGGCGAAGCTGT-3' attTn7.C:
                                      (SEQ ID NO: 19)
5'-GTTGCGACGGTGGTACGCATAAC-3'.
```

The resulting strains were given the names E. coli MG1655 DG5 Tn7-'tesA and E. coli MG1655 DG5 Tn7-'tesA-fadD, accordingly.

The results of this example illustrate the generation of genetically engineered microorganisms in which nucleotide sequences encoding a thioesterase (i.e., E. coli MG1655 DG5 Tn7-'tesA) or a thioesterase and an acyl-CoA synthase (i.e., E. coli MG1655 DG5 Tn7-'tesA-fadD) were integrated into the host cell's chromosome under the control of an inducible promoter.

Example 3

This example illustrates a method of producing N-palmitoylethanolamide by expressing a gene encoding a palmitoylputrescine synthase in a genetically engineered microorganism.

A gene encoding a bacterial palmitoylputrescine synthase (PPS), identified as GenBank Accession No. AY632377 (Brady, S. F., et al. (2004) J. Nat. Prod., 67:1283-1286) (SEQ ID NO: 2), was synthesized by DNA2.0 (Menlo Park, Calif.). The DNA2.0 plasmid, termed pJ201:30127, was designed to contain an NcoI site flanking the start codon and a PmeI site flanking the stop codon. The PPS encoding gene in pJ201:30127 was not codon optimized. The PPS encoding gene was subcloned into the expression vector OP80, which has been described previously (see U.S. Patent Application Publication No. 2010/0154293, which is incorporated in its entirety by reference herein). The OP80 vector is based upon pCL1920, which is a low copy plasmid that expresses operably linked genes under the control of the IPTG-inducible trc promoter. To construct the OP80 vector expressing the PPS gene, plasmids OP80 and pJ201:30127 were purified and subjected to restriction digestions with NcoI/PmeI (New England Biolabs, Inc., Ipswich, Mass.). The PPS encoding gene was ligated with T4 DNA ligase into the NcoI/PmeI digested OP80 plasmid. The ligation reaction was transformed into TOP10® E. coli cells, and the cells were plated onto LB agar containing spectinomycin. Ten colonies were selected and tested for the PPS encoding insert by culturing the colonies, isolating plasmid DNA, and digesting the plasmid DNA with NcoI/PmeI. One colony was positive for plasmid containing the PPS encoding insert by restriction digestion. The plasmid was confirmed to contain the PPS encoding gene by sequence analysis, and was termed "OP80-PPS." The OP80-PPS plasmid was then transformed into E. coli MG1655 strains DG5 (described in Example 1), DG5 Tn7-'tesA (described in Example 2), and DG5 Tn7-'tesA-fadD (described in Example 2). As a control, the OP80 empty vector was transformed into *E. coli* MG1655 strains DG5, DG5 Tn7-'tesA, and DG5 Tn7-'tesA-fadD. All six strains were cultured in LB broth with no additional glucose. When each culture reached an $OD_{600}$ of 1.2, IPTG was added to a final concentration of 1 mM, along with ethanolamine (0.1% (v/v)). After 24 hrs, the cultures were harvested and extracted with ethyl acetate (2 volumes of culture to 1 volume of ethyl acetate), and the organic fraction was collected and utilized for analysis of fatty species by GC-MS.

All samples were analyzed by GC-MS (Agilent 6850 GC with 5975B VL MSD) equipped with a 30 m×0.25 mm 0.25 μm film Agilent HP-5-MS column for separation, with the mass detectors electron ionization (EI) in full scan mode (50-500 m/z). One μL of the ethyl acetate extraction was injected on the Agilent splitless inlet set at 300° C. The column was temperature programmed as follows: 100° C. for 5 min, increase to 320° C. at 20° C./min, and hold at 320° C. for 5 min. The carrier gas helium was set at a flow rate of 1.2 mL/min. A representative chromatogram with an interpretation of the mass spectra of *E. coli* MG1655 strain DG5 transformed with OP80-PPS is shown in FIG. 1. A peak having a retention time of 13.1 min was identified in the GC-MS traces of all *E. coli* MG1655 strains DG5, DG5 Tn7-'tesA, and DG5 Tn7-'tesA-fadD transformed with OP80-PPS. This peak was identified as N-palmitoylethanolamide. The peak identified as N-palmitoylethanolamide was not present in any of the control strains transformed with empty vector.

Figure 2E:
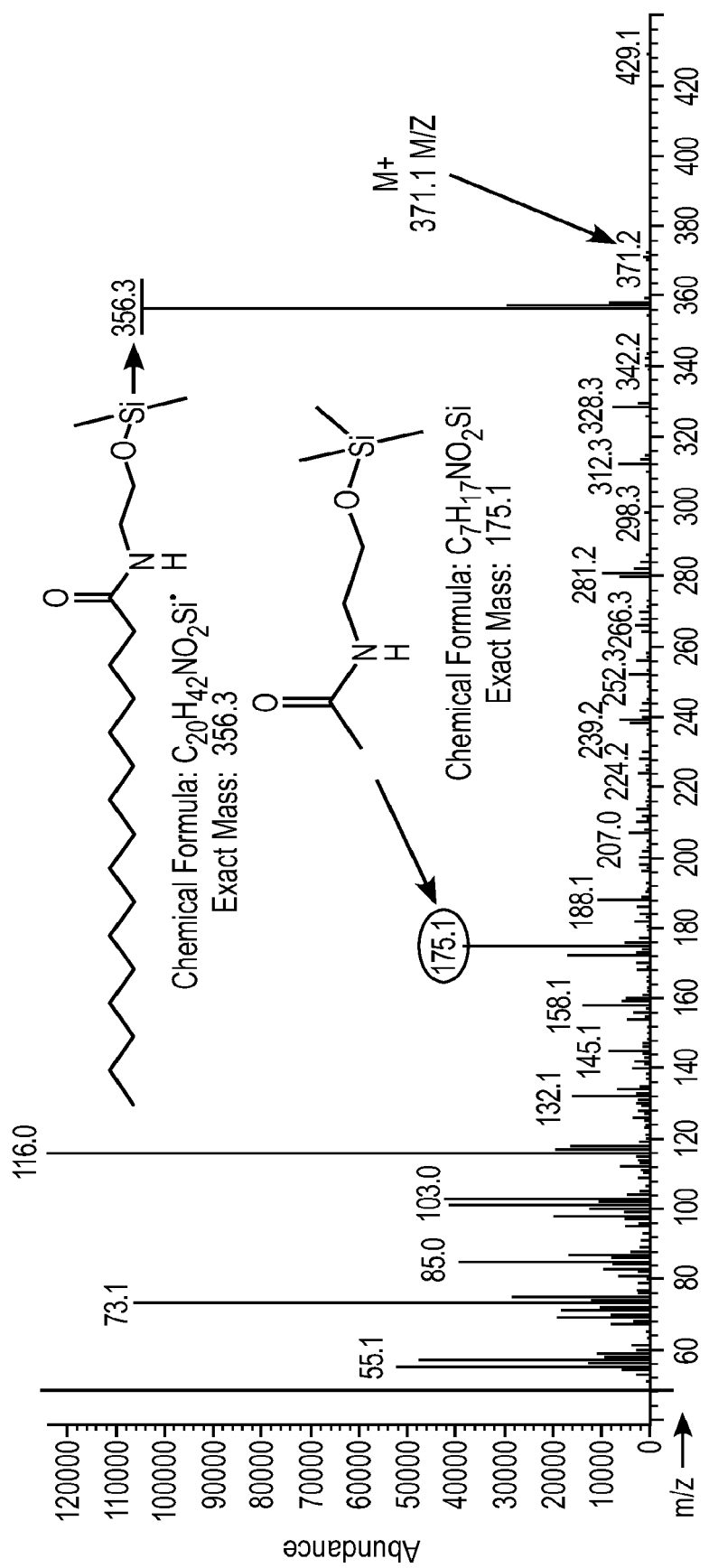
FIGS. 2A-2D are GC-MS chromatograms of the N-palmitoylethanolamide product following derivatization with N,O-bis(trimethylsilyl)-trifluoroacetamide (BSTFA).

It was estimated that approximately 200 mg/L of N-palmitoylethanolamide was produced in *E. coli* MG1655 strain DG5 transformed with OP80-PPS. *E. coli* MG1655 strain DG5 is engineered to produce fatty acyl-ACP, whereas DG5 Tn7-'tesA is engineered to produce free fatty acid and DG5 Tn7-'tesA-fadD is engineered to produce fatty acyl-CoA. Since these results demonstrated that all three strains produced N-palmitoylethanolamide, the production of N-palmitoylethanolamide in the parental DG5 strain suggests that the PPS enzyme encoded by gene AY632377 uses C16:0 acyl-ACP as a substrate in the presence of the primary ethanolamine. The N-palmitoylethanolamide identified in FIG. 1 was further characterized by derivatization with N,O-bis(trimethylsilyl)-trifluoroacetamide (BSTFA), in which the hydroxyl group was trimethylsilyl-protected. As shown in FIG. 2A, a peak in the GC-MS trace having a retention time of 13.3 min was identified as the trimethylsilyl (TMS)-protected product.

The results of this example illustrate a method of producing N-palmitoylethanolamide by expressing a PPS enzyme encoded by gene AY632377 in a bacterial strain that was engineered to produce fatty acyl-ACP. In addition, these results suggest that a single enzyme (i.e., PPS) can perform a secondary amidation directly from acyl-ACP and a primary amine head group in vivo.

Example 4

This example shows a method of producing N-palmitoylethanolamide by expressing a gene encoding a palmitoyl-putrescine synthase in a genetically engineered microorganism.

The OP80 empty vector or OP80-PPS plasmid was transformed into *E. coli* MG1655 strains DG5, DG5 Tn7-'tesA, and DG5 Tn7-'tesA-fadD, as described in Example 3. Each of the six strains was cultured overnight in LB broth with no additional glucose. Then, each of the overnight cultures was inoculated in nutrient rich media containing glucose. More specifically, 1 mL of each of the overnight cultures was inoculated in triplicate into nutrient rich 2N-BT (2% glucose, nitrogen limited medium, 0.2M Bis-Tris, pH 7.0, 0.1% Triton): LB media (1:10) containing 1 mM IPTG, antibiotics, and 1% ethanolamine, and cultured in a pH-controlled incubator. After 48 hrs, the $OD_{600}$ of each culture was recorded, and the cells were harvested and extracted with ethyl acetate (2 volumes of culture to 1 volume of ethyl acetate). The organic fractions were collected and utilized for GC-MS analysis as described in Example 3. A peak having a retention time of 13.1 min was found to be most abundant in the GC-MS trace for *E. coli* MG1655 strain DG5 Tn7-'tesA-fadD transformed with OP80-PPS. The peak having a retention time of 13.1 was second most abundant in strain DG5 transformed with OP80-PPS, and third most abundant in strain DG5 Tn7-'tesA transformed with OP80-PPS. The 13.1 min peak was identified as N-palmitoylethanolamide from all strains. The peak identified as N-palmitoylethanolamide was not present in any of the control DG5 strains transformed with empty vector.

As noted above, *E. coli* MG1655 strain DG5 Tn7-'tesA-fadD is engineered to produce fatty acyl-CoA. Therefore, the production of N-palmitoylethanolamide in the DG5 Tn7-'tesA-fadD strain suggests that the PPS enzyme encoded by gene AY632377 also can use fatty acyl-CoA as a substrate in the presence of ethanolamine.

The results of this example show a method of producing N-palmitoylethanolamide by expressing a PPS enzyme encoded by gene AY632377 in a bacterial strain that was engineered to produce fatty acyl-CoA. In addition, these results suggest that a single enzyme (i.e., PPS) can perform a secondary amidation directly from a fatty thioester and a primary amine head group in vivo.

Example 5

This example shows a method of producing saturated and unsaturated fatty amides by expressing a gene encoding a PPS in a genetically engineered microorganism.

Figure 3:
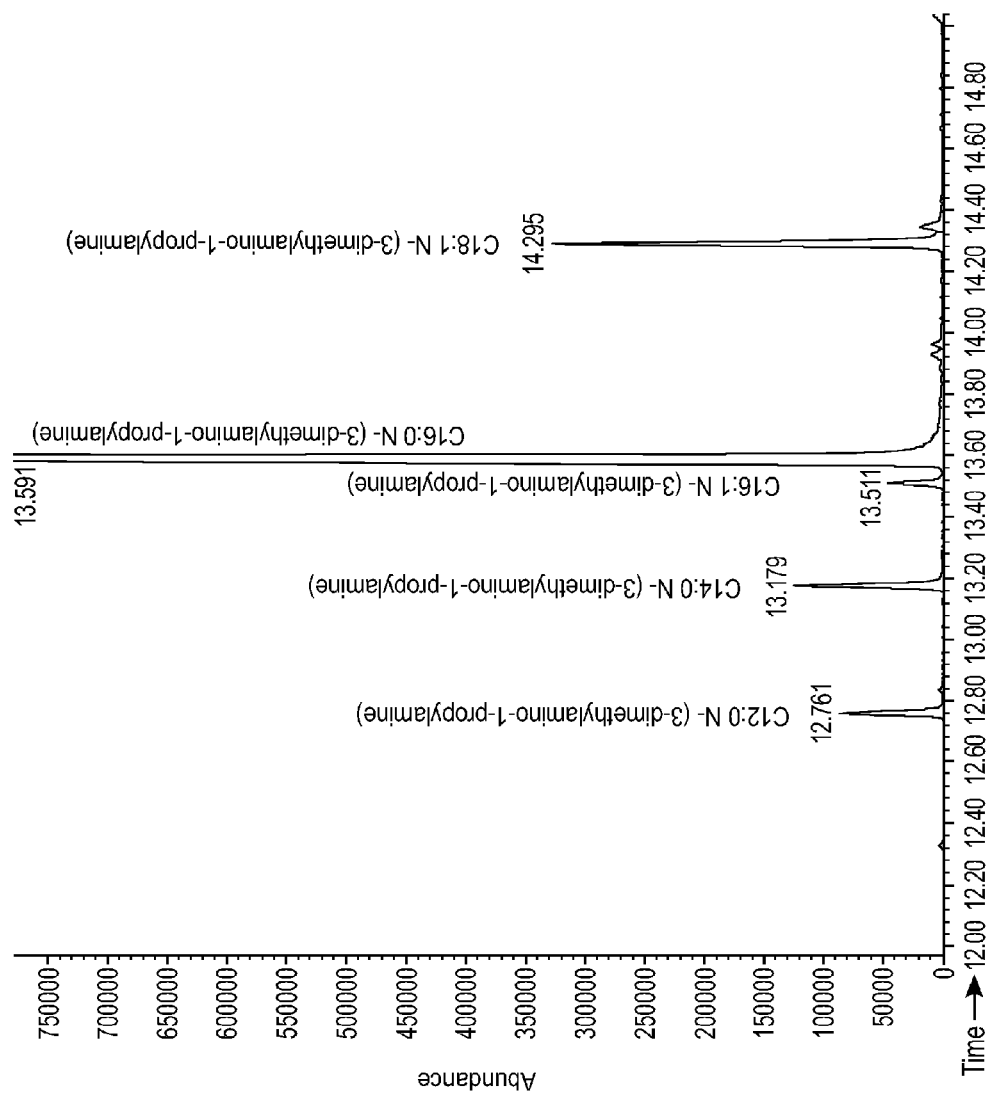
FIG. 3 is a GC-MS chromatogram of the fatty N-(3-dimethylamino-1-propylamine)amides produced by *E. coli* MG1655 strain DG5 transformed with an expression vector encoding a PPS cultured in the presence of 3-dimethylamino-1-propylamine.

Fatty 3-dimethylamino-1-propylamide is a precursor in the synthesis of the amphoteric detergent cocamidopropyl betaine (CAPB). To determine whether fatty N-(3-dimethylamino-1-propylamine)amides could be produced in a microorganism genetically engineered to express a PPS, *E. coli* MG1655 strain DG5 cells were transformed with OP80 empty vector or OP80-PPS plasmid, and cultured overnight in LB broth with no additional glucose. Then, each of the overnight cultures was inoculated in nutrient rich media containing glucose. More specifically, 1 mL of each of the overnight cultures was inoculated in triplicate into nutrient rich 2N-BT (2% glucose, nitrogen limited medium, 0.2M Bis-Tris, pH 7.0, 0.1% Triton): LB (1:10) media containing 1 mM IPTG, antibiotics, and 1% primary amine 3-dimethylamino-1-propylamine, and cultured in a pH-controlled incubator. After 60 hrs, the $OD_{600}$ of each culture was recorded, and the cells were harvested and extracted with ethyl acetate (2 volumes of culture to 1 volume of ethyl acetate). The organic fractions were collected and utilized for GC-MS analysis as described in Example 3. The chromatogram was analyzed by extraction ion chromatogram for ion 58, which is a common ion for fatty N-(3-dimethylamino-1-propylamine)amides. Fatty N-(3-dimethylamino-1-propylamine)amides containing C12:0 (12.8 min), C14:0 (13.2 min), C16:1 (13.5 min), C16:0 (13.6 min), and C18:1 (14.3 min) fatty chains were identified in the GC-MS trace (FIG. 3). Fatty amides containing a C16:0 fatty chain were identified as being the most abundant in the GC-MS trace (FIG. 3).

The results of this example show a method of producing fatty amides with various fatty chain lengths having either zero or one unsaturation by culturing an *E. coli* strain that was engineered to produce acyl-ACP and which further expressed a PPS enzyme encoded by gene AY632377 in a medium containing 3-dimethylamino-1-propylamine.

Example 6

This example illustrates a method for producing various fatty amides by feeding a variety of primary amines to a genetically engineered microorganism.

Figure 4:
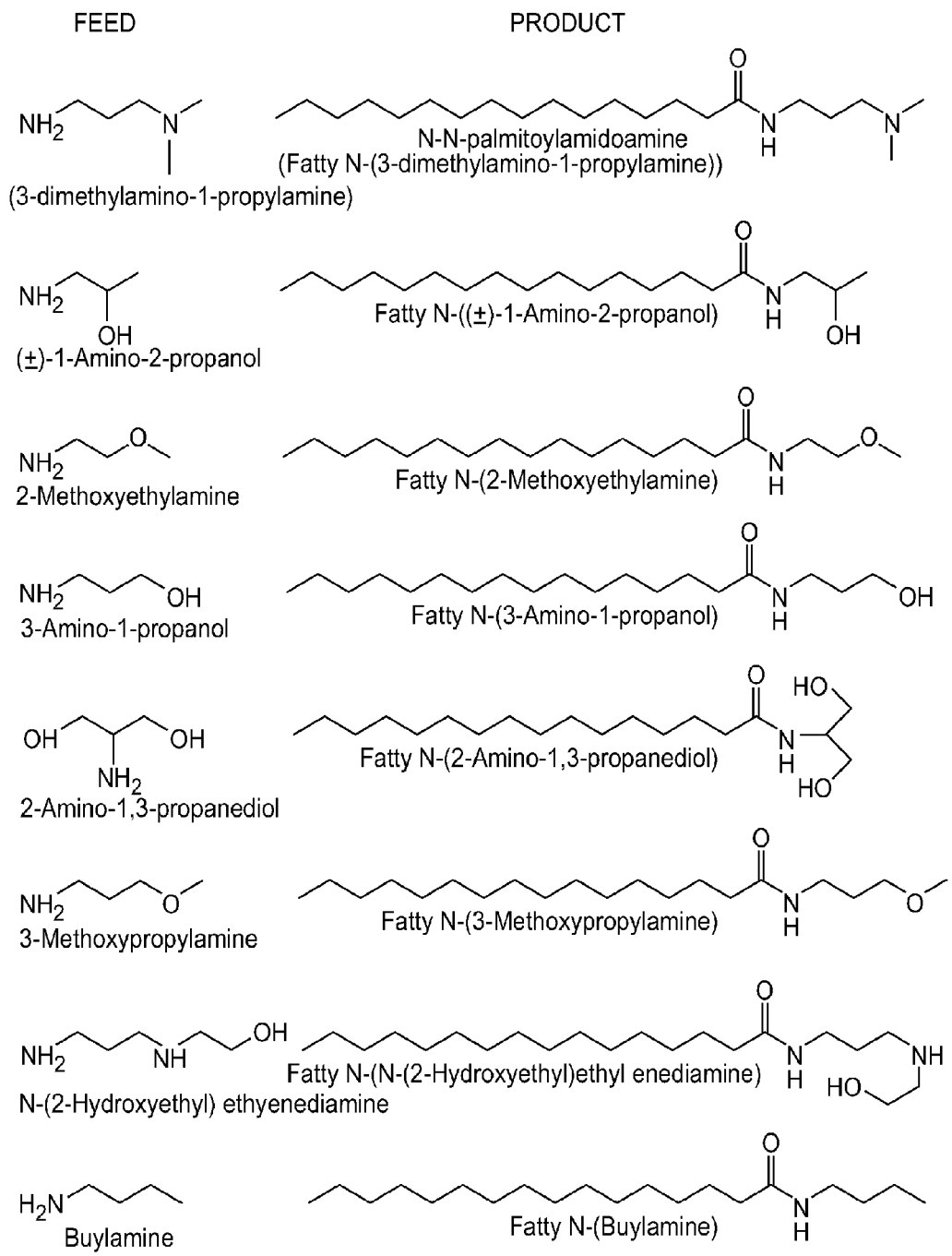
FIG. 4 depicts the fatty amide products obtained from *E. coli* MG1655 cells transformed with an expression vector encoding a PPS and cultured in the presence of the indicated primary amine feeds.

The OP80 empty vector or OP80-PPS plasmid was transformed into *E. coli* MG1655 strains DG5, DG5 Tn7-'tesA, and DG5 Tn7-'tesA-fadD, as described in Example 3. Each of the six strains was cultured overnight in LB broth with no additional glucose. Then, each of the overnight cultures was inoculated in nutrient rich media containing glucose. More specifically, 1 mL of each of the overnight cultures was inoculated into nutrient rich 2N-BT (2% glucose, nitrogen limited medium, 0.2M Bis-Tris, pH 7.0, 0.1% Triton): LB (1:10) media containing 1 mM IPTG, antibiotics, and 1% of one of the following primary amines: (±)-1-amino-2-propanol, 2-methoxyethylamine, 3-amino-1-propanol, 2-amino-1-3-propanediol, 3-methoxypropylamine, N-(2-hydroxyethyl) ethylenediamine, or butylamine. The cultures were incubated in a pH-controlled environment for 60 hrs. The $OD_{600}$ of each culture was recorded, and the cells were harvested and extracted with ethyl acetate (2 volumes of culture to 1 volume of ethyl acetate). The organic fractions were collected and utilized for GC-MS analysis as described in Example 3. Fatty amides were obtained from each of the PPS-expressing *E. coli* strains fed with a primary amine. The fatty amide product obtained from each feed substrate is depicted in FIG. 4. The fatty amide products were not detected in *E. coli* strains transformed with empty vector.

The results of this example demonstrate a method of producing distinct species of fatty amides in an *E. coli* strain that was genetically engineered to produce fatty thioesters and which further expressed a PPS enzyme encoded by gene AY632377 by varying the primary amine feed type.

Example 7

This example shows that expression of a homolog of PPS in a genetically engineered microorganism produced the same fatty amide compounds that are produced when PPS is expressed.

The PPS encoded by AY632377 (SEQ ID NO: 2) was previously determined not to have a sequence identity of greater than 20% to any other known sequence by BLAST analysis (see Brady et al. (2004) *J. Nat. Prod.,* 67: 1283-1286). The amino acid sequence of the PPS enzyme encoded by gene AY632377, i.e., GenBank Accession No. AAV33349 (SEQ ID NO: 1) was subjected to a BLAST search of the National Center for Biotechnology Information (NCBI) database. A homologue, encoding the enzyme, N-(4-amino-2-hydroxylbutyl)tetradecanamide synthase (AhtS) (GenBank Accession No. ACX33975.1) (SEQ ID NO: 3), was identified as having an amino acid sequence that is 38% identical to the amino acid sequence of PPS encoded by gene AY632377. The gene encoding AhtS was synthesized by GENEART™ (Life Technologies, Grand Island, N.Y.) and cloned into the expression vector OP80, as follows. Plasmid OP80 was purified and subjected to restriction digestions with NcoI/PmeI (New England Biolabs, Inc., Ipswich, Mass.). The AhtS gene was cloned into OP80 using the IN-FUSION™ PCR Cloning System (Clontech, Mountain View, Calif.) with the following primers:

```
3.10.10-2_InfusF:
                                      (SEQ ID NO: 20)
5'-GAGGAATAAACCATGCCCATTCTTGAAAGCGTGGG-3'
and 3.10.10-2_InfusR:
                                      (SEQ ID NO: 21)
5'-AGCTGGAGACCGTTTAAACTTATAAACCGCTGTTTGTCGCAA
CCG-3'.
```

Two colonies were positive for plasmid containing the AhtS-encoding insert by restriction digestion. The plasmid was confirmed to contain the AhtS-encoding gene by sequence analysis, and was termed "OP80-AhtS." The OP80-AhtS plasmid was transformed into *E. coli* MG1655 strains DG5, DG5 Tn7-'tesA, and DG5 Tn7-'tesA-fadD. The three strains were cultured and induced as described in Example 4, and each culture was fed either 3-dimethylamino-1-propylamine, (±)-1-amino-2-propanol, or ethanolamine to a final concentration of 1%. After 60 hrs of culture in a pH-controlled incubator, the cultures were harvested and extracted with ethyl acetate (2 volumes of culture to 1 volume of ethyl acetate). The organic fractions were collected and utilized for GC-MS analysis as described in Example 3.

Figure 5:
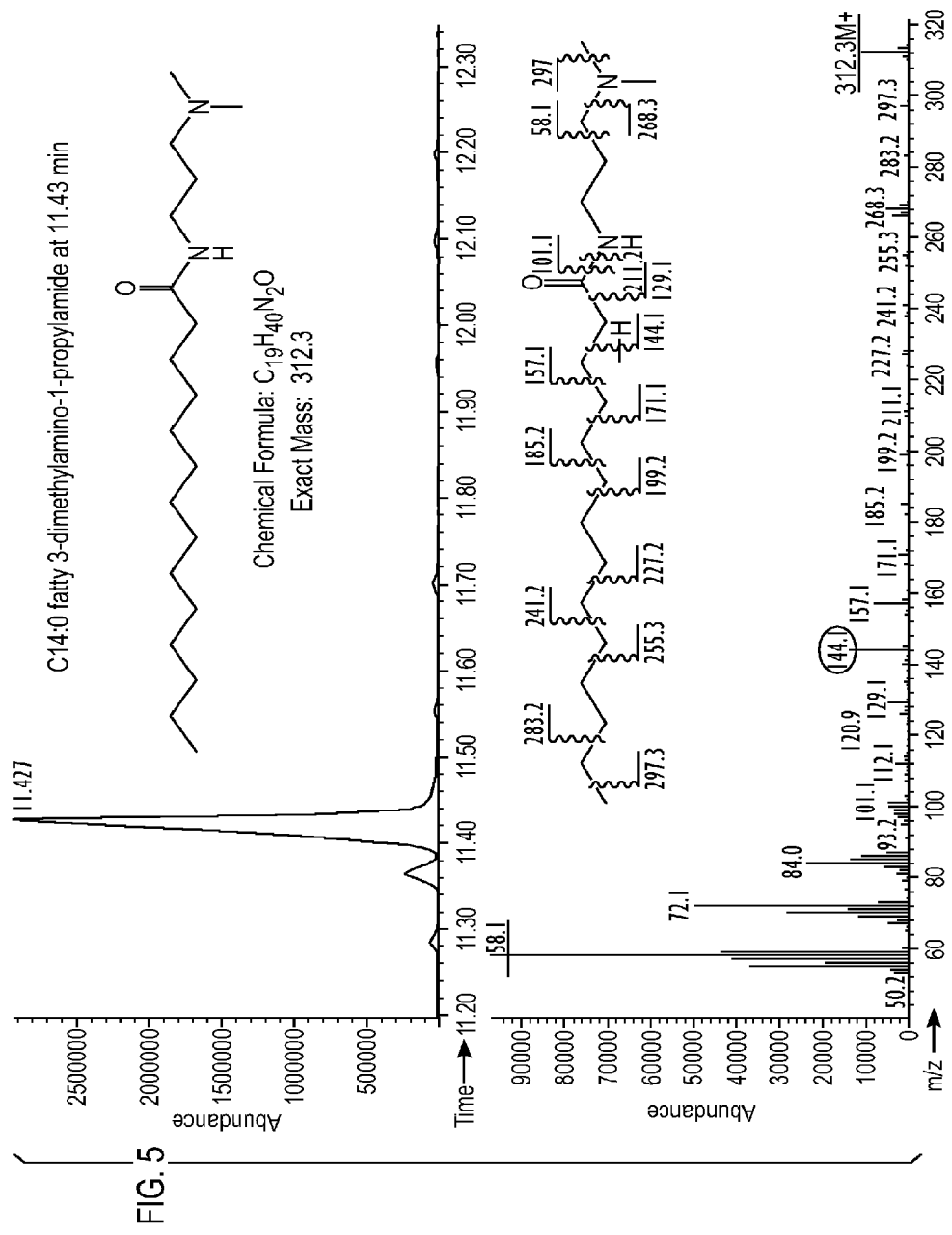
FIG. 5 is a representative GC-MS chromatogram of the fatty species produced by an *E. coli* MG1655 strain transformed with an expression vector encoding the enzyme N-(4-amino-2-hydroxylbutyl)tetradecanamide synthase (AhtS) cultured in the presence of 3-dimethylamino-1-propylamine. The upper panel depicts a peak having a GC retention time of 11.4 min which was identified as C14:0 fatty N-(3-dimethylamino-1-propylamide) by MS analysis depicted in the lower panel.

Fatty amides were obtained from each of the AhtS-expressing *E. coli* strains fed with each of the primary amines. A representative GC-MS trace of the products produced by *E. coli* MG1655 DG5 Tn7-'tesA-fadD transformed with OP80-AhtS fed with 3-dimethylamino-1-propylamine is provided as FIG. 5. The peak having a GC retention time of 11.4 min was confirmed as C14:0 fatty N-(3-dimethylamino-1-propylamide) by MS analysis (FIG. 5). Fatty amide products were not detected in *E. coli* strains transformed with empty vector. The highest amount of amides were produced in *E. coli* MG1655 strain DG5 Tn7-'tesA-fadD, whereas the lowest amount of amides were produced in *E. coli* MG1655 strain DG5 Tn7-'tesA. The increased production of amides in the DG5 Tn7-'tesA-fadD strain suggests that the AhtS enzyme has a preference for C14:0 fatty thioester substrates. These data also suggest that both AhtS and PPS can use each of the two fatty thioester substrates (i.e., fatty-ACPs and fatty-CoAs) in *E. coli* to make fatty amides.

The results of this example demonstrate that the AhtS enzyme can catalyze the same type of reaction between primary amines and fatty thioester substrates as the PPS enzyme. In addition, the data shown in this example indicated that the AhtS enzyme has a preference for C14:0 fatty thioester substrates.

Example 8

This example provides an in vivo method for generating a primary amine useful as a starting material in the generation of a fatty amide according to the present disclosure.

Figure 6:
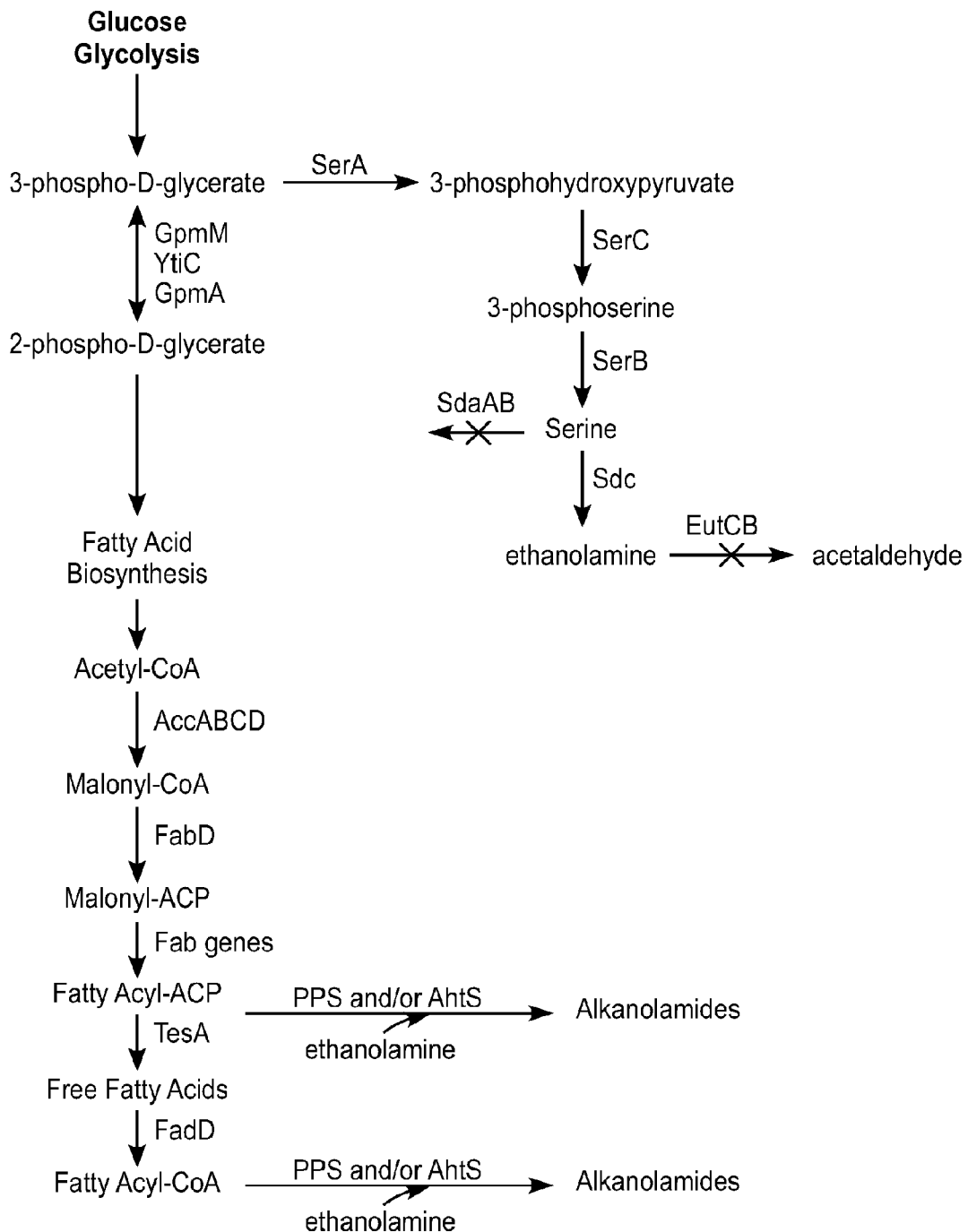
FIG. 6 is a schematic diagram of metabolic pathways which can be genetically modified according to the methods of the disclosure.

In vivo production of ethanolamine can be achieved by genetically increasing serine biosynthesis and serine decarboxylation pathways. To do so, the glycolytic intermediate 3-phosphoglycerate is increased by engineering *E. coli* strain MG1655 to overexpress phosphoglycerate mutases (gpm AB). The serine production pathway is engineered by overexpressing phosphoglycerate dehydrogenase (serA), 3-phosphoserine aminotransferase (serC), and 3-phosphoserine phosphatase (serB). A heterologous serine decarboxylase (SDC), which decarboxylates serine to ethanolamine, is expressed in the host. In order to prevent the strain from metabolizing ethanolamine and serine, the genes encoding the degradation enzymes ethanolamine ammonia-lyase (eutABC) and serine deaminases (sdaAB) are deleted (FIG. 6). Fatty amides can then be produced in the recombinant microorganism which produces ethanolamine by overexpressing a polypeptide, such as PPS or AhtS, which catalyzes the conversion of ethanolamine and an acyl thioester to a fatty amide.

Various modifications and variations of the present disclosure will be apparent to those skilled in the art without departing from the scope and spirit of the disclosure. Although the disclosure has been described in connection with specific preferred embodiments, it should be understood that the claims should not be unduly limited to such specific embodiments. Indeed, various modifications of the described modes for carrying out the disclosure, which are understood by those skilled in the art are intended to be within the scope of the claims.

We claim:

1. A recombinant microorganism comprising an exogenous nucleic acid sequence encoding a palmitoylputrescine synthase (PPS) haying at least 90% sequence identity to the amino acid sequence of SEQ. ID. NO.: 1, wherein the PPS catalyzes the conversion of a primary amine and an acyl thioester to a fatty amide, wherein the microorganism further expresses an exogenous thioesterase (EC 3.12.14 or EC 3.1.1.5) and is cultured in the presence of a carbon source.

2. The recombinant microorganism of claim 1, wherein the PPS polypeptide has an amino acid sequence comprising SEQ ID NO: 1.

3. The recombinant microorganism of claim 1, wherein the PPS polypeptide is encoded by an exogenous nucleic acid sequence comprising SEQ ID NO: 2.

4. The recombinant microorganism of claim 1, wherein the carbon source is a carbohydrate.

5. The recombinant microorganism of claim 1, wherein the primary amine is selected from the group consisting of 3-dimetylamino-1-propylamine, ±-1-amino-2-propanol, 2-methoxyethylamine, 3-amino-l-propanol, 2-amino-1,3-propanediol, 3-methoxypropylamine, N-(2-hydroxyethyl)ethylenediamine, butylamine, and 1,4-diaminobutane, or a combination thereof.

6. The recombinant microorganism of claim 5, wherein the acyl thioester is a fatty acyl-ACP or a fatty acyl-CoA.

7. The recombinant microorganism of claim 6, wherein the fatty acyl-ACP or the fatty acyl-CoA is produced by the microorganism.

8. The recombinant microorganism of claim 1, wherein the recombinant microorganism comprises exogenous nucleic acid sequences encoding one or more of a fatty acid biosynthetic polypeptide and an acyl-CoA synthase polypeptide (EC 2.3.1.86).

9. The recombinant microorganism of claim 8, wherein the microorganism comprises exogenous nucleic acid sequences encoding a thioesterase polypeptide and an acyl-CoA synthase polypeptide.

10. The recombinant microorganism of claim 8, wherein the exogenous nucleic acid sequence encoding the thioesterase polypeptide comprises a nucleic acid sequence of 'tesA.

11. The recombinant microorganism of claim 1, wherein the microorganism is a bacteria, a cyanobacteria, an algae, or a fungi.

12. The recombinant microorganism of claim 11, wherein the microorganism is a fungi.

13. The microorganism of claim 12, wherein the fungi is a yeast or a filamentous fungi.

14. The recombinant microorganism of claim 1, wherein the microorganism is a *Saccharomyces cerevisiae, Candida lipolytica, Escherichia coli, Arthrobacter, Rhodotorula glutinins, Acinetobacter, Candida lipolytica, Botryococcus braunii, Vibrio furnissii, Micrococcus leuteus, Stenotrophomonas maltophilia, Bacillus subtilis, Bacillus lichenoformis, Psuedomonus putida, Psuedomonas florescens, Streptomyces coelicolor, Synechococcus sp. PCC7002, Thermosynechococcus elongates*BP-1, *Prototheca moriformis, Prototheca krugani, Prototheca stagnora, Prototheca zopfii*, or *Chorella protothecoide* cell.

15. The recombinant microorganism of claim 14, wherein the microorganism is an *Arthrobacter AK* 19, *Acinetobacter* sp. strain M-1, *E. coli* B, *E. coli* C, *E. coli* K, or *E. coli* W cell.

16. The recombinant microorganism claim 5, wherein the fatty amide is a fatty alkanolamide or a fatty amidoamine.

17. The recombinant microorganism of claim 1, wherein the microorganism expresses a serine decarboxylase polypeptide.

18. A method of producing a fatty amide comprising:
   (a) providing a recombinant microorganism according to claim 1; and
   (b) culturing the recombinant microorganism in a culture medium under conditions suitable for expression of the nucleic acid sequence encoding the polypeptide that catalyzes the conversion of the primary amine and the acyl thioester to the fatty amide in the presence of at least one substrate for the polypeptide.

19. The method of claim 18, further comprising isolating the fatty amide from the culture medium.

20. The method of claim 18, wherein the fatty amide is a C8, C9, C10, C11, C12, C13, C14, C15, C16, C17, C18, C19, or C20 fatty alkanolamide.

21. The method of claim 18, wherein the fatty amide is a C8, C9, C10, C11, C12, C13, C14, C15, C16, C17, C18, C19, or C20 fatty amidoamine.

* * * * *

SEQUENCE LISTING

```
<160> NUMBER OF SEQ ID NOS: 22

<210> SEQ ID NO 1
<211> LENGTH: 207
<212> TYPE: PRT
<213> ORGANISM: Unknown
<220> FEATURE:
<221> NAME/KEY: source
<223> OTHER INFORMATION: /note="Description of Unknown: Uncultured
      bacterium"

<400> SEQUENCE: 1

Met Glu Ser Leu Tyr Asn Gly Asp Gly Phe Val Ile Ala Arg Ala Thr
1               5                   10                  15

Ala Leu Glu Glu Ile Glu Glu Ser Val Thr Leu Phe Glu Ala Val Ser
            20                  25                  30

Ala Glu Met Gly Trp Ser Pro Gly Asp Arg Leu Arg Ala Tyr Ala Ala
        35                  40                  45

Asn Ala Glu Tyr Leu Met Ala Leu Val Gly Gly Ala Leu Ala Gly Ala
    50                  55                  60

Val Gln Ile Val Leu Ser Asn Gly His Asp Pro Met Pro Ser Asp His
65                  70                  75                  80

Val Trp Pro Glu Leu Ala Ala Gly Arg Arg Tyr Asp Leu Ala His Ala
                85                  90                  95

Ser Val Met Ala Leu Ala Pro Arg Phe Arg Gly Ala Ala Gly Leu Phe
            100                 105                 110

Gly Pro Leu Gly Val Glu Met Trp Arg Leu Cys Arg Asp Ala Gly Lys
        115                 120                 125

Ser Glu Ile Trp Ile Glu Cys Val Pro Arg Asn Leu Ala Val Tyr Arg
    130                 135                 140

Arg Cys Gly Trp Pro Leu Glu Val Ala Gly Glu Leu Arg Thr His Phe
145                 150                 155                 160

Gly Glu Pro Cys Tyr Leu Ala Arg Met Gly Val Glu Ala Val Ala Glu
                165                 170                 175

Ser Leu Arg Ala Arg Ala Gly Arg Cys Asp Gly Phe Ala Arg Leu Val
            180                 185                 190

Ala Gln Ala Tyr Arg Asp Thr Gly Trp Arg Ser Met Gly Leu Ala
        195                 200                 205

<210> SEQ ID NO 2
<211> LENGTH: 624
<212> TYPE: DNA
<213> ORGANISM: Unknown
<220> FEATURE:
<221> NAME/KEY: source
<223> OTHER INFORMATION: /note="Description of Unknown: Uncultured
      bacterium"
```

-continued

<400> SEQUENCE: 2

```
atggaaagtt tgtacaatgg cgacggattc gtcatcgcaa gggcgacggc cctggaagag    60
atcgaggagt cggtcacact cttcgaggcg gtctccgccg aaatgggatg gagccctggg   120
gatcggcttc gggcatacgc agcgaacgcg gagtacctga tggcgctagt cggcggagcg   180
ctggctgggg cggtgcagat cgtgctctcc aacggtcacg atcctatgcc ttcggaccac   240
gtctggccgg aacttgcggc gggtcgacga tatgaccttg cgcacgcgtc agtgatggcg   300
cttgccccgc gcttccgggg agcggcagga ctattcgggc gcttggcgt cgagatgtgg    360
aggctttgcc gggacgccgg gaaatccgag atatggatcg agtgcgtgcc gaggaacctt   420
gcggtgtacc gaagatgtgg ttggccgctg gaggtggcgg gcgagttgcg gacccatttc   480
ggcgagcctt gctacctggc gcgaatgggc gtggaggcgg tggcggaatc tctgagggcc   540
agagccggcc gctgcgatgg gttcgccaga ctggtcgcgc aggcttaccg agacaccgga   600
tggcggtcaa tggggcttgc gtaa                                          624
```

<210> SEQ ID NO 3
<211> LENGTH: 220
<212> TYPE: PRT
<213> ORGANISM: Unknown
<220> FEATURE:
<221> NAME/KEY: source
<223> OTHER INFORMATION: /note="Description of Unknown: Uncultured bacterium RM44"

<400> SEQUENCE: 3

```
Met Pro Ile Leu Glu Ser Val Gly Phe Met Lys Thr Leu Trp Glu Ser
1               5                   10                  15
Gly Gly Ala Gln Val Ala Leu Met Glu Ser Arg Glu Glu Thr Ser His
            20                  25                  30
Met Val Gly Ile Leu Glu Gly Ile Ala Ala Glu Leu Ser Trp Arg Pro
        35                  40                  45
Gly Thr Gln Leu Arg Asp Tyr Gln Asp Arg Ala Ala His Leu Ala Val
    50                  55                  60
Leu Val Gly Ser Glu Ile Val Gly Gly Leu Gln Ile Val Thr Ser Pro
65                  70                  75                  80
Ser Ala Asp Cys Leu Pro Tyr Arg Leu Val Trp Pro Glu Val Cys Val
                85                  90                  95
Pro Asp Gly Ala Ala Ile Ala Asp Ile Thr Ile Leu Ala Leu Arg Lys
            100                 105                 110
Glu Tyr Arg Ala Arg Phe Asn Leu Phe Trp Pro Leu Cys Val Glu Leu
        115                 120                 125
Trp Arg His Cys Val Ala Glu Gly Ala Thr Glu Met Arg Leu Glu Ala
    130                 135                 140
Thr Pro Asp Thr Leu Arg Leu Tyr Arg Arg Ile Gly Trp Pro Leu Glu
145                 150                 155                 160
Val Ile Gly Asp Leu Arg Leu His Trp Asn Glu Pro Cys Phe Leu Cys
                165                 170                 175
Arg Met Gly Ile Val Asp Val Ala Gly Ala Met Val Val Arg Ala Leu
            180                 185                 190
Gln Ser Ala Thr Tyr Gln Ala Val Leu Ala Gly Met Ser Arg Pro Val
        195                 200                 205
Ala Ser Ala Ser Pro Val Ala Thr Asn Ser Gly Leu
    210                 215                 220
```

<210> SEQ ID NO 4
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 4

```
atgttttatt gcgttaccgt tcattcacaa tactggagca atccagtatg attccgggga    60
tccgtcgacc                                                           70
```

<210> SEQ ID NO 5
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 5

```
cgtacctcta tcttgatttg cttgtttcat tactcgtcct tcacatttcc tgtaggctgg    60
agctgcttcg                                                           70
```

<210> SEQ ID NO 6
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 6

```
gcgacgcgcg caccttgctt aaccaggccc                                     30
```

<210> SEQ ID NO 7
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 7

```
cgcatcttcg cgccaatcca gaacacc                                        27
```

<210> SEQ ID NO 8
<211> LENGTH: 6700
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
ggggaattgt gagcggataa caattcccct gtagaaataa ttttgtttaa ctttaataag    60
gagatatacc atggtgaaga aggtttggct taaccgttat cccgcggacg ttccgacgga   120
gatcaaccct gaccgttatc aatctctggt agatatgttt gagcagtcgg tcgcgcgcta   180
cgccgatcaa cctgcgtttg tgaatatggg ggaggtaatg accttccgca agctggaaga   240
```

```
acgcagtcgc gcgtttgccg cttatttgca acaagggttg gggctgaaga aaggcgatcg    300
cgttgcgttg atgatgccta atttattgca atatccggtg gcgctgtttg gcattttgcg    360
tgccgggatg atcgtcgtaa acgttaaccc gttgtatacc ccgcgtgagc ttgagcatca    420
gcttaacgat agcggcgcat cggcgattgt tatcgtgtct aactttgctc acacactgga    480
aaaagtggtt gataaaaccg ccgttcagca cgtaattctg acccgtatgg gcgatcagct    540
atctacggca aaaggcacgg tagtcaattt cgttgttaaa tacatcaagc gtttggtgcc    600
gaaataccat ctgccagatg ccatttcatt tcgtagcgca ctgcataacg gctaccggat    660
gcagtacgtc aaacccgaac tggtgccgga agatttagct tttctgcaat acaccggcgg    720
caccactggt gtggcgaaag gcgcgatgct gactcaccgc aatatgctgg cgaacctgga    780
acaggttaac gcgacctatg gtccgctgtt gcatccgggc aaagagctgg tggtgacggc    840
gctgccgctg tatcacattt ttgccctgac cattaactgc ctgctgttta tcgaactggg    900
tgggcagaac ctgcttatca ctaacccgcg cgatattcca gggttggtaa agagttagc     960 gaaatatccg tttaccgcta tcacgggcgt taacaccttg ttcaatgcgt tgctgaacaa    1020
taaagagttc cagcagctgg atttctccag tctgcatctt tccgcaggcg gagggatgcc    1080
agtgcagcaa gtggtggcag agcgttgggt gaaactgaca ggacagtatc tgctggaagg    1140
ctatggcctt accgagtgtg cgccgctggt cagcgttaac ccatatgata ttgattatca    1200
tagtggtagc atcggtttgc cggtgccgtc gacggaagcc aaactggtgg atgatgatga    1260
taatgaagta ccaccgggtc aaccgggtga gctttgtgtc aaaggaccgc aggtgatgct    1320
gggttactgg cagcgtccgg atgctacaga tgagatcatc aaaaatggct ggttacacac    1380
cggcgacatc gcggtgatgg atgaagaagg gttcctgcgc attgtcgatc gtaaaaaaga    1440
catgattctg gtttccggtt ttaacgtcta tcccaacgag attgaagatg tcgtcatgca    1500
gcatcctggc gtacaggaag tcgcggctgt tggcgtacct tccggctcca gtggtgaagc    1560
ggtgaaaatc ttcgtagtga aaaagatcc atcgcttacc gaagagtcac tggtgacctt     1620
ttgccgccgt cagctcacgg gctacaaagt accgaagctg gtggagtttc gtgatgagtt    1680
accgaaatct aacgtcggaa aaattttgcg acgagaatta cgtgacgaag cgcgcggcaa    1740
agtggacaat aaagcctgaa agcttgcggc cgcataatgc ttaagtcgaa cagaaagtaa    1800
tcgtattgta cacggccgca taatcgaaat taatacgact cactataggg gaattgtgag    1860
cggataacaa ttccccatct tagtatatta gttaagtata agaaggagat atacatatgc    1920
gcccattaca tccgattgat tttatattcc tgtcactaga aaaagacaa cagcctatgc      1980 atgtaggtgg tttattttg tttcagattc ctgataacgc cccagacacc tttattcaag      2040
atctggtgaa tgatatccgg atatcaaaat caatccctgt tccaccattc aacaataaac     2100
tgaatgggct tttttgggat gaagatgaag agtttgattt agatcatcat tttcgtcata     2160
ttgcactgcc tcatcctggt cgtattcgtg aattgcttat ttatatttca caagagcaca    2220
gtacgctgct agatcgggca aagcccttgt ggacctgcaa tattattgaa ggaattgaag    2280
gcaatcgttt tgccatgtac ttcaaaattc accatgcgat ggtcgatggc gttgctggta    2340
tgcggttaat tgaaaaatca ctctcccatg atgtaacaga aaaagtatc gtgccacctt      2400 ggtgtgttga gggaaaacgt gcaaagcgct taagagaacc taaaacaggt aaaattaaga    2460
aaatcatgtc tggtattaag agtcagcttc aggcgacacc cacagtcatt caagagcttt    2520
ctcagacagt atttaaagat attggacgta atcctgatca tgtttcaagc tttcaggcgc    2580
```

```
cttgttctat tttgaatcag cgtgtgagct catcgcgacg ttttgcagca cagtcttttg   2640
acctagatcg ttttcgtaat attgccaaat cgttgaatgt gaccattaat gatgttgtac   2700
tagcggtatg ttctggtgca ttacgtgcgt atttgatgag tcataatagt ttgccttcaa   2760
aaccattaat tgccatggtt ccagcctcta ttcgcaatga cgattcagat gtcagcaacc   2820
gtattacgat gattctggca aatttggcaa cccacaaaga tgatccttta caacgtcttg   2880
aaattatccg ccgtagtgtt caaaactcaa agcaacgctt caaacgtatg accagcgatc   2940
agattctaaa ttatagtgct gtcgtatatg ccctgcagg actcaacata atttctggca   3000
tgatgccaaa acgccaagcc ttcaatctgg ttatttccaa tgtgcctggc caagagagc   3060 cactttactg gaatggtgcc aaacttgatg cactctaccc agcttcaatt gtattagacg   3120
gtcaagcatt gaatattaca atgaccagtt atttagataa acttgaagtt ggtttgattg   3180
catgccgtaa tgcattgcca agaatgcaga atttactgac acatttagaa gaagaaattc   3240
aactatttga aggcgtaatt gcaaagcagg aagatattaa acagccaat taaaaacaat   3300 aaacttgatt ttttaattta tcagataaaa ctaaagggct aaattagccc tcctaggctg   3360
ctgccaccgc tgagcaataa ctagcataac cccttggggc ctctaaacgg tcttgaggg   3420 gttttttgct gaaacctcag gcatttgaga agcacacggt cacactgctt ccggtagtca   3480
ataaaccggt aaaccagcaa tagacataag cggctattta acgaccctgc cctgaaccga   3540
cgaccgggtc atcgtggccg gatcttgcgg cccctcggct tgaacgaatt gttagacatt   3600
atttgccgac taccttggtg atctcgcctt tcacgtagtg gacaaattct tccaactgat   3660
ctgcgcgcga ggccaagcga tcttcttctt gtccaagata gcctgtcta gcttcaagta   3720 tgacgggctg atactgggcc ggcaggcgct ccattgccca gtcggcagcg acatccttcg   3780
gcgcgatttt gccggttact gcgctgtacc aaatgcggga caacgtaagc actacatttc   3840
gctcatcgcc agcccagtcg ggcggcgagt tccatagcgt taaggtttca tttagcgcct   3900
caaatagatc ctgttcagga accggatcaa agagttcctc cgccgctgga cctaccaagg   3960
caacgctatg ttctcttgct tttgtcagca agatagccag atcaatgtcg atcgtggctg   4020
gctcgaagat acctgcaaga atgtcattgc gctgccattc tccaaattgc agttcgcgct   4080
tagctggata acgccacgga atgatgtcgt cgtgcacaac aatggtgact tctacagcgc   4140
ggagaatctc gctctctcca ggggaagccg aagtttccaa aaggtcgttg atcaaagctc   4200
gccgcgttgt ttcatcaagc cttacggtca ccgtaaccag caaatcaata tcactgtgtg   4260
gcttcaggcc gccatccact gcggagccgt acaaatgtac ggccagcaac gtcggttcga   4320
gatggcgctc gatgacgcca actacctctg atagttgagt cgatacttcg gcgatcaccg   4380
cttccctcat actcttcctt tttcaatatt attgaagcat ttatcagggt tattgtctca   4440
tgagcggata catatttgaa tgtatttaga aaaataaaca aatagctagc tcactcggtc   4500
gctacgctcc gggcgtgaga ctgcggcggg cgctgcggac acatacaaag ttacccacag   4560
attccgtgga taagcagggg actaacatgt gaggcaaaac agcagggccg cgccggtggc   4620 gttttttccat aggctccgcc ctcctgccag agttcacata aacagacgct tttccggtgc   4680
atctgtggga gccgtgaggc tcaaccatga atctgacagt acgggcgaaa cccgacagga   4740
cttaaagatc cccaccgttt ccggcgggtc gctccctctt gcgctctcct gttccgaccc   4800
tgccgtttac cggatacctg ttccgccttt ctcccttacg ggaagtgtgg cgctttctca   4860
tagctcacac actggtatct cggctcggtg taggtcgttc gctccaagct gggctgtaag   4920
caagaactcc ccgttcagcc cgactgctgc gccttatccg gtaactgttc acttgagtcc   4980
```

```
aacccggaaa agcacggtaa aacgccactg gcagcagcca ttggtaactg ggagttcgca    5040
gaggatttgt ttagctaaac acgcggttgc tcttgaagtg tgcgccaaag tccggctaca    5100
ctggaaggac agatttggtt gctgtgctct gcgaaagcca gttaccacgg ttaagcagtt    5160
ccccaactga cttaacccttc gatcaaacca cctccccagg tggttttttc gtttacaggg    5220
caaaagatta cgcgcagaaa aaaggatct caagaagatc ctttgatctt ttctactgaa    5280
ccgctctaga tttcagtgca atttatctct tcaaatgtag cacctgaagt cagccccata    5340
cgatataagt tgtaattctc atgttagtca tgccccgcgc ccaccggaag gagctgactg    5400
ggttgaaggc tctcaagggc atcggtcgag atcccggtgc ctaatgagtg agctaactta    5460
cattaattgc gttgcgctca ctgcccgctt tccagtcggg aaacctgtcg tgccagctgc    5520
attaatgaat cggccaacgc gcggggagag cggtttgcg tattgggcgc cagggtggtt    5580
tttcttttca ccagtgagac gggcaacagc tgattgccct tcaccgcctg ccctgagag    5640 agttgcagca agcggtccac gctggttttgc cccagcaggc gaaaatcctg tttgatggtg    5700
gttaacggcg ggatataaca tgagctgtct tcggtatcgt cgtatcccac taccgagatg    5760
tccgcaccaa cgcgcagccc ggactcggta atggcgcgca ttgcgcccag cgccatctga    5820
tcgttggcaa ccagcatcgc agtgggaacg atgccctcat tcagcatttg catggtttgt    5880
tgaaaaccgg acatggcact ccagtcgcct tcccgttccg ctatcggctg aatttgattg    5940
cgagtgagat atttatgcca gccagccaga cgcagacgcg ccgagacaga acttaatggg    6000
cccgctaaca gcgcgatttg ctggtgaccc aatgcgacca gatgctccac gcccagtcgc    6060
gtaccgtctt catgggagaa aataatactg ttgatgggtg tctggtcaga gacatcaaga    6120
aataacgccg gaacattagt gcaggcagct tccacagcaa tggcatcctg gtcatccagc    6180
ggatagttaa tgatcagccc actgacgcgt tgcgcgagaa gattgtgcac cgccgcttta    6240
caggcttcga cgccgcttcg ttctaccatc gacaccacca cgctggcacc cagttgatcg    6300
gcgcgagatt taatcgccgc gacaatttgc gacggcgcgt gcagggccag actggaggtg    6360
gcaacgccaa tcagcaacga ctgtttgccc gccagttgtt gtgccacgcg gttgggaatg    6420
taattcagct ccgccatcgc cgcttccact ttttcccgcg ttttcgcaga aacgtggctc    6480
gcctggttca ccacgcggga aacggtctga taagagacac cggcatactc tgcgacatcg    6540
tataacgtta ctggtttcac attcaccacc ctgaattgac tctcttccgg gcgctatcat    6600
gccataccgc gaaaggtttt gcgccattcg atggtgtccg ggatctcgac gctctccctt    6660
atgcgactcc tgcattagga aattaatacg actcactata                          6700
```

<210> SEQ ID NO 9
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"

<400> SEQUENCE: 9
ctctagaaat aatttaactt taagtaggag auaggtaccc atggcggaca cgttattgat    60

<210> SEQ ID NO 10

```
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
cttcgaattc catttaaatt atttctagag tcattatgag tcatgattta ctaaaggc         58

<210> SEQ ID NO 11
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ctctagaaat aattttagtt aagtataaga aggagatata ccatggtgaa gaaggtttgg      60
cttaa                                                                  65

<210> SEQ ID NO 12
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
cttcgaattc catttaaatt atttctagag ttatcaggct ttattgtcca c               51

<210> SEQ ID NO 13
<211> LENGTH: 5733
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
actcaccagt cacagaaaag catcttacgg atggcatgac agtaagagaa ttatgcagtg      60
ctgccataac catgagtgat aacactgcgg ccaacttact tctgacaacg atcggaggac     120
cgaaggagct aaccgctttt tgcacaaca tgggggatca tgtaactcgc cttgatcgtt      180
gggaaccgga gctgaatgaa gccataccaa acgacgagcg tgacaccacg atgcctgcag    240
caatggcaac aacgttgcgc aaactattaa ctggcgaact acttactcta gcttcccggc    300
aacaattaat agactggatg gaggcggata agttgcagg accacttctg cgctcggccc      360
ttccggctgg ctggtttatt gctgataaat ctggagccgg tgagcgtggg tctcgcggta    420
tcattgcagc actggggcca gatggtaagc cctcccgtat cgtagttatc tacacgacgg    480
ggagtcaggc aactatggat gaacgaaata gacagatcgc tgagataggt gcctcactga    540
ttaagcattg gtaactgtca gaccaagttt actcatatat actttagatt gatttaaaac    600
ttcattttta atttaaaagg atctaggtga agatcctttt tgataatctc atgaccaaaa    660
tcccttaacg tgagttttcg ttccactgag cgtcagaccc cttaataaga tgatcttctt    720
gagatcgttt tggtctgcgc gtaatctctt gctctgaaaa cgaaaaaacc gccttgcagg    780
```

```
gcggttttc  gaaggttctc  tgagctacca  actctttgaa  ccgaggtaac  tggcttggag    840
gagcgcagtc  accaaaactt  gtcctttcag  tttagcctta  accggcgcat  gacttcaaga    900
ctaactcctc  taaatcaatt  accagtggct  gctgccagtg  gtgcttttgc  atgtctttcc    960
gggttggact  caagacgata  gttaccggat  aaggcgcagc  ggtcggactg  aacgggggt   1020 tcgtgcatac  agtccagctt  ggagcgaact  gcctacccgg  aactgagtgt  caggcgtgga   1080
atgagacaaa  cgcggccata  acagcggaat  gacaccggta  aaccgaaagg  caggaacagg   1140
agagcgcacg  agggagccgc  caggggaaa  cgcctggtat  ctttatagtc  ctgtcgggtt    1200
tcgccaccac  tgatttgagc  gtcagatttc  gtgatgcttg  tcagggggc  ggagcctatg    1260 gaaaaacggc  tttgccgcgg  ccctctcact  tccctgttaa  gtatcttcct  ggcatcttcc   1320
aggaaatctc  cgccccgttc  gtaagccatt  tccgctcgcc  gcagtcgaac  gaccgagcgt   1380
agcgagtcag  tgagcgagga  agcggaatat  atcctgtatc  acatattctg  ctgacgcacc   1440
ggtgcagcct  tttttctcct  gccacatgaa  gcacttcact  gacaccctca  tcagtgccaa   1500
catagtaagc  cagtatacac  tccgctagcg  ctgaggtctg  cctcgtgaag  aaggtgttgc   1560
tgactcatac  caggcctgaa  tcgccccatc  atccagccag  aaagtgaggg  agccacggtt   1620
gatgagagct  ttgttgtagg  tggaccagtt  ggtgattttg  aactttgct  ttgccacgga    1680 acggtctgcg  ttgtcgggaa  gatgcgtgat  ctgatccttc  aactcagcaa  aagttcgatt   1740
tattcaacaa  agccacgttg  tgtctcaaaa  tctctgatgt  tacattgcac  aagataaaaa   1800
tatatcatca  tgaacaataa  aactgtctgc  ttacataaac  agtaatacaa  ggggtgttat   1860
gagccatatt  caacgggaaa  cgtcttgctc  gaggccgcga  ttaaattcca  acatggatgc   1920
tgatttatat  gggtataaat  gggctcgcga  taatgtcggg  caatcaggtg  cgacaatcta   1980
tcgattgtat  gggaagcccg  atgcgccaga  gttgtttctg  aaacatggca  aaggtagcgt   2040
tgccaatgat  gttacagatg  agatggtcag  actaaactgg  ctgacggaat  ttatgcctct   2100
tccgaccatc  aagcatttta  tccgtactcc  tgatgatgca  tggttactca  ccactgcgat   2160
ccccgggaaa  acagcattcc  aggtattaga  agaatatcct  gattcaggtg  aaaatattgt   2220
tgatgcgctg  gcagtgttcc  tgcgccggtt  gcattcgatt  cctgtttgta  attgtccttt   2280
taacagcgat  cgcgtatttc  gtctcgctca  ggcgcaatca  cgaatgaata  acggtttggt   2340
tgatgcgagt  gattttgatg  acgagcgtaa  tggctggcct  gttgaacaag  tctgaaaga   2400 aatgcataag  cttttgccat  tctcaccgga  ttcagtcgtc  actcatggtg  atttctcact   2460
tgataacctt  atttttgacg  aggggaaatt  aataggttgt  attgatgttg  gacgagtcgg   2520
aatcgcagac  cgataccagg  atcttgccat  cctatggaac  tgcctcggtg  agttttctcc   2580
ttcattacag  aaacggcttt  ttcaaaaata  tggtattgat  aatcctgata  tgaataaatt   2640
gcagtttcat  ttgatgctcg  atgagttttt  ctaatcagaa  ttggttaatt  ggttgtaaca   2700
ctggcagagc  attacgctga  cttgacggga  cggcggcttt  gttgaataaa  tcgaactttt   2760
gctgagttga  aggatcagat  cacgcatctt  cccgacaacg  cagaccgttc  cgtggcaaag   2820
caaaagttca  aaatcaccaa  ctggtccacc  tacaacaaag  ctctcatcaa  ccgtggctcc   2880
ctcactttct  ggctggatga  tggggcgatt  caggcctggt  atgagtcagc  aacaccttct   2940
tcacgaggca  gacctcagcg  ctcaaagatg  cagggtaaa  agctaaccgc  atctttaccg   3000
acaaggcatc  cggcagttca  acagatcggg  aaggctggaa  tttgctgagg  atgaaggtgg   3060
aggaaggtga  tgtcattctg  gtgaagaagc  tcgaccgtct  tggccgcgac  accgccgaca   3120
```

```
tgatccaact gataaaagag tttgatgctc agggtgtagc ggttcggttt attgacgacg    3180
ggatcagtac cgacggtgat atggggcaaa tggtggtcac catcctgtcg gctgtggcac    3240
aggctgaacg ccggaggatc ctagagcgca cgaatgaggg ccgacaggaa gcaaagctga    3300
aaggaatcaa atttggccgc aggcgtaccg tggacaggaa cgtcgtgctg acgcttcatc    3360
agaagggcac tggtgcaacg gaaattgctc atcagctcag tattgcccgc tccacggttt    3420
ataaaattct tgaagacgaa agggcctcgt gatacgccta tttttatagg ttaatgtcat    3480
gataataatg gtttcttaga cgtcttaatt aatcaggaga gcgttcaccg acaaacaaca    3540
gataaaacga aaggcccagt ctttcgactg agcctttcgt tttatttgat gcctggcagt    3600
tccctactct cgcatgggga accccacac taccatcggc gctacggcgt ttcacttctg    3660
agttcggcat ggggtcaggt gggaccaccg cgctactgcc gccaggcaaa ttctgtttta    3720
tcagaccgct tctgcgttct gatttaatct gtatcaggct gaaaatcttc tctcatccgc    3780
caaaacagcc aagctggaga ccgtttaaac tcaatgatga tgatgatgat ggtcgacggc    3840
gctattcaga tcctcttctg agatgagttt ttgttcgggc ccaagcttcg aattcccata    3900
tggtaccagc tgcagatctc gagctcggat ccatggttta ttcctcctta tttaatcgat    3960
acattaatat atacctcttt aattttaat aataaagtta atcgataatt ccggtcgagt    4020
gcccacacag attgtctgat aaattgttaa agagcagtgc cgcttcgctt tttctcagcg    4080
gcgctgtttc ctgtgtgaaa ttgttatccg ctcacaattc cacacattat acgagccgga    4140
tgattaattg tcaacagctc atttcagaat atttgccaga accgttatga tgtcggcgca    4200
aaaaacatta tccagaacgg gagtgcgcct tgagcgacac gaattatgca gtgatttacg    4260
acctgcacag ccataccaca gcttccgatg gctgcctgac gccagaagca ttggtgcacc    4320
gtgcagtcga tgataagctg tcaaaccaga tcaattcgcg ctaactcaca ttaattgcgt    4380
tgcgctcact gcccgctttc cagtcgggaa acctgtcgtg ccagctgcat taatgaatcg    4440
gccaacgcgc ggggagaggc ggtttgcgta ttgggcgcca gggtggtttt cttttcacc    4500 agtgagacgg gcaacagctg attgcccttc accgcctggc cctgagagag ttgcagcaag    4560
cggtccacgc tggtttgccc cagcaggcga aaatcctgtt tgatggtggt tgacggcggg    4620
atataacatg agctgtcttc ggtatcgtcg tatcccacta ccgagatatc cgcaccaacg    4680
cgcagcccgg actcggtaat ggcgcgcatt gcgcccagcg ccatctgatc gttggcaacc    4740
agcatcgcag tgggaacgat gccctcattc agcatttgca tggtttgttg aaaaccggac    4800
atggcactcc agtcgccttc ccgttccgct atcggctgaa tttgattgcg agtgagatat    4860
ttatgccagc cagccagacg cagacgcgcc gagacagaac ttaatgggcc cgctaacagc    4920
gcgatttgct ggtgacccaa tgcgaccaga tgctccacgc ccagtcgcgt accgtcttca    4980
tgggagaaaa taatactgtt gatgggtgtc tggtcagaga catcaagaaa taacgccgga    5040
acattagtgc aggcagcttc cacagcaatg gcatcctggt catccagcgg atagttaatg    5100
atcagcccac tgacgcgttg cgcgagaaga ttgtgcaccg ccgctttaca ggcttcgacg    5160
ccgcttcgtt ctaccatcga caccaccacg ctggcaccca gttgatcggc gcgagattta    5220
atcgccgcga caatttgcga cggcgcgtgc agggccagac tggaggtggc aacgccaatc    5280
agcaacgact gtttgcccgc cagttgttgt gccacgcggt tgggaatgta attcagctcc    5340
gccatcgccg cttccacttt ttcccgcgtt ttcgcagaaa cgtggctggc ctggttcacc    5400
acgcgggaaa cggtctgata agagacaccg gcatactctg cgacatcgta taacgttact    5460
ggtttcacat tcaccaccct gaattgactc tcttccgggc gctatcatgc cataccgcga    5520
```

```
aaggttttgc accattcgat ggtgtcaacg taaatgcatg ccgcttcgcc ttcgcgcgcg      5580
aattgatctg ctgcctcgcg cgtttcggtg atgacggtga aaacctctga cacatgcagc      5640
tcccggagac ggtcacagct tgtctgtaag cggatgccgg gagcagacaa gcccgtcagg      5700
gcgcgtcagc gggtgttggc ggggccggcc tcg                                   5733

<210> SEQ ID NO 14
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
gggtcaatag cggccgccaa ttcgcgcgcg aaggcg                                36

<210> SEQ ID NO 15
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
tggcgcgcct cctagggcat tacgctgact tgacggg                               37

<210> SEQ ID NO 16
<211> LENGTH: 15179
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
ggccacgatg cgtccggcgt agaggatctg ctcatgtttg acagcttatc atcgatgcat      60
aatgtgcctg tcaaatggac gaagcaggga ttctgcaaac cctatgctac tccgtcaagc     120
cgtcaattgt ctgattcgtt accaattatg acaacttgac ggctacatca ttcactttt     180 cttcacaacc ggcacggaac tcgctcgggc tggccccggt gcattttta atacccgcg      240 agaaatagag ttgatcgtca aaccaacat tgcgaccgac ggtggcgata ggcatccggg      300
tggtgctcaa aagcagcttc gcctggctga tacgttggtc ctcgcgccag cttaagacgc      360
taatccctaa ctgctggcgg aaaagatgtg acagacgcga cggcgacaag caaacatgct      420
gtgcgacgct ggcgatatca aaattgctgt ctgccaggtg atcgctgatg tactgacaag      480
cctcgcgtac ccgattatcc atcggtggat ggagcgactc gttaatcgct tccatgcgcc      540
gcagtaacaa ttgctcaagc agatttatcg ccagcagctc cgaatagcgc ccttccccttt      600 gcccggcgtt aatgatttgc ccaaacaggt cgctgaaatg cggctggtgc gcttcatccg      660
ggcgaaagaa cccccgtattg gcaaatattg acggccagtt aagccattca tgccagtagg      720
cgcgcggacg aaagtaaacc cactggtgat accattcgcg agcctccgga tgacgaccgt      780
agtgatgaat ctctcctggc gggaacagca aaatatcacc cggtcggcaa acaaattctc      840
gtccctgatt tttcaccacc ccctgaccgc gaatggtgag attgagaata taaccctttca      900
```

```
ttcccagcgg tcggtcgata aaaaaatcga gataaccgtt ggcctcaatc ggcgttaaac     960
ccgccaccag atgggcatta acgagtatc ccggcagcag gggatcattt tgcgcttcag    1020
ccatactttt catactcccg ccattcagag aagaaaccaa ttgtccatat tgcatcagac   1080
attgccgtca ctgcgtcttt tactggctct tctcgctaac caaaccggta accccgctta   1140
ttaaaagcat tctgtaacaa agcgggacca aagccatgac aaaaacgcgt aacaaaagtg   1200
tctataatca cggcagaaaa gtccacattg attatttgca cggcgtcaca ctttgctatg   1260
ccatagcatt tttatccata agattagcgg atcctacctg acgcttttta tcgcaactct   1320
ctactgtttc tccataccg ttttttttggg ctagcgaatt cgagctcggt acccaagtct   1380
taaactagac agaatagttg taaactgaaa tcagtccagt tatgctgtga aaaagcatac   1440
tggacttttg ttatggctaa agcaaactct tcattttctg aagtgcaaat tgcccgtcgt   1500 attaagagg ggcgtggcca agggcatggt aaagactata ttccatggct aacagtacaa    1560
gaagttcctt cttcaggtcg ttcccaccgt atttattctc ataagacggg acgagtccat   1620
catttgctat ctgacttaga gcttgctgtt tttctcagtc ttgagtggga gagcagcgtg   1680
ctagatatac gcgagcagtt ccccttatta cctagtgata ccaggcagat tgcaatagat   1740
agtggtatta agcatcctgt tattcgtggt gtagatcagg ttatgtctac tgattttta    1800 gtggactgca aagatggtcc ttttgagcag tttgctattc aagtcaaacc tgcagcagcc   1860
ttacaagacg agcgtacctt agaaaaacta gaactagagc gtcgctattg gcagcaaaag   1920
caaattcctt ggttcatttt tactgataaa gaaataaatc ccgtagtaaa agaaaatatt   1980
gaatggcttt attcagtgaa aacagaagaa gtttctgcgg agcttttagc acaactatcc   2040
ccattggccc atatcctgca agaaaaagga gatgaaaaca ttatcaatgt ctgtaagcag   2100
gttgatattg cttatgattt ggagttaggc aaaacattga gtgagatacg agccttaacc   2160
gcaaatggtt ttattaagtt caatatttat aagtctttca gggcaaataa gtgtgcagat   2220
ctctgtatta gccaagtagt gaatatggag gagttgcgct atgtggcaaa ttaatgaggt   2280 tgtgctatt gataatgatc cgtatcgcat tttggctata gaggatggcc aagttgtctg    2340
gatgcaaata agcgctgata aaggagttcc acaagctagg gctgagttgt tgctaatgca   2400
gtatttagat gaaggccgct tagttagaac tgatgaccct tatgtacatc ttgatttaga   2460
agagccgtct gtagattctg tcagcttcca gaagcgcgag gaggattatc gaaaaattct   2520
tcctattatt aatagtaagg atcgtttcga ccctaaagtc agaagcgaac tcgttgagca   2580
tgtggtccaa gaacataagg ttactaaggc tacagtttat aagttgttac gccgttactg   2640
gcagcgtggt caaacgccta atgcattaat tcctgactac aaaaacagcg gtgcaccagg   2700
ggaaagacgt tcagcgacag gaacagcaaa gattggccga ccagagaat atggtaaggg    2760 tgaaggaacc aaggtaacgc ccgagattga acgcctttt aggttgacca tagaaaagca    2820
cctgttaaat caaaaggta caaagaccac cgttgcctat agacgatttg tggacttgtt    2880
tgctcagtat tttcctcgca ttccccaaga ggattaccca acactacgtc agtttcgtta   2940 ttttttatgat cgagaatacc ctaaagctca gcgcttaaag tctagagtta agcaggggt    3000 atataaaaaa gacgtacgac ccttaagtag tacagccact tctcaggcgt taggccctgg   3060
gagtcgttat gagattgatg ccacgattgc tgatatttat ttagtggatc atcatgatcg   3120 ccaaaaatc ataggaagac caacgcttta cattgtgatt gatgtgttta gtcggatgat    3180
cacgggcttt tatatcggct ttgaaaatcc gtccttatgtg gtggcgatgc aggcttttgt   3240
aaatgcttgc tctgacaaaa cggccatttg tgcccagcat gatattgaga ttagtagctc   3300
```

```
agactggccg tgtgtaggtt tgccagatgt gttgctagcg gaccgtggcg aattaatgag    3360
tcatcaggtc gaagccttag tttctagttt taatgtgcga gtggaaagtg ctccacctag    3420
acgtggcgat gctaaaggca tagtggaaag cacttttaga acactacaag ccgagtttaa    3480
gtcctttgca cctggcattg tagagggcag tcggatcaaa agccatggtg aaacagacta    3540
taggttagat gcatctctgt cggtatttga gttcacacaa attattttgc gtacgatctt    3600
attcagaaat aaccatctgg tgatggataa atacgatcga gatgctgatt ttcctacaga    3660
tttaccgtct attcctgtcc agctatggca atgggg tatg cagcatcgta caggtagttt    3720
aagggctgtg gagcaagagc agttgcgagt agcgttactg cctcgccgaa aggtctctat    3780
ttcttcattt ggcgttaatt tgtggggttt gtattactcg gggtcagaga ttctgcgtga    3840
gggttggttg cagcggagca ctgatatagc tagacctcaa catttagaag cggcttatga    3900
cccagtgctg gttgatacga tttatttgtt tccgcaagtt ggcagccgtg tattttggcg    3960
ctgtaatctg acggaacgta gtcggcagtt taaaggtctc tcattttggg aggtttggga    4020
tatacaagca caagaaaaac acaataaagc caatgcgaag caggatgagt taactaaacg    4080
cagggagctt gaggcgttta ttcagcaaac cattcagaaa gcgaataagt taacgcccag    4140
tactactgag cccaaatcaa cacgcattaa gcagattaaa actaataaaa agaagccgt     4200 gacctcggag cgtaaaaaac gtgcggagca tttgaagcca agctcttcag gtgatgaggc    4260
taaagttatt cctttcaacg cagtggaagc ggatgatcaa gaagattaca gcctacccac    4320
atacgtgcct gaattattc aggatccacc agaaaaggat gagtcatgag tgctacccgg    4380
attcaagcag tttatcgtga tacgggggta gaggcttatc gtgataatcc ttttatcgag    4440
gccttaccac cattcaagaa gtcagtgaat agtgctgcat cactgaaatc ctctttacag    4500
cttacttcct ctgacttgca aaagtcccgt gttatcagag ctcataccat tgtcgtatt     4560 ccagatgact attttcagcc attaggtacg catttgctac taagtgagcg tatttcggtc    4620
atgattcgag gtggctacgt aggcagaaat cctaaaacag gagatttaca aaagcattta    4680
caaaatggtt atgagcgtgt tcaaacggga gagttggaga catttcgctt tgaggaggca    4740
cgatctacgg cacaaagctt attgttaatt ggttgttctg gtagtgggaa gacgacctct    4800
cttcatcgta ttctagccac gtatcctcag gtgatttacc atcgtgaact caatgtagag    4860
caggtggtgt atttgaaaat agactgctcg cataatggtt cgctaaaaga aatctgcttg    4920
aatttttcca gagcgttgga tcgagccttg ggctcgaact atgagcgtcg ttatggctta    4980
aaacgtcatg gtatagaaac catgttggct ttgatgtcgc aaatagccaa tgcacatgct    5040
ttagggttgt tggttattga tgaaattcag catttaagcc gctctcgttc gggtggatct    5100
caagagatgc tgaactttt tgtgacgatg gtgaatatta ttggcgtacc agtgatgttg    5160
attggtaccc ctaaagcacg agagattttt gaggctgatt tgcggtctgc acgtagaggg    5220
gcagggtttg gagctatatt ctgggatcct atacaacaaa cgcaacgtgg aaagcccaat    5280
caagagtgga tcgcttttac ggataatctt tggcaattac agcttttaca acgcaaagat    5340
gcgctgttat cggatgaggt ccgtgatgtg tggtatgagc taagccaagg agtgatggac    5400
attgtagtaa aacttttgt actcgctcag ctccgtgcgc tagctttagg caatgagcgt    5460
attaccgctg gtttattgcg gcaagtgtat caagatgagt taaagcctgt gcaccccatg    5520
ctagaggcat tacgctcggg tatcccagaa cgcattgctc gttattctga tctagtcgtt    5580
cccgagattg ataaacggtt aatccaactt cagctagata tcgcagcgat acaagaacaa    5640
```

```
acaccagaag aaaaagccct tcaagagtta gataccgaag atcagcgtca tttatatctg    5700
atgctgaaag aggattacga ttcaagcctg ttaattccca ctattaaaaa agcgtttagc    5760
cagaatccaa cgatgacaag acaaaagtta ctgcctcttg ttttgcagtg gttgatggaa    5820
ggcgaaacgg tagtgtcaga actagaaaag ccctccaaga gtaaaaaggt ttcggctata    5880
aaggtagtca agcccagcga ctgggatagc ttgcctgata cggatttacg ttatatctat    5940
tcacaacgcc aacctgaaaa aaccatgcat gaacggttaa aagggaaagg ggtaatagtg    6000
gatatggcga gcttatttaa acaagcaggt tagccatgag aaactttcct gttccgtact    6060
cgaatgagct gatttatagc actattgcac gggcaggcgt ttatcaaggg attgttagtc    6120
ctaagcagct gttggatgag gtgtatggca accgcaaggt ggtcgctacc ttaggtctgc    6180
cctcgcattt aggtgtgata gcaagacatc tacatcaaac aggacgttac gctgttcagc    6240
agcttattta tgagcatacc ttattccctt tatatgctcc gtttgtaggc aaggagcgcc    6300
gagacgaagc tattcggtta atggagtacc aagcgcaagg tgcggtgcat taatgctag    6360 gagtcgctgc ttctagagtt aagagcgata accgctttag atactgccct gattgcgttg    6420
ctcttcagct aaataggtat ggggaagcct tttggcaacg agattggtat ttgcccgctt    6480
tgccatattg tccaaaacac ggtgcttag tcttctttga tagagctgta gatgatcacc     6540
gacatcaatt tgggctttg ggtcatactg agctgctttc agactacccc aaagactccc     6600
tatctcaatt aacagcacta gctgcttata tagcccctct gttagatgct ccacgagcgc    6660
aagagctttc cccaagcctt gagcagtgga cgctgtttta tcagcgctta gcgcaggatc    6720
tagggctaac caaaagcaag cacattcgtc atgacttggt ggcggagaga gtgaggcaga    6780
cttttagtga tgaggcacta gagaaactgg atttaaagtt ggcagagaac aaggacacgt    6840
gttggctgaa aagtatattc cgtaagcata gaaaagcctt tagttattta cagcatagta    6900
ttgtgtggca agccttattg ccaaaactaa cggttataga agcgctacag caggcaagtg    6960
ctcttactga gcactctata acgacaagac ctgttagcca gtctgtgcaa cctaactctg    7020
aagatttatc tgttaagcat aaagactggc agcaactagt gcataaatac caaggaatta    7080
aggcggcaag acagtctta gagggtgggg tgctatacgc ttggctttac cgacatgaca     7140
gggattggct agttcactgg aatcaacagc atcaacaaga gcgtctggca cccgccccta    7200
gagttgattg gaaccaaaga gatcgaattg ctgtacgaca actattaaga atcataaagc    7260
gtctagatag tagccttgat cacccaagag cgacatcgag ctggctgtta aagcaaactc    7320
ctaacggaac ctctcttgca aaaaatctac agaaactgcc tttggtagcg ctttgcttaa    7380
agcgttactc agagagtgtg aagattatc aaattagacg gattagccaa gcttttatta    7440
agcttaaaca ggaagatgtt gagcttaggc gctggcgatt attaagaagt gcaacgttat    7500
ctaaagagcg ataactgag gaagcacaaa gattcttgga aatggtttat ggggaagagt      7560
gagtggttag gctagctaca tttaatgaca atgtgcaggt tgtacatatt ggtcatttat     7620
tccgtaactc gggtcataag gagtggcgta tttttgtttg gtttaatcca atgcaagaac    7680
ggaaatggac tcgatttact catttgcctt tattaagtcg agctaaggtg gttaacagta    7740
caacaaagca aataataag gcggatcgtg tgattgagtt tgaagcatcg atcttcaac      7800 gagccaaaat aatcgatttt cctaatctct cgtcctttgc ttccgtacgc aacaaggatg    7860
gagcgcagag ttcatttatt tacgaagctg aaacaccata tagcaagact cgttatcaca    7920
tcccacagtt agagctagct cggtcattat ttttagggga tcctctagag tcgacctgca    7980
ggcatgcaag cttggctgtt ttggcggatg agagaagatt ttcagcctga tacagattaa    8040
```

```
atcagaacgc agaagcggtc tgataaaaca gaatttgcct ggcggcagta gcgcggtggt    8100
cccacctgac cccatgccga actcagaagt gaaacgccgt agcgccgatg gtagtgtggg    8160
gtctccccat gcgagagtag ggaactgcca ggcatcaaat aaaacgaaag gctcagtcga    8220
aagactgggc ctttcgtttt atctgttgtt tgtcggtgaa cgctctcctg agtaggacaa    8280
atccgccggg agcggatttg aacgttgcga agcaacggcc cggagggtgg cgggcaggac    8340
gcccgccata aactgccagg catcaaatta agcagaaggc catcctgacg gatggccttt    8400
ttgcgtttct acaaactctt ttgtttattt tctaaatac attcaaatat gtatccgctc    8460
atgagacaat aaccctgata aatgcttcaa taatattgaa aaaggaagag tatgagtatt    8520
caacatttcc gtgtcgccct tattcccttt tttgcggcat tttgccttcc tgttttttgct   8580 cacccagaaa cgctggtgaa agtaaaagat gctgaagatc agttgggtgc acgagtgggt   8640
tacatcgaac tggatctcaa cagcggtaag atccttgaga gttttcgccc cgaagaacgt    8700
tttccaatga tgagcacttt taaagttctg ctatgtggcg cggtattatc ccgtgttgac    8760
gccgggcaag agcaactcgg tcgccgcata cactattctc agaatgactt ggttgagtac    8820
tcaccagtca cagaaaagca tcttacggat ggcatgacag taagagaatt atgcagtgct    8880
gccataacca tgagtgataa cactgcggcc aacttacttc tgacaacgat cggaggaccg    8940
aaggagctaa ccgctttttt gcacaacatg ggggatcatg taactcgcct tgatcgttgg    9000
gaaccggagc tgaatgaagc cataccaaac gacgagcgtg acaccacgat gcctgcagca    9060
atggcaacaa cgttgcgcaa actattaact ggcgaactac ttactctagc ttcccggcaa    9120
caattaatag actggatgga ggcggataaa gttgcaggac cacttctgcg ctcggccctt    9180
ccggctggct ggtttattgc tgataaatct ggagccggtg agcgtgggtc tcgcggtatc    9240
attgcagcac tggggccaga tggtaagccc tcccgtatcg tagttatcta cacgacgggg    9300
agtcaggcaa ctatggatga acgaaataga cagatcgctg agataggtgc ctcactgatt    9360
aagcattggt aactgtcaga ccaagtttac tcatatatac tttagattga tttacgcgcc    9420
ctgtagcggc gcattaagcg cggcgggtgt ggtggttacg cgcagcgtga ccgctacact    9480
tgccagcgcc ctagcgcccg ctcctttcgc tttcttccct cctttctcg ccacgttcgc    9540 cgccggccag cctcgcagag caggattccc gttgagcacc gccaggtgcg aataagggac    9600
agtgaagaag gaacacccgc tcgcgggtgg gcctacttca cctatcctgc ccggcggcat    9660
caccggcgcc acaggtgcgg ttgctggcgc ctatatcgcc gacatcaccg atggggaaga    9720
tcgggctcgc cacttcgggc tcatgagcgc ttgtttcggc gtgggtatgg tggcaggccc    9780
cgtggccggg ggactgttgg gcgccatctc cttgcatgca ccattccttg cggcggcggt    9840
gctcaacggc ctcaacctac tactgggctg cttcctaatg caggagtcgc ataagggaga    9900
gcgtcgatcc ccgacagtaa gacgggtaag cctgttgatg ataccgctgc cttactgggt    9960
gcattagcca gtctgaatga cctgtcacgg gataatccga agtggtcaga ctggaaaatc    10020
agagggcagg aactgctgaa cagcaaaaag tcagatagca ccacatagca gacccgccat    10080
aaaacgccct gagaagcccg tgacgggctt tcttgtatt atgggtagtt tccttgcatg    10140
aatccataaa aggcgcctgt agtgccattt accccccattc actgccagag ccgtgagcgc    10200
agcgaactga atgtcacgaa aaagacagcg actcaggtgc ctgatggtcg agacaaaag    10260 gaatattcag cgatttgccc gagccttgcga gggtgctact taagccttta gggttttaag    10320
gtctgttttg tagaggagca aacagcgttt gcgacatcct tttgtaatac tgcggaactg    10380
```

```
actaaagtag tgagttatac acagggctgg gatctattct ttttatcttt ttttattctt    10440
tctttattct ataaattata accacttgaa tataaacaaa aaaaacacac aaaggtctag    10500
cggaatttac agagggtcta gcagaattta caagttttcc agcaaaggtc tagcagaatt    10560
tacagatacc cacaactcaa aggaaaagga ctagtaatta tcattgacta gcccatctca    10620
attggtatag tgattaaaat cacctagacc aattgagatg tatgtctgaa ttagttgttt    10680
tcaaagcaaa tgaactagcg attagtcgct atgacttaac ggagcatgaa accaagctaa    10740
ttttatgctg tgtggcacta ctcaaccccca cgattgaaaa ccctacaagg aaagaacgga    10800
cggtatcgtt cacttataac caatacgttc agatgatgaa catcagtagg gaaaatgctt    10860
atggtgtatt agctaaagca accagagagc tgatgacgag aactgtggaa atcaggaatc    10920
ctttggttaa aggctttgag attttccagt ggacaaacta tgccaagttc tcaagcgaaa    10980
aattagaatt agtttttagt gaagagatat tgccttatct tttccagtta aaaaaattca    11040
taaaatataa tctggaacat gttaagtctt ttgaaaacaa atactctatg aggatttatg    11100
agtggttatt aaaagaacta acacaaaaga aaactcacaa ggcaaatata gagattagcc    11160
ttgatgaatt taagttcatg ttaatgcttg aaaataacta ccatgagttt aaaaggctta    11220
accaatgggt tttgaaaacca ataagtaaag atttaaacac ttacagcaat atgaaattgg    11280
tggttgataa gcgaggccgc ccgactgata cgttgatttt ccaagttgaa ctagatagac    11340
aaatggatct cgtaaccgaa cttgagaaca accagataaa aatgaatggt gacaaaatac    11400
caacaaccat tacatcagat tcctacctac ataacggact aagaaaaaca ctacacgatg    11460
ctttaactgc aaaaattcag ctcaccagtt ttgaggcaaa attttttgagt gacatgcaaa    11520
gtaagtatga tctcaatggt tcgttctcat ggctcacgca aaaacaacga accacactag    11580
agaacatact ggctaaatac ggaaggatct gaggttctta tggctcttgt atctatcagt    11640
gaagcatcaa gactaacaaa caaaagtaga acaactgttc accgttacat atcaaaggga    11700
aaactgtcca tatgcacaga tgaaaacggt gtaaaaaaga tagatacatc agagcttttta    11760
cgagtttttg gtgcatttaa agctgttcac catgaacaga tcgacaatgt aacagatgaa    11820
cagcatgtaa cacctaatag aacaggtgaa accagtaaaa caaagcaact agaacatgaa    11880
attgaacacc tgagacaact tgttacagct caacagtcac acatagacag cctgaaacag    11940
gcgatgctgc ttatcgaatc aaagctgccg acaacacggg agccagtgac gcctcccgtg    12000
gggaaaaaat catggcaatt ctggaagaaa tagcgctttc agcctgtggg cggacaaaat    12060
agttgggaac tgggaggggt ggaaatggag ttttttaagga ttatttaggg aagagtgaca    12120
aaatagatgg gaactgggtg tagcgtcgta agctaatacg aaaattaaaa atgacaaaat    12180
agttggaac tagatttcac ttatctggtt ggtcgacact agtattaccc tgttatccct    12240
agatttaaat gatatcggat cctagtaagc cacgttttaa ttaatcagat gggtcaatag    12300
cggccgccaa ttcgcgcgcg aaggcgaagc ggcatgcatt tacgttgaca ccatcgaatg    12360
gtgcaaaacc tttcgcggta tggcatgata gcgcccggaa gagagtcaat tcagggtggt    12420
gaatgtgaaa ccagtaacgt tatacgatgt cgcagagtat gccggtgtct cttatcagac    12480
cgtttcccgc gtggtgaacc aggccagcca cgtttctgcg aaaacgcggg aaaaagtgga    12540
agcggcgatg gcggagctga attacattcc caaccgcgtg gcacaacaac tggcgggcaa    12600
acagtcgttg ctgattggcg ttgccacctc cagtctggcc ctgcacgcgc cgtcgcaaat    12660
tgtcgcggcg attaaatctc gcgccgatca actgggtgcc agcgtggtgg tgtcgatggt    12720
agaacgaagc ggcgtcgaag cctgtaaagc ggcggtgcac aatcttctcg cgcaacgcgt    12780
```

```
cagtgggctg atcattaact atccgctgga tgaccaggat gccattgctg tggaagctgc   12840
ctgcactaat gttccggcgt tatttcttga tgtctctgac cagacaccca tcaacagtat   12900
tattttctcc catgaagacg gtacgcgact gggcgtggag catctggtcg cattgggtca   12960
ccagcaaatc gcgctgttag cgggcccatt aagttctgtc tcggcgcgtc tgcgtctggc   13020
tggctggcat aaatatctca ctcgcaatca aattcagccg atagcggaac gggaaggcga   13080
ctggagtgcc atgtccggtt ttcaacaaac catgcaaatg ctgaatgagg gcatcgttcc   13140
cactgcgatg ctggttgcca acgatcagat ggcgctgggc gcaatgcgcg ccattaccga   13200
gtccgggctg cgcgttggtg cggatatctc ggtagtggga tacgacgata ccgaagacag   13260
ctcatgttat atcccgccgt caaccaccat caaacaggat tttcgcctgc tggggcaaac   13320
cagcgtggac cgcttgctgc aactctctca gggccaggcg gtgaagggca atcagctgtt   13380
gcccgtctca ctggtgaaaa gaaaaaccac cctggcgccc aatacgcaaa ccgcctctcc   13440
ccgcgcgttg ccgattcat taatgcagct ggcacgacag gtttcccgac tggaaagcgg   13500
gcagtgagcg caacgcaatt aatgtgagtt agcgcgaatt gatctggttt gacagcttat   13560
catcgactgc acggtgcacc aatgcttctg gcgtcaggca gccatcggaa gctgtggtat   13620
ggctgtgcag gtcgtaaatc actgcataat tcgtgtcgct caaggcgcac tcccgttctg   13680
gataatgttt tttgcgccga catcataacg gttctggcaa atattctgaa atgagctgtt   13740
gacaattaat catccggctc gtataatgtg tggaattgtg agcggataac aatttcacac   13800
aggaaacagc gccgctgaga aaagcgaag cggcactgct ctttaacaat ttatcagaca   13860
atctgtgtgg gcactcgacc ggaattatcg attaactta ttattaaaa ttaaagaggt   13920 atatattaat gtatcgatta aataaggagg aataaaccat ggcggacacg ttattgattc   13980
tgggtgatag cctgagcgcc gggtatcgaa tgtctgccag cgcggcctgg cctgccttgt   14040
tgaatgataa gtggcagagt aaaacgtcgg tagttaatgc cagcatcagc ggcgacacct   14100
cgcaacaagg actggcgcgc cttccggctc tgctgaaaca gcatcagccg cgttgggtgc   14160
tggttgaact gggcggcaat gacggtttgc gtggttttca gccacagcaa accgagcaaa   14220
cgctgcgcca gattttgcag gatgtcaaag ccgccaacgc tgaaccattg ttaatgcaaa   14280
tacgtctgcc tgcaaactat ggtcgccgtt ataatgaagc ctttagcgcc atttacccca   14340
aactcgccaa agagtttgat gttccgctgc tgcccttttt tatggaagag gtctacctca   14400
agccacaatg gatgcaggat gacggtattc atcccaaccg cgacgcccag ccgtttattg   14460
ccgactggat ggcgaagcag ttgcagcctt tagtaaatca tgactcataa tgactctaga   14520 aataattaa atggaattcg aagcttgggc ccgaacaaaa actcatctca gaagaggatc   14580
tgaatagcgc cgtcgaccat catcatcatc atcattgagt ttaaacggtc tccagcttgg   14640
ctgttttggc ggatgagaga agattttcag cctgatacag attaaatcag aacgcagaag   14700
cggtctgata aaacagaatt tgcctggcgg cagtagcgcg gtggtcccac ctgaccccat   14760
gccgaactca gaagtgaaac gccgtagcgc cgatggtagt gtggggtctc cccatgcgag   14820
agtagggaac tgccaggcat caaataaaac gaaaggctca gtcgaaagac tgggcctttc   14880
gttttatctg ttgtttgtcg gtgaacgctc tcctgattaa ttaagacgtc ccgtcaagtc   14940
agcgtaatgc cctaggaggc gccacggc cgcgtcgacc ccacgcccct ctttaatacg   15000
acgggcaatt tgcacttcag aaaatgaaga gtttgctta gccataacaa agtccagta   15060 tgcttttttca cagcataact ggactgattt cagtttacaa ctattctgtc tagtttaaga   15120
```
ctttattgtc atagtttaga tctattttgt tcagtttaag actttattgt ccgcccaca    15179

<210> SEQ ID NO 17
<211> LENGTH: 17683
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

```
ggccacgatg cgtccggcgt agaggatctg ctcatgtttg acagcttatc atcgatgcat      60
aatgtgcctg tcaaatggac gaagcaggga ttctgcaaac cctatgctac tccgtcaagc     120
cgtcaattgt ctgattcgtt accaattatg caacttgac ggctacatca ttcactttt      180
cttcacaacc ggcacggaac tcgctcgggc tggccccggt gcattttta ataccccgcg     240
agaaatagag ttgatcgtca aaccaacat tgcgaccgac ggtggcgata ggcatccggg     300
tggtgctcaa aagcagcttc gcctggctga tacgttggtc ctcgcgccag cttaagacgc     360
taatccctaa ctgctggcgg aaaagatgtg acagacgcga cggcgacaag caaacatgct     420
gtgcgacgct ggcgatatca aaattgctgt ctgccaggtg atcgctgatg tactgacaag     480
cctcgcgtac ccgattatcc atcggtggat ggagcgactc gttaatcgct tccatgcgcc     540
gcagtaacaa ttgctcaagc agatttatcg ccagcagctc cgaatagcgc ccttcccctt     600
gcccggcgtt aatgatttgc ccaaacaggt cgctgaaatg cggctggtgc gcttcatccg     660
ggcgaaagaa cccgtattg gcaaatattg acggccagtt aagccattca tgccagtagg     720
cgcgcggacg aaagtaaacc cactggtgat accattcgcg agcctccgga tgacgaccgt     780
agtgatgaat ctctcctggc gggaacagca aaatatcacc cggtcggcaa acaaattctc     840
gtccctgatt tttcaccacc ccctgaccgc gaatggtgag attgagaata taaccttcca     900
ttcccagcgg tcggtcgata aaaaaatcga gataaccgtt ggcctcaatc ggcgttaaac     960
ccgccaccag atgggcatta acgagtatc ccggcagcag gggatcattt gcgcttcag    1020
ccatactttt catactcccg ccattcagag aagaaaccaa ttgtccatat tgcatcagac    1080
attgccgtca ctgcgtcttt tactggctct tctcgctaac caaaccggta accccgctta    1140
ttaaaagcat tctgtaacaa agcgggacca agccatgac aaaaacgcgt aacaaaagtg    1200
tctataatca cggcagaaaa gtccacattg attatttgca cggcgtcaca ctttgctatg    1260
ccatagcatt tttatccata agattagcgg atcctacctg acgcttttta tcgcaactct    1320
ctactgtttc tccatacccg ttttttgggg ctagcgaatt cgagctcggt acccaagtct    1380
taaactagac agaatagttg taaactgaaa tcagtccagt tatgctgtga aaaagcatac    1440
tggactttg ttatggctaa agcaaactct tcattttctg aagtgcaaat tgcccgtcgt    1500
attaaagagg ggcgtggcca agggcatggt aaagactata ttccatggct aacagtacaa    1560
gaagttcctt cttcaggtcg ttcccaccgt atttattctc ataagacggg acgagtccat    1620
catttgctat ctgacttaga gcttgctgtt tttctcagtc ttgagtggga gagcagcgtg    1680
ctagatatac gcgagcagtt ccccttatta cctagtgata ccaggcagat tgcaatagat    1740
agtggtatta agcatcctgt tattcgtggt gtagatcagg ttatgtctac tgattttta    1800
gtggactgca aagatggtcc ttttgagcag tttgctattc aagtcaaacc tgcagcagcc    1860
ttacaagacg agcgtacctt agaaaaacta gaactagagc gtcgctattg gcagcaaaag    1920
caaattcctt ggttcatttt tactgataaa gaaataaatc ccgtagtaaa agaaaatatt    1980
```

```
gaatggcttt attcagtgaa aacagaagaa gtttctgcgg agcttttagc acaactatcc    2040
ccattggccc atatcctgca agaaaaagga gatgaaaaca ttatcaatgt ctgtaagcag    2100
gttgatattg cttatgattt ggagttaggc aaaacattga gtgagatacg agccttaacc    2160
gcaaatggtt ttattaagtt caatatttat aagtctttca gggcaaataa gtgtgcagat    2220
ctctgtatta gccaagtagt gaatatggag gagttgcgct atgtggcaaa ttaatgaggt    2280
tgtgctattt gataatgatc cgtatcgcat tttggctata gaggatgcc aagttgtctg    2340 gatgcaaata agcgctgata aaggagttcc acaagctagg gctgagttgt tgctaatgca    2400
gtatttagat gaaggccgct tagttagaac tgatgaccct tatgtacatc ttgatttaga    2460
agagccgtct gtagattctg tcagcttcca gaagcgcgag gaggattatc gaaaaattct    2520
tcctattatt aatagtaagg atcgtttcga ccctaaagtc agaagcgaac tcgttgagca    2580
tgtggtccaa gaacataagg ttactaaggc tacagtttat aagttgttac gccgttactg    2640
gcagcgtggt caaacgccta atgcattaat tcctgactac aaaaacagcg gtgcaccagg    2700
ggaaagacgt tcagcgacag gaacagcaaa gattggccga gccagagaat atggtaaggg    2760
tgaaggaacc aaggtaacgc ccgagattga acgcctttt aggttgacca tagaaaagca    2820
cctgttaaat caaaaaggta caaagaccac cgttgcctat agacgatttg tggacttgtt    2880
tgctcagtat tttcctcgca ttccccaaga ggattaccca acactacgtc agtttcgtta    2940 ttttatgat cgagaatacc ctaaagctca gcgcttaaag tctagagtta aagcagggt     3000 atataaaaa gacgtacgac ccttaagtag tacagccact tctcaggcgt taggccctgg    3060
gagtcgttat gagattgatg ccacgattgc tgatatttat ttagtggatc atcatgatcg    3120
ccaaaaaatc ataggaagac caacgcttta cattgtgatt gatgtgttta gtcggatgat    3180
cacgggcttt tatatcggct ttgaaaatcc gtcttatgtg gtggcgatgc aggcttttgt    3240
aaatgcttgc tctgacaaaa cggccattg tgcccagcat gatattgaga ttagtagctc    3300
agactggccg tgtgtaggtt tgccagatgt gttgctagcg gaccgtggcg aattaatgag    3360
tcatcaggtc gaagccttag tttctagttt taatgtgcga gtggaaagtg ctccacctag    3420
acgtggcgat gctaaaggca tagtggaaag cacttttaga acactacaag ccgagtttaa    3480
gtcctttgca cctggcattg tagagggcag tcggatcaaa agccatggtg aaacagacta    3540
taggttagat gcatctctgt cggtatttga gttcacacaa attattttgc gtacgatctt    3600
attcagaaat aaccatctgg tgatggataa atacgatcga gatgctgatt ttcctacaga    3660
tttaccgtct attcctgtcc agctatgca atggggtatg cagcatcgta caggtagttt    3720
aagggctgtg gagcaagagc agttgcgagt agcgttactg cctcgccgaa aggtctctat    3780
ttcttcattt ggcgttaatt tgtgggttt gtattactcg gggtcagaga ttctgcgtga    3840
gggttggttg cagcggagca ctgatatagc tagacctcaa catttagaag cggcttatga    3900
cccagtgctg gttgatacga tttatttgtt tccgcaagtt ggcagccgtg tattttggcg    3960
ctgtaatctg acggaacgta gtcggcagtt taaaggtctc tcattttggg aggtttggga    4020
tatacaagca caagaaaaac acaataaagc caatgcgaag caggatgagt taactaaacg    4080
cagggagctt gaggcgtta ttcagcaaac cattcagaaa gcgaataagt taacgcccag    4140
tactactgag cccaaatcaa cacgcattaa gcagattaaa actaataaaa agaagccgt     4200 gacctcggag cgtaaaaaac gtgcggagca tttgaagcca agctcttcag gtgatgaggc    4260
taaagttatt cctttcaacg cagtggaagc ggatgatcaa gaagattaca gcctacccac    4320
```

```
atacgtgcct gaattatttc aggatccacc agaaaaggat gagtcatgag tgctacccgg      4380
attcaagcag tttatcgtga tacggggta gaggcttatc gtgataatcc ttttatcgag       4440
gccttaccac cattacaaga gtcagtgaat agtgctgcat cactgaaatc ctctttacag      4500
cttacttcct ctgacttgca aaagtcccgt gttatcagag ctcataccat ttgtcgtatt     4560
ccagatgact atttttcagcc attaggtacg catttgctac taagtgagcg tatttcggtc    4620
atgattcgag gtggctacgt aggcagaaat cctaaaacag gagatttaca aaagcattta    4680
caaaatggtt atgagcgtgt tcaaacggga gagttggaga catttcgctt tgaggaggca    4740
cgatctacgg cacaaagctt attgttaatt ggttgttctg gtagtgggaa gacgacctct    4800
cttcatcgta ttctagccac gtatcctcag gtgatttacc atcgtgaact caatgtagag    4860
caggtggtgt atttgaaaat agactgctcg cataatggtt cgctaaaaga aatctgcttg    4920
aattttttca gagcgttgga tcgagccttg gctcgaact atgagcgtcg ttatggctta     4980
aaacgtcatg gtatagaaac catgttggct ttgatgtcgc aaatagccaa tgcacatgct    5040
ttagggttgt tggttattga tgaaattcag catttaagcc gctctcgttc gggtggatct    5100
caagagatgc tgaacttttt tgtgacgatg gtgaatatta ttggcgtacc agtgatgttg    5160
attggtaccc ctaaagcacg agagatttt gaggctgatt tgcggtctgc acgtagaggg    5220
gcagggtttg gagctatatt ctgggatcct atacaacaaa cgcaacgtgg aaagcccaat    5280
caagagtgga tcgcttttac ggataatctt tggcaattac agcttttaca acgcaaagat    5340
gcgctgttat cggatgaggt ccgtgatgtg tggtatgagc taagccaagg agtgatggac    5400
attgtagtaa aacttttgt actcgctcag ctccgtgcgc tagctttagg caatgagcgt     5460
attaccgctg gtttattgcg gcaagtgtat caagatgagt taaagcctgt gcaccccatg    5520
ctagaggcat tacgctcggg tatcccagaa cgcattgctc gttattctga tctagtcgtt    5580
cccgagattg ataaacggtt aatccaactt cagctagata tcgcagcgat acaagaacaa    5640
acaccagaag aaaaagccct tcaagagtta gataccgaag atcagcgtca tttatatctg    5700
atgctgaaag aggattacga ttcaagcctg ttaattccca ctattaaaaa agcgtttagc    5760
cagaatccaa cgatgacaag acaaaagtta ctgcctcttg ttttgcagtg gttgatggaa   5820
ggcgaaacgg tagtgtcaga actagaaaag ccctccaaga gtaaaaaggt ttcggctata   5880
aaggtagtca gcccagcga ctgggatagc ttgcctgata cggatttacg ttatatctat    5940
tcacaacgcc aacctgaaaa aaccatgcat gaacggttaa aagggaaagg ggtaatagtg   6000
gatatggcga gcttatttaa acaagcaggt tagccatgag aaactttcct gttccgtact   6060
cgaatgagct gatttatagc actattgcac gggcaggcgt ttatcaaggg attgttagtc   6120
ctaagcagct gttggatgag gtgtatggca accgcaaggt ggtcgctacc ttaggtctgc    6180
cctcgcattt aggtgtgata gcaagacatc tacatcaaac aggacgttac gctgttcagc    6240 agcttatta tgagcatacc ttattccctt tatatgctcc gtttgtaggc aaggagcgcc      6300
gagacgaagc tattcggtta atggagtacc aagcgcaagg tgcggtgcat ttaatgctag    6360
gagtcgctgc ttctagagtt aagagcgata accgctttag atactgccct gattgcgttg   6420
ctcttcagct aaataggtat ggggaagcct tttggcaacg agattggtat ttgcccgctt   6480
tgccatattg tccaaaacac ggtgctttag tcttctttga tagagctgta gatgatcacc   6540
gacatcaatt ttgggctttg ggtcatactg agctgctttc agactacccc aaagactccc    6600
tatctcaatt aacagcacta gctgcttata tagcccctct gttagatgct ccacgagcgc    6660
aagagctttc cccaagcctt gagcagtgga cgctgtttta tcagcgctta gcgcaggatc   6720
```

```
tagggctaac caaaagcaag cacattcgtc atgacttggt ggcggagaga gtgaggcaga    6780
cttttagtga tgaggcacta gagaaactgg atttaaagtt ggcagagaac aaggacacgt    6840
gttggctgaa aagtatattc cgtaagcata gaaaagcctt tagttattta cagcatagta    6900
ttgtgtggca agccttattg ccaaaactaa cggttataga agcgctacag caggcaagtg    6960
ctcttactga gcactctata acgacaagac ctgttagcca gtctgtgcaa cctaactctg    7020
aagatttatc tgttaagcat aaagactggc agcaactagt gcataaatac caaggaatta    7080
aggcggcaag acagtcttta gagggtgggg tgctatacgc ttggctttac cgacatgaca    7140
gggattggct agttcactgg aatcaacagc atcaacaaga gcgtctggca cccgccccta    7200
gagttgattg gaaccaaaga gatcgaattg ctgtacgaca actattaaga atcataaagc    7260
gtctagatag tagccttgat cacccaagag cgacatcgag ctggctgtta aagcaaactc    7320
ctaacggaac ctctcttgca aaaaatctac agaaactgcc tttggtagcg ctttgcttaa    7380
agcgttactc agagagtgtg gaagattatc aaattagacg gattagccaa gcttttatta    7440
agcttaaaca ggaagatgtt gagcttaggc gctggcgatt attaagaagt gcaacgttat    7500
ctaaagagcg gataactgag gaagcacaaa gattcttgga aatggtttat ggggaagagt    7560
gagtggttag gctagctaca tttaatgaca atgtgcaggt tgtacatatt ggtcatttat    7620
tccgtaactc gggtcataag gagtggcgta ttttgtttg gtttaatcca atgcaagaac    7680
ggaaatggac tcgatttact catttgcctt tattaagtcg agctaaggtg gttaacagta    7740
caacaaagca aataaataag gcggatcgtg tgattgagtt tgaagcatcg gatcttcaac    7800
gagccaaaat aatcgatttt cctaatctct cgtcctttgc ttccgtacgc aacaaggatg    7860
gagcgcagag ttcatttatt tacgaagctg aaacaccata tagcaagact cgttatcaca    7920
tcccacagtt agagctagct cggtcattat ttttagggga tcctctagag tcgacctgca    7980
ggcatgcaag cttggctgtt ttggcggatg agagaagatt ttcagcctga tacagattaa    8040
atcagaacgc agaagcggtc tgataaaaca gaatttgcct ggcggcagta gcgcggtggt    8100
cccacctgac cccatgccga actcagaagt gaaacgccgt agcgccgatg gtagtgtggg    8160
gtctccccat gcgagagtag ggaactgcca ggcatcaaat aaaacgaaag gctcagtcga    8220
aagactgggc ctttcgtttt atctgttgtt tgtcggtgaa cgctctcctg agtaggacaa    8280
atccgccggg agcggatttg aacgttgcga agcaacggcc cggagggtgg cgggcaggac    8340
gcccgccata aactgccagg catcaaatta agcagaaggc catcctgacg gatggccttt    8400 ttgcgttct acaaactctt tgtttatttt tctaaatac attcaaatat gtatccgctc    8460
atgagacaat aaccctgata aatgcttcaa taatattgaa aaggaagag tatgagtatt    8520 caacatttcc gtgtcgccct tattcccttt tttgcggcat tttgccttcc tgttttgct    8580 cacccagaaa cgctggtgaa agtaaaagat gctgaagatc agttgggtgc acgagtgggt    8640
tacatcgaac tggatctcaa cagcggtaag atccttgaga gttttcgccc cgaagaacgt    8700
tttccaatga tgagcacttt taaagttctg ctatgtggcg cggtattatc ccgtgttgac    8760
gccgggcaag agcaactcgg tcgccgcata cactattctc agaatgactt ggttgagtac    8820
tcaccagtca cagaaaagca tcttacggat ggcatgacag taagagaatt atgcagtgct    8880
gccataacca tgagtgataa cactgcggcc aacttacttc tgacaacgat cggaggaccg    8940
aaggagctaa ccgcttttt gcacaacatg ggggatcatg taactcgcct tgatcgttgg    9000
gaaccggagc tgaatgaagc cataccaaac gacgagcgtg acaccacgat gcctgcagca    9060
```

```
atggcaacaa cgttgcgcaa actattaact ggcgaactac ttactctagc ttcccggcaa    9120
caattaatag actggatgga ggcggataaa gttgcaggac cacttctgcg ctcggccctt    9180
ccggctggct ggtttattgc tgataaatct ggagccggtg agcgtgggtc tcgcggtatc    9240
attgcagcac tggggccaga tggtaagccc tcccgtatcg tagttatcta cacgacgggg    9300
agtcaggcaa ctatggatga acgaaataga cagatcgctg ataggtgc ctcactgatt    9360 aagcattggt aactgtcaga ccaagtttac tcatatatac tttagattga tttacgcgcc    9420
ctgtagcggc gcattaagcg cggcgggtgt ggtggttacg cgcagcgtga ccgctacact    9480
tgccagcgcc ctagcgcccg ctcctttcgc tttcttccct tcctttctcg ccacgttcgc    9540
cgccggccag cctcgcagag caggattccc gttgagcacc gccaggtgcg aataagggac    9600
agtgaagaag gaacacccgc tcgcgggtgg gcctacttca cctatcctgc ccggcggcat    9660
caccggcgcc acaggtgcgg ttgctggcgc ctatatcgcc gacatcaccg atggggaaga    9720
tcgggctcgc cacttcgggc tcatgagcgc ttgtttcggc gtgggtatgg tggcaggccc    9780
cgtggccggg ggactgttgg cgccatctc cttgcatgca ccattcctg cggcggcggt      9840 gctcaacggc ctcaacctac tactgggctg cttcctaatg caggagtcgc ataagggaga    9900
gcgtcgatcc ccgacagtaa gacgggtaag cctgttgatg ataccgctgc cttactgggt    9960
gcattagcca gtctgaatga cctgtcacgg ataatccga agtggtcaga ctggaaaatc    10020
agagggcagg aactgctgaa cagcaaaaag tcagatagca ccacatagca gacccgccat    10080
aaaacgccct gagaagcccg tgacgggctt ttcttgtatt atgggtagtt ccttgcatg     10140 aatccataaa aggcgcctgt agtgccattt accccattc actgccagag ccgtgagcgc     10200
agcgaactga atgtcacgaa aaagacagcg actcaggtgc ctgatggtcg gagacaaaag    10260
gaatattcag cgatttgccc gagcttgcga gggtgctact taagcctttg gggttttaag    10320
gtctgttttg tagaggagca aacagcgttt gcgacatcct tttgtaatac tgcggaactg    10380
actaaagtag tgagttatac acagggctgg gatctattct tttatctttt ttttattctt    10440
tctttattct ataaattata accacttgaa tataaacaaa aaaacacac aaaggtctag     10500 cggaattttac agagggtcta gcagaattta caagtttttcc agcaaaggtc tagcagaatt   10560
tacagatacc cacaactcaa aggaaaagga ctagtaatta tcattgacta gcccatctca    10620
attggtatag tgattaaaat caccttagacc aattgagatg tatgtctgaa ttagttgttt   10680
tcaaagcaaa tgaactagcg attagtcgct atgacttaac ggagcatgaa accaagctaa    10740
ttttatgctg tgtggcacta ctcaacccca cgattgaaaa ccctacaagg aaagaacgga    10800
cggtatcgtt cacttataac caatacgttc agatgatgaa catcagtagg gaaaatgctt    10860
atggtgtatt agctaaagca accagagagc tgatgacgag aactgtggaa atcaggaatc    10920
ctttggttaa aggctttgag attttccagt ggacaaacta tgccaagttc tcaagcgaaa    10980
aattagaatt agttttttagt gaagagatat tgccttatct tttccagtta aaaaaattca   11040
taaaatataa tctggaacat gttaagtctt ttgaaaacaa atactctatg aggatttatg    11100
agtggttatt aaaagaacta acacaaaaga aaactcacaa ggcaaatata gagattagcc    11160
ttgatgaatt taagttcatg ttaatgcttg aaaataacta ccatgagttt aaaaggctta    11220
accaatgggt tttgaaacca ataagtaaag atttaaacac ttacagcaat atgaaattgg    11280
tggttgataa gcgaggccgc ccgactgata cgttgatttt ccaagttgaa ctagatagac    11340
aaatggatct cgtaaccgaa cttgagaaca accagataaa aatgaatggt gacaaaatac    11400
caacaaccat tacatcagat tcctacctac ataacggact aagaaaaaca ctacacgatg    11460
```

```
ctttaactgc aaaaattcag ctcaccagtt ttgaggcaaa attttttgagt gacatgcaaa    11520 gtaagtatga tctcaatggt tcgttctcat ggctcacgca aaaacaacga accacactag    11580
agaacatact ggctaaatac ggaaggatct gaggttctta tggctcttgt atctatcagt    11640
gaagcatcaa gactaacaaa caaaagtaga acaactgttc accgttacat atcaaaggga    11700
aaactgtcca tatgcacaga tgaaaacggt gtaaaaaaga tagatacatc agagctttta    11760 cgagttttg gtgcatttaa agctgttcac catgaacaga tcgacaatgt aacagatgaa    11820
cagcatgtaa cacctaatag aacaggtgaa accagtaaaa caaagcaact agaacatgaa    11880
attgaacacc tgagacaact tgttacagct caacagtcac acatagacag cctgaaacag    11940
gcgatgctgc ttatcgaatc aaagctgccg acaacacggg agccagtgac gcctcccgtg    12000
gggaaaaaat catggcaatt ctggaagaaa tagcgctttc agcctgtggg cggacaaaat    12060
agttgggaac tgggaggggt ggaaatggag tttttaagga ttatttaggg aagagtgaca    12120
aaatagatgg gaactgggtg tagcgtcgta agctaatacg aaaattaaaa atgacaaaat    12180
agtttggaac tagatttcac ttatctggtt ggtcgacact agtattaccc tgttatccct    12240
agatttaaat gatatcggat cctagtaagc cacgttttaa ttaatcagat gggtcaatag    12300
cggccgccaa ttcgcgcgcg aaggcgaagc ggcatgcatt tacgttgaca ccatcgaatg    12360
gtgcaaaacc tttcgcggta tggcatgata gcgcccggaa gagagtcaat tcagggtggt    12420
gaatgtgaaa ccagtaacgt tatacgatgt cgcagagtat gccggtgtct cttatcagac    12480 cgttcccgc gtggtgaacc aggccagcca cgtttctgcg aaaacgcggg aaaaagtgga    12540
agcggcgatg gcggagctga attacattcc caaccgcgtg gcacaacaac tggcgggcaa    12600
acagtcgttg ctgattggcg ttgccacctc cagtctggcc ctgcacgcgc cgtcgcaaat    12660
tgtcgcggcg attaaatctc gcgccgatca actgggtgcc agcgtggtgg tgtcgatggt    12720
agaacgaagc ggcgtcgaag cctgtaaagc ggcggtgcac aatcttctcg cgcaacgcgt    12780
cagtgggctg atcattaact atccgctgga tgaccaggat gccattgctg tggaagctgc    12840
ctgcactaat gttccggcgt tatttcttga tgtctctgac cagacaccca tcaacagtat    12900
tattttctcc catgaagacg gtacgcgact gggcgtggag catctggtcg cattgggtca    12960
ccagcaaatc gcgctgttag cgggcccatt aagttctgtc tcggcgcgtc tgcgtctggc    13020
tggctggcat aaatatctca ctcgcaatca aattcagccg atagcggaac gggaaggcga    13080
ctggagtgcc atgtccggtt ttcaacaaac catgcaaatg ctgaatgagg gcatcgttcc    13140
cactgcgatg ctggttgcca acgatcagat ggcgctgggc gcaatgcgcg ccattaccga    13200
gtccgggctg cgcgttggtg cggatatctc ggtagtggga tacgacgata ccgaagacag    13260
ctcatgttat atcccgccgt caaccaccat caaacaggat tttcgcctgc tggggcaaac    13320
cagcgtggac cgcttgctgc aactctctca gggccaggcg gtgaagggca atcagctgtt    13380
gcccgtctca ctggtgaaaa gaaaaccac cctggcgccc aatacgcaaa ccgcctctcc    13440
ccgcgcgttg gccgattcat taatgcagct ggcacgacag gtttcccgac tggaaagcgg    13500
gcagtgagcg caacgcaatt aatgtgagtt agcgcgaatt gatctggttt gacagcttat    13560
catcgactgc acggtgcacc aatgcttctg gcgtcaggca gccatcggaa gctgtggtat    13620
ggctgtgcag gtcgtaaatc actgcataat tcgtgtcgct caaggcgcac tcccgttctg    13680
gataatgttt tttgcgccga catcataacg gttctggcaa atattctgaa atgagctgtt    13740
gacaattaat catccggctc gtataatgtg tggaattgtg agcggataac aatttcacac    13800
```

```
aggaaacagc gccgctgaga aaaagcgaag cggcactgct ctttaacaat ttatcagaca    13860
atctgtgtgg gcactcgacc ggaattatcg attaacttta ttattaaaaa ttaaagaggt    13920
atatattaat gtatcgatta aataaggagg aataaaccat ggcggacacg ttattgattc    13980
tgggtgatag cctgagcgcc gggtatcgaa tgtctgccag cgcggcctgg cctgccttgt    14040
tgaatgataa gtggcagagt aaaacgtcgg tagttaatgc cagcatcagc ggcgacacct    14100
cgcaacaagg actggcgcgc cttccggctc tgctgaaaca gcatcagccg cgttgggtgc    14160
tggttgaact gggcggcaat gacggtttgc gtggttttca gccacagcaa accgagcaaa    14220
cgctgcgcca gattttgcag gatgtcaaag ccgccaacgc tgaaccattg ttaatgcaaa    14280
tacgtctgcc tgcaaactat ggtcgccgtt ataatgaagc ctttagcgcc atttacccca    14340
aactcgccaa agagtttgat gttccgctgc tgcccttttt tatggaagag gtctacctca    14400
agccacaatg gatgcaggat gacggtattc atcccaaccg cgacgcccag ccgtttattg    14460
ccgactggat ggcgaagcag ttgcagcctt tagtaaatca tgactcataa tgactctaga    14520
aataatttta gttaagtata agaaggagat ataccatggt gaagaaggtt tggcttaacc    14580
gttatcccgc ggacgttccg acggagatca accctgaccg ttatcaatct ctggtagata    14640
tgtttgagca gtcggtcgcg cgctacgccg atcaacctgc gtttgtgaat atgggggagg    14700
taatgacctt ccgcaagctg aagaacgca gtcgcgcgtt tgccgcttat ttgcaacaag    14760
ggttggggct gaagaaaggc gatcgcgttg cgttgatgat gcctaattta ttgcaatatc    14820
cggtggcgct gtttggcatt ttgcgtgccg ggatgatcgt cgtaaacgtt aacccgttgt    14880
ataccccgcg tgagcttgag catcagctta acgatagcgg cgcatcggcg attgttatcg    14940
tgtctaactt tgctcacaca ctggaaaaag tggttgataa aaccgccgtt cagcacgtaa    15000
ttctgacccg tatgggcgat cagctatcta cggcaaaagg cacggtagtc aatttcgttg    15060
ttaaatacat caagcgtttg gtgccgaaat accatctgcc agatgccatt tcatttcgta    15120
gcgcactgca taacggctac cggatgcagt acgtcaaacc cgaactggtg ccggaagatt    15180
tagcttttct gcaatacacc ggcggcacca ctggtgtggc gaaaggcgcg atgctgactc    15240
accgcaatat gctggcgaac ctggaacagg ttaacgcgac ctatggtccg ctgttgcatc    15300
cgggcaaaga gctggtggtg acggcgctgc cgctgtatca cattttttgcc ctgaccatta    15360 actgcctgct gtttatcgaa ctgggtgggc agaacctgct tatcactaac ccgcgcgata    15420
ttccagggtt ggtaaaagag ttagcgaaat atccgtttac cgctatcacg ggcgttaaca    15480
ccttgttcaa tgcgttgctg aacaataaag agttccagca gctggatttc tccagtctgc    15540
atctttccgc aggcggaggg atgccagtgc agcaagtggt ggcagagcgt tgggtgaaac    15600
tgacaggaca gtatctgctg gaaggctatg gccttaccga gtgtgcgccg ctggtcagcg    15660
ttaacccata tgatattgat tatcatagtg gtagcatcgg tttgccggtg ccgtcgacgg    15720
aagccaaact ggtggatgat gatgataatg aagtaccacc gggtcaaccg ggtgagcttt    15780
gtgtcaaagg accgcaggtg atgctgggtt actggcagcg tccggatgct acagatgaga    15840
tcatcaaaaa tggctggtta cacaccggcg acatcgcggt gatggatgaa gaagggttcc    15900
tgcgcattgt cgatcgtaaa aaagacatga ttctggtttc cggttttaac gtctatcccaa    15960 acgagattga agatgtcgtc atgcagcatc ctggcgtaca ggaagtcgcg gctgttggcg    16020
taccttccgg ctccagtggt gaagcggtga aatcttcgt agtgaaaaaa gatccatcgc    16080
ttaccgaaga gtcactggtg accttttgcc gccgtcagct cacgggctac aaagtaccga    16140
agctggtgga gtttcgtgat gagttaccga aatctaacgt cggaaaaatt ttgcgacgag    16200
```

```
aattacgtga cgaagcgcgc ggcaaagtgg acaataaagc ctgataactc tagaaataat    16260
ttaaatggaa ttcgaagctt gggcccgaac aaaaactcat ctcagaagag gatctgaata    16320
gcgccgtcga ccatcatcat catcatcatt gagtttaaac ggtctccagc ttggctgttt    16380
tggcggatga gagaagattt tcagcctgat acagattaaa tcagaacgca gaagcggtct    16440
gataaaacag aatttgcctg gcggcagtag cgcggtggtc ccacctgacc ccatgccgaa    16500
ctcagaagtg aaacgccgta gcgccgatgg tagtgtgggg tctccccatg cgagagtagg    16560
gaactgccag gcatcaaata aaacgaaagg ctcagtcgaa agactgggcc tttcgtttta    16620
tctgttgttt gtcggtgaac gctctcctga ttaattaaga cgtctaagaa accattatta    16680
tcatgacatt aacctataaa aataggcgta tcacgaggcc ctttcgtctt caagaatttt    16740
ataaaccgtg gagcgggcaa tactgagctg atgagcaatt tccgttgcac cagtgccctt    16800
ctgatgaagc gtcagcacga cgttcctgtc cacggtacgc ctgcggccaa atttgattcc    16860
tttcagcttt gcttcctgtc ggccctcatt cgtgcgctct aggatcctcc ggcgttcagc    16920
ctgtgccaca gccgacagga tggtgaccac catttgcccc atatcaccgt cggtactgat    16980
cccgtcgtca ataaaccgaa ccgctacacc ctgagcatca aactcttta tcagttggat     17040 catgtcggcg gtgtcgcggc caagacggtc gagcttcttc accagaatga catcaccttc    17100
ctccaccttc atcctcagca aatccagccc ttcccgatct gttgaactgc cggatgcctt    17160
gtcggtaaag atgcggttag cttttacccc tgcatctttg agcgctgagg tctgcctcgt    17220
gaagaaggtg ttgctgactc ataccaggcc tgaatcgccc catcatccag ccagaaagtg    17280
agggagccac ggttgatgag agctttgttg taggtggacc agttggtgat tttgaacttt    17340
tgctttgcca cggaacggtc tgcgttgtcg ggaagatgcg tgatctgatc cttcaactca    17400
gcaaaagttc gatttattca acaaagccgc cgtcccgtca agtcagcgta atgccctagg    17460
aggcgcgcca cggccgcgtc gaccccacgc ccctctttaa tacgacgggc aatttgcact    17520
tcagaaaatg aagagtttgc tttagccata acaaaagtcc agtatgcttt ttcacagcat    17580
aactggactg atttcagttt acaactattc tgtctagttt aagactttat tgtcatagtt    17640
tagatctatt ttgttcagtt taagacttta ttgtccgccc aca                      17683

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
gatgctggtg gcgaagctgt                                                    20

<210> SEQ ID NO 19
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
gttgcgacgg tggtacgcat aac                                                23
```

```
<210> SEQ ID NO 20
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
gaggaataaa ccatgcccat tcttgaaagc gtggg                                35

<210> SEQ ID NO 21
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
agctggagac cgtttaaact tataaaccgc tgtttgtcgc aaccg                     45

<210> SEQ ID NO 22
<211> LENGTH: 663
<212> TYPE: DNA
<213> ORGANISM: Unknown
<220> FEATURE:
<221> NAME/KEY: source
<223> OTHER INFORMATION: /note="Description of Unknown: Uncultured
      bacterium RM44"

<400> SEQUENCE: 22
atgcccattc ttgaaagcgt gggtttcatg aagacgctat gggagagcgg cggcgctcag     60
gtcgccctga tggaatcgcg ggaagagacc agccacatgg tcggcatcct ggaagggatc    120
gccgccgaac tctcgtggcg tcctggtacg cagcttcgcg attatcagga tagggcggcg    180
cacctggccg ttctggtcgg gtcggagatc gtcggcggct tgcagatcgt cacgtcgccg    240
tcagcggatt gccttcccta ccggctcgtc tggccggaag tctgcgtgcc ggacggtgcc    300
gcaatcgcgg acatcacgat tctggcgcta cggaaggaat accgcgcccg cttcaacctc    360
ttctggccgc tgtgcgtcga gctctggcgg cactgtgtcg cggagggtgc cacggagatg    420
cgcctggagg caacgccgga tacgctcagg ctctaccgcc gcatcggctg gccgctggag    480
gtcatcggcg acctgcgcct ccactggaac gagccgtgct tcctgtgccg gatggggatc    540
gtagatgtcg cgggggcgat ggttgtgcgg gccttgcagt ccgccaccta tcaggcggtc    600
ctcgcgggga tgagtcggcc tgtggcgtca gcgtcgccgg ttgcgacaaa cagcggttta    660
tga                                                                  663
```

UNITED STATES PATENT AND TRADEMARK OFFICE
CERTIFICATE OF CORRECTION

PATENT NO. : 9,683,247 B2
APPLICATION NO. : 14/394070
DATED : June 20, 2017
INVENTOR(S) : Jason J. Lutes and Stephen B. Del Cardayre Page 1 of 1

It is certified that error appears in the above-identified patent and that said Letters Patent is hereby corrected as shown below:

In the Claims

Claim 14, Column 87, Line 27-29:
Should read:
the microorganism is a *Saccharomyces cerevisiae, Candida lipolytica, Escherichia coli, Arthrobacter, Rhodotorula glutinins, Acetinobacter, Botryococcus*

Claim 14, Column 88, Line 2:
Should read:
*Thermosynechococcus elongatus* BP-1

Signed and Sealed this
Eighth Day of August, 2017

Joseph Matal
*Performing the Functions and Duties of the
Under Secretary of Commerce for Intellectual Property and
Director of the United States Patent and Trademark Office*